(12) United States Patent
Ge et al.

(10) Patent No.: US 12,378,222 B2
(45) Date of Patent: Aug. 5, 2025

(54) NLRP3 INFLAMMASOME INHIBITORS

(71) Applicant: Novartis AG, Basel (CH)

(72) Inventors: Xiaobin Ge, Changsu (CN); Henri Mattes, Monfort sur Argens (FR); Zhicong Shi, Shanghai (CN); Mei Xia, Shanghai (CN); Ning Ye, Suzhou (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/917,653

(22) Filed: Oct. 16, 2024

(65) Prior Publication Data

US 2025/0034114 A1    Jan. 30, 2025

Related U.S. Application Data

(63) Continuation of application No. 18/363,207, filed on Aug. 1, 2023.

(60) Provisional application No. 63/370,300, filed on Aug. 3, 2022.

(30) Foreign Application Priority Data

May 30, 2023    (WO) ................ PCT/CN2023/097282

(51) Int. Cl.
  *C07D 401/12*    (2006.01)
  *A61K 45/06*    (2006.01)
  *C07D 491/048*    (2006.01)

(52) U.S. Cl.
  CPC ............ *C07D 401/12* (2013.01); *A61K 45/06* (2013.01); *C07D 491/048* (2013.01)

(58) Field of Classification Search
  CPC .................................................. C07D 401/12
  See application file for complete search history.

(56) References Cited

U.S. PATENT DOCUMENTS

| | | | |
|---|---|---|---|
| 4,514,397 | A | 4/1985 | Wermuth et al. |
| 5,276,036 | A | 1/1994 | Bourguignon et al. |
| 8,729,263 | B2 | 5/2014 | Cheung et al. |
| 11,208,399 | B2 | 12/2021 | Farady et al. |
| 2012/0214785 | A1 | 8/2012 | Roth et al. |
| 2014/0051672 | A1 | 2/2014 | Cheung et al. |
| 2018/0008629 | A1 | 1/2018 | Dixit |
| 2019/0358226 | A1 | 11/2019 | Cheung et al. |
| 2020/0361898 | A1 | 11/2020 | Farady et al. |
| 2020/0361899 | A1 | 11/2020 | Farady et al. |

FOREIGN PATENT DOCUMENTS

| | | |
|---|---|---|
| CN | 103965169 A | 8/2014 |
| EP | 0072299 B1 | 12/1986 |
| EP | 0382634 B1 | 4/1994 |
| EP | 0514277 B1 | 12/1994 |
| EP | 0429344 B1 | 9/1996 |
| EP | 3272739 A1 | 1/2018 |
| WO | 0142241 A1 | 6/2001 |
| WO | 2004022556 A1 | 3/2004 |
| WO | 2006004589 A2 | 1/2006 |
| WO | 2006005608 A1 | 1/2006 |
| WO | 2007045478 A1 | 4/2007 |
| WO | 2008058064 A1 | 5/2008 |
| WO | 2009050227 A1 | 4/2009 |
| WO | 2010048149 A2 | 4/2010 |
| WO | 2012016133 A2 | 2/2012 |
| WO | 2012080729 A2 | 6/2012 |
| WO | 2014028459 A1 | 2/2014 |
| WO | 2016022626 A1 | 2/2016 |
| WO | 2016118638 A1 | 7/2016 |
| WO | 2016128343 A1 | 8/2016 |
| WO | 2016131098 A1 | 8/2016 |
| WO | 2016138114 A1 | 9/2016 |
| WO | 2017100726 A1 | 6/2017 |
| WO | 2017123991 A1 | 7/2017 |
| WO | 2018152396 A1 | 8/2018 |
| WO | 2018232039 A1 | 12/2018 |
| WO | 2019008025 A1 | 1/2019 |
| WO | 2019014402 A1 | 1/2019 |
| WO | 2019028440 A1 | 2/2019 |

(Continued)

OTHER PUBLICATIONS

Cheung, et al., Discovery of Small Molecule Splicing Modulators of Survival Motor Neuron-2 (SMN2) for the Treatment of Spinal Muscular Atrophy (SMA), Journal of Medicinal Chemistry, 61, 11021-11036, Nov. 8, 2018.
Garib, et al., Inflammasomes and inflammation, Russian Journal of Immunology, 11(20), 620-626, 2017.
Hallot, et al., Synthesis and Activity of 6-Aryl-3-(hydroxypolymethyleneamino)pyridazines in Animal Models of Epilepsy, Journal of Medicinal Chemistry, 29(3), 369-375, 1986.
Lin, et al., Microwave-Enhanced Efficient Synthesis of Diversified 3,6-Disubstituted Pyridazines, Journal of Combinatorial Chemistry, 9(5), 742-744, Jul. 21, 2007.
Nasonov, et al., The role of interleukin 1 in the development of human diseases, Scientific and practical rheumatology, 54(1), 60-77, 2016.

(Continued)

*Primary Examiner* — Brian E McDowell
(74) *Attorney, Agent, or Firm* — Timothy P. O'Dea

(57) ABSTRACT

The present invention relates to novel pyridazin-3-yl phenol compounds of formula (I):

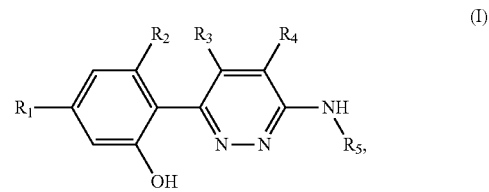

wherein $R^1$, $R^2$, $R^3$, $R^4$ and $R^5$ are defined herein, which inhibit NOD-like receptor protein 3 (NLRP3) inflammasome activity. The invention further relates to the processes for their preparation, pharmaceutical compositions and medicaments containing them, and their use in the treatment of diseases and disorders mediated by NLRP3.

18 Claims, 15 Drawing Sheets

(56) References Cited

FOREIGN PATENT DOCUMENTS

| WO | 2019034690 | A1 | 2/2019 |
| WO | 2019060917 | A2 | 3/2019 |
| WO | 2019075265 | A1 | 4/2019 |
| WO | 2019092170 | A1 | 5/2019 |
| WO | 2019191229 | A1 | 10/2019 |
| WO | 2019199972 | A1 | 10/2019 |
| WO | 2019207538 | A1 | 10/2019 |
| WO | 2020234715 | A1 | 11/2020 |
| WO | 2021193897 | A1 | 9/2021 |
| WO | 2022135567 | A1 | 6/2022 |
| WO | 2022166890 | A1 | 8/2022 |

OTHER PUBLICATIONS

Voet, et al., Inflammasomes in neuroinflammatory and neurodegenerative diseases, EMBO Molecular Medicine, 11, e10248, Apr. 23, 2019.

Wermuth, et al., SR46559 A and related aminopyridazines are potent muscarinic agonists with no cholinergic syndrome, Bioorganic & Medicinal Chemistry Letters, 2(8), 833-838, 1992.

NLRP3 INFLAMMASOME INHIBITORS

RELATED APPLICATIONS

This application is a continuation of U.S. application Ser. No. 18/363,207, filed Aug. 1, 2023, which claims the benefit of and priority to under 35 U.S.C. 119 of Chinese patent application No. PCT/CN2023/097282, filed May 30, 2023, and to U.S. Provisional Application No. 63/370,300, filed Aug. 3, 2022, the entire contents of which are hereby incorporated by reference in their entirety.

FIELD OF THE INVENTION

The present invention relates to novel pyridazin-3-yl phenol compounds that are useful as inhibitors of NOD-like receptor protein 3 (NLRP3) inflammasome pathway. The present invention also relates to processes for the preparation of said compounds, pharmaceutical compositions comprising said compounds, methods of using said compounds in the treatment and diagnosis of various diseases and disorders mediated by NLRP3, and medicaments containing them.

BACKGROUND OF THE INVENTION

The NOD-like receptor protein 3 (NLRP3) is a protein-coding gene: the protein belongs to the family of nucleotide-binding and oligomerization domain-like receptors (NLRs) and is also known as "pyrin domain-containing protein 3" (Inoue et al., *Immunology*, 2013, 139, 11-18). This gene encodes a protein containing a pyrin domain, a nucleotide-binding site domain (NBD), and a leucine-rich repeat (LRR) motif. In response to sterile inflammatory danger signals, NLRP3 interacts with an adapter protein, apoptosis-associated speck-like protein (ASC) and procaspase-1 to form the NLRP3 inflammasome. NLRP3 inflammasome activation then leads to the release of the inflammatory cytokines IL-1β (interleukin-1β) and IL-18 (interleukin-18), and when dysregulated, can drive pathology in a number of disease settings.

NLRP3 inflammasome activation normally requires two steps. The first step involves a priming signal in which pathogen activated molecular patterns (PAMPs) or danger-activated molecular patterns (DAMPs) are recognized by Toll-like receptors, leading to activation of nuclear factor kappa B (NF-κB)-mediated signaling, which in turn up-regulates transcription of inflammasome-related components, including inactive NLRP3 and proIL-1β (pro-interleukin-1β) (Bauernfeind et al *J. Immunol.* 2009, 183, 787-791; Franchi et al *Nat. Immunol.* 2012, 13, 325-332, Franchi et al *J. Immunol.* 2014, 193, 4214-4222). The second step is the oligomerization of NLRP3 and subsequent assembly of NLRP3, ASC, and procaspase-1 into an inflammasome complex. This triggers the transformation of procaspase-1 to caspase-1, and the production and secretion of mature IL-1β and IL-18 (Kim et al *J. Inflamm.* 2015, 12, 41; Ozaki et al *J. Inflamm. Res.* 2015, 8, 15-27; Rabeony et al. *Eur. J. Immunol.* 2015, 45, 2847-2857).

NLRP3 inflammasome activation has been linked to various inflammasome-related diseases/disorders, immune diseases, inflammatory diseases, auto-immune diseases and auto-inflammatory diseases, for example, autoinflammatory fever syndrome such as cryopyrin-associated periodic syndrome (CAPS) (Mortimer et al *Nature Immunol.* 2016, 17(10), 1176-1188); sickle cell disease; systemic lupus erythematosus (SLE); liver related diseases/disorders such as chronic liver disease, viral hepatitis, non-alcoholic steatohepatitis (NASH), alcoholic steatohepatitis, and alcoholic liver disease (Petrasek et al *J. Clin. Invest.* 2012, 122, 3476-89; Petrasek et al. *Nat. Rev. Gastroenterol. Hepatol.* 2015, 12, 387-400; Mridha et al *J. Hepatol.* 2017, 66, 1037-46); inflammatory arthritis related disorders, such as gout, pseudogout (chondrocalcinosis), osteoarthritis (Ridker et al *N. Engl. J. Med.* 2017, 377, 1119-31), and rheumatoid arthritis (Mathews et al *Ann. Rheum. Dis.* 2014, 73, 1202-10), acute or chronic arthropathy; kidney related diseases such as hyperoxaluria (Knauf et al. *Kidney Int.* 2013, 84, 895-901), lupus nephritis, hypertensive nephropathy (Krishnan et al *Br. J. Pharmacol.* 2016, 173, 752-65), hemodialysis related inflammation and diabetic nephropathy which is a kidney-related complication of diabetes (Type 1, Type 2 and mellitus diabetes), also called diabetic kidney disease (Shahzad et al *Kidney Int.* 2015, 87, 74-84). Emerging studies have revealed the involvement of the increased production of IL-1β and IL-18 by the NLRP3 inflammasome can contribute to the onset and progression of various diseases such as neuroinflammation-related disorders, e.g. brain infection, acute injury, multiple sclerosis, Alzheimer's disease, and neurodegenerative diseases (Shao et al. *Front. Pharmacol.* 2015, 6, 262); cardiovascular/metabolic disorders/diseases, e.g. cardiovascular risk reduction (CvRR), atherosclerosis, type I and type II diabetes and related complications (e.g. nephropathy, retinopathy), peripheral artery disease (PAD), acute heart failure and hypertension (Ridker et al *N. Engl. J. Med.* 2017, 377, 1119-31; Vandanmasgar et al *Nat. Med.* 2011, 17, 179-88; Hu et al *Proc. Natl. Acad. Sci.* 2015, 112, 11318-23; Antonopoulos et al *Curr. Opin. Pharmacol.* 2017, 39, 1-8; Toldo S et al *Nat. Rev. Cardiol.* 2018, 15, 203-214); wound healing and scar formation; inflammatory skin diseases, e.g. acne, hidradenitis suppurativa (Sweeney et al *Br. J. Dermatol.* 2015, 173, 1361), asthma, sarcoidosis, age-related macular degeneration; cancer related diseases/disorders, e.g. myeloproliferative neoplasms, leukemias, myelodysplastic syndromes (MDS), myelofibrosis, lung cancer, colon cancer (Ridker et al *Lancet* 2017, 390, 1833-42; Derangere et al *Cell. Death Differ.* 2014, 21, 1914-24, Gelfo et al *Oncotarget* 2016, 7, 72167-83, Baiorka et al *Blood* 2016, 128, 2960-75; Carey et al *Cell. Rep.* 2017, 18, 3204-18). Those diseases/disorders that are immune or inflammatory in nature usually are difficult to diagnose or treat efficiently. Most treatments include treating of the symptoms, slowing down the progression of the disease/disorder, change in lifestyle and surgery as a last resort (e.g., open heart surgery for advance forms of atherosclerosis). Recent studies have linked mitochondrial dysfunction and NLRP3 activation in neuroinflammation related diseases such as Parkinson's (Sarkar et al *npj Parkinson's disease* 2017, 3:30; Zhou et al *Nature,* 2011, 469, 221). One of the major problems associated with the mitochondrial modulators is their poor metabolic stability; thus there is a need for selective and stable inhibitors in neuroinflammation of this nature (Lee et al *Eur J. Org. Chem.* 2017, 141, 240).

Therefore, there is a need for inhibitors of the NLRP3 inflammasome pathway to provide new and/or alternative treatments for these inflammasome-related diseases/disorders and others such as autoinflammatory fever syndrome cryopyrin-associated periodic syndrome (e.g. CAPS), sickle cell disease, chronic liver disease, nonalcoholic steatohepatitis (NASH), gout, hyperoxaluria, secondary hyperoxaluria, pseudogout (chondrocalcinosis), Type I/Type II diabetes and related complications (e.g. nephropathy, retinopathy), neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

WO2020/234715 describes pyridazin-3-yl phenol compounds as NLRP3 inflammasome inhibitors. WO2022/135567 describes pyridazine containing compounds as NLRP3 inflammasome inhibitors. WO2022/166890 describes substituted pyridazine phenol derivatives as NLRP3 inflammasome inhibitors.

SUMMARY OF THE INVENTION

The invention provides compounds or pharmaceutically acceptable salts thereof, pharmaceutical compositions thereof, and combination thereof, which compounds inhibit the NLRP3 inflammasome pathway. The invention further provides methods of treating, diagnosis, or preventing, disease and/or disorders related to NLRP3, comprising administering to a subject in need thereof an effective amount of the compounds of the invention, or a pharmaceutically acceptable salt thereof.

Various embodiments of the invention are described herein.

As a first aspect, the invention provides a compound of formula (I), or a pharmaceutically acceptable salt thereof:

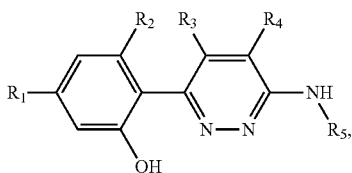

wherein
$R^1$ is Cl, $CH_3$, —$OCF_3$ or $CF_3$;
$R^2$ is halo, $C_1$-$C_4$alkyl or halo$C_1$-$C_4$alkyl;
$R^3$ is H, CN, $C_1$-$C_4$alkyl or halo$C_1$-$C_4$alkyl;
$R^4$ is —$(CH_2)_n$—OH, wherein n is 1, 2, 3 or 4;
$R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2H$; or
$R^5$ is an aryl or heteroaryl, which is unsubstituted or substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl which is unsubstituted or substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —$NH(C_1$-$C_4$alkyl), and —$N(C_1$-$C_4$alkyl)_2$.

In another aspect, the invention provides a pharmaceutical composition comprising a therapeutically effective amount of a compound according to formula (I), or subformulae or species thereof as disclosed herein, or a pharmaceutically acceptable salt thereof, and one or more pharmaceutically acceptable carriers. The pharmaceutical composition is useful in the treatment of diseases and/or disorders related to the NLRP3 activity.

In another aspect, the invention provides a pharmaceutical composition comprising a compound according to formula (I), or subformulae or species thereof as disclosed herein, or a pharmaceutically acceptable salt thereof, and one or more pharmaceutically acceptable carriers. The pharmaceutical composition is useful in the treatment of diseases and/or disorders related to the NLRP3 activity.

In another aspect, the invention provides a combination, in particular a pharmaceutical combination, comprising a therapeutically effective amount of a compound according to the definition of compound of formula (I), or subformulae or species thereof as disclosed herein, or a pharmaceutically acceptable salt thereof, and one or more therapeutic agents.

In another aspect, the invention provides a combination, in particular a pharmaceutical combination, as disclosed herein, for use as a medicament.

In another aspect, the invention provides a compound of formula (I), or subformulae or species thereof as disclosed herein, or a pharmaceutically acceptable salt thereof, for use in the treatment of a disease or disorder in which the NLRP3 signaling contributes to the pathology, and/or symptoms, and/or progression, of said disease or disorder. In another aspect, the invention provides a method of treating a disease or disorder in which the NLRP3 signaling contributes to the pathology, and/or symptoms, and/or progression, of said disease or disorder, comprising administering a therapeutically effective amount of a compound of formula (I), subformulae or species thereof as disclosed herein, or a pharmaceutically acceptable salt thereof.

In another aspect, the invention provides a method of inhibiting the NLRP3 inflammasome activity in a subject in need thereof, the method comprises administering to the subject in need thereof a therapeutically effective amount of a compound of formula (I), subformulae or species thereof as disclosed herein, or a pharmaceutically acceptable salt thereof.

In another aspect, the invention relates to the use of a compound of formula (I), or subformulae thereof, as disclosed herein, or a pharmaceutically acceptable salt thereof, as a medicament.

In another aspect, the invention relates to a compound of formula (I), or subformulae thereof, as disclosed herein, or a pharmaceutically acceptable salt thereof, for use as a medicament.

In another aspect, the invention provides a compound of formula (I), or subformulae thereof, as disclosed herein, or a pharmaceutically acceptable salt thereof, for use in the treatment of a disease or disorder selected from inflammasome-related disease/disorders, immune diseases, inflammatory diseases, auto-immune diseases, or auto-inflammatory diseases.

In another aspect, the invention provides a compound of formula (I), or subformulae thereof, as disclosed herein, or a pharmaceutically acceptable salt thereof, for use in the manufacture of a medicament for the treatment of a disease or disorder selected from inflammasome-related disease/disorders, immune diseases, inflammatory diseases, auto-immune diseases, or auto-inflammatory diseases.

In another aspect, the invention provides radioactive compounds of formula (I), or pharmaceutically acceptable salts thereof, their preparation, and their use as radiotracers/markers for imaging techniques and diagnostics tools for NLRP3 related diseases or disorders, such as those defined herein.

DETAILED DESCRIPTION OF THE INVENTION

The invention therefore provides a compound of formula (I),

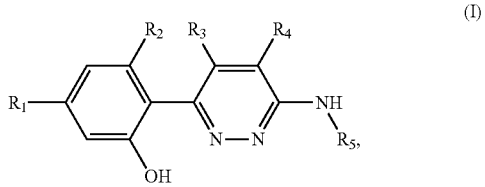

wherein
$R^1$ is Cl, $CH_3$, —$OCF_3$ or $CF_3$;
$R^2$ is halo, $C_1$-$C_4$alkyl or halo$C_1$-$C_4$alkyl;
$R^3$ is H, CN, $C_1$-$C_4$alkyl or halo$C_1$-$C_4$alkyl;
$R^4$ is —$(CH_2)_n$—OH, wherein n is 1, 2, 3 or 4;
$R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2H$; or
$R^5$ is an aryl or heteroaryl, which is unsubstituted or substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl which is unsubstituted or substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —NH($C_1$-$C_4$alkyl), and —N($C_1$-$C_4$alkyl)$_2$; or a pharmaceutically acceptable salt thereof.

Definitions

For purpose of interpreting this specification, the following definitions will apply unless specified otherwise and when appropriate, terms used in the singular will also include the plural and vice versa.

It must be noted that as used herein and in the appended claims, the singular forms "a", "an" and "the", and similar terms, used in the context of the present invention (especially in the context of the claims) are to be construed to cover both the singular and the plural referents unless the context clearly dictates otherwise, or clearly contradicted by the context. Thus, for example, reference to "the compound" includes reference to one or more compounds; and so forth.

As used herein, the term "$C_1$-$C_4$alkyl" refers to a straight or branched hydrocarbon chain radical consisting solely of carbon and hydrogen atoms, containing no unsaturation, having from one to four carbon atoms, and which is attached to the rest of the molecule by a single bond. Examples of $C_1$-$C_4$alkyl include, but are not limited to, methyl, ethyl, n-propyl, 1-methylethyl (iso-propyl), n-butyl.

As used herein, the term "Halogen" or "Halo" refers to bromo, chloro, fluoro, or iodo.

As used herein, the term "halo$C_1$-$C_4$alkyl" or "halogen$C_1$-$C_4$alkyl" refers to a $C_1$-$C_4$alkyl radical, as defined above, substituted by one or more halo radicals, as defined above. Examples of halo$C_1$-$C_4$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "$C_1$-$C_4$alkoxy" refers to a radical of the formula —$OR_a$ where $R_a$ is a $C_1$-$C_4$alkyl radical as generally defined above. Examples of "$C_1$-$C_4$alkoxy" include, but are not limited to, methoxy, ethoxy, propoxy, isopropoxy, butoxy, and isobutoxy.

As used herein, the term "$C_1$-$C_4$haloalkoxy" refers to a radical "$C_1$-$C_4$alkoxy" as defined above substituted by one or more halo radicals, as defined above. Examples of halo$C_1$-$C_4$alkoxy include, but are not limited to, trifluoromethoxy, difluoromethoxy, fluoromethoxy, trichloromethoxy.

As used herein, the term "hydroxy$C_1$-$C_4$alkyl" refers to a $C_1$-$C_4$alkyl radical wherein one of the hydrogen atoms of the $C_1$-$C_4$alkyl radical is replaced by OH. Examples of hydroxy$C_1$-$C_4$alkyl include, but are not limited to, hydroxymethyl, 2-hydroxy-ethyl, 2-hydroxy-propyl, 3-hydroxy-propyl and 4-hydroxy-butyl.

As used herein, the term "oxo" refers to an oxygen substituent, for example an oxygen joined by a double bond (e.g. forming a ketone).

As used herein, the term "heterocyclyl" or "heterocyclic" refers to a stable 5- or 6-membered non-aromatic monocyclic ring, or a bicyclic ring, or a polycyclic ring radical; which has 3 to 24, preferably 4 to 16, most preferably 5 to 10 ring atoms; wherein one or more, preferably one to four, especially one or two ring atoms are a heteroatom selected from, for example, oxygen, sulphur, and nitrogen (the remaining ring atoms therefore being carbon). The term heterocyclyl excludes heteroaryl. The heterocyclic group can be attached to the rest of the molecule through a heteroatom, selected from, for example, oxygen, sulfur, nitrogen, or a carbon atom. The heterocyclyl can include, for example, fused or bridged rings, as well as spirocyclic rings. For example, the term "heterocyclyl" can refer to a 5-7 monocyclic ring containing 1, 2, or 3 heteroatoms, selected from oxygen, nitrogen and sulfur. Examples of mono heterocyclyl include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, oxapinyl, oxaazepanyl, oxathianyl, thiepanyl, azepanyl, dioxepanyl, and diazepanyl. Preferably, the mono heterocyclyl is morpholino, pyrrolidine or piperidinyl. Examples of bicyclic heterocyclyl include, for example, azabicyclooctanyl, or octahydroindolizinyl. According to the present invention, the term "heterocyclyl" subtituted with an "OH" substituent also includes a "heterocyclyl" wherein the heteroatom, e.g. N or S, is oxidized, to obtain, for example, a heterocyclyl N-oxide, heterocyclyl S-oxide, or a heterocyclyl S-dioxide. Examples of heterocyclyl N-oxide, include, pyperidinyl-N-oxide, 1-methylpyrrolidine 1-oxide. Examples of heterocyclyl S-oxide or heterocyclyl S-dioxide, include, tetrahydro-2H-thiopyran-1-oxide, tetrahydro-2H-thiopyran-1,1-dioxide, and tetrahydrothiophene-1-oxide.

As used herein, the term "aryl" refers to an aromatic hydrocarbon group having 6-20 carbon atoms in the ring portion. Typically, aryl is monocyclic, bicyclic or tricyclic aryl having 6-20 carbon atoms. In a preferred embodiment, aryl is phenyl.

As used herein, the term "heteroaryl" refers to a 5- or 6-membered aromatic monocyclic ring radical, which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "$C_3$-$C_6$cycloalkyl" refers to a stable monocyclic saturated hydrocarbon radical consisting solely of carbon and hydrogen atoms, having from three to 6 carbon ring atoms. Examples of monocyclic $C_3$-$C_6$cycloalkyl include, but are not limited to, cyclopropyl, cyclobutyl, cyclopentyl, and cyclohexyl. Preferably, the "$C_3$-$C_6$cycloalkyl" is a cyclopropyl or cyclobutyl.

Unless specified otherwise, the term "compounds of the (present) invention" refers to compounds of formula (I), and subformulae thereof (such as compounds of formulae (II), (II-A), (III), (III-A), etc. as described herein), and salts thereof, as well as all stereoisomers (including diastereoisomers and enantiomers), rotamers, tautomers and isotopically labeled compounds (including deuterium substitutions). The term "compounds of the (present) invention" or "a compound of the (present) invention" refers to a compound as defined in any one of embodiments mentioned below.

Various enumerated embodiments of the invention are described herein, it will be recognized that features specified in each embodiment may be combined with other specified features to provide further embodiments of the present invention.

As an embodiment 1.0, the invention therefore provides a compound of formula (I):

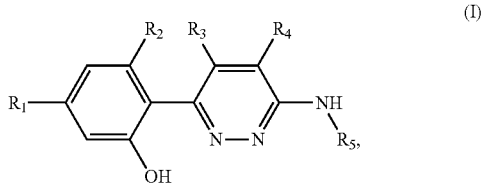

wherein
$R^1$ is Cl, $CH_3$, —$OCF_3$ or $CF_3$;
$R^2$ is halo, $C_1$-$C_4$alkyl or halo$C_1$-$C_4$alkyl;
$R^3$ is H, CN, $C_1$-$C_4$alkyl or halo$C_1$-$C_4$alkyl;
$R^4$ is —$(CH_2)_n$—OH, wherein n is 1, 2, 3 or 4;
$R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2$H; or
$R^5$ is an aryl or heteroaryl, which is unsubstituted or substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl which is unsubstituted or substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —$NH(C_1$-$C_4$alkyl), and —$N(C_1$-$C_4$alkyl)$_2$, or a pharmaceutically acceptable salt thereof.

As an embodiment 2.0, there is provided a compound according to embodiment 1.0, or a pharmaceutically acceptable salt thereof, wherein
$R^1$ is —$OCF_3$ or $CF_3$;
$R^2$ is $C_1$-$C_4$alkyl or halo$C_1$-$C_4$alkyl;
$R^3$ is H, $C_1$-$C_4$alkyl or halo$C_1$-$C_4$alkyl;
$R^4$ is —$CH_2$—OH;
$R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2$H; or
$R^5$ is an aryl or heteroaryl, which is unsubstituted or substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl which is unsubstituted or substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —$NH(C_1$-$C_4$alkyl), and —$N(C_1$-$C_4$alkyl)$_2$.

As an embodiment 3.0, there is provided a compound according to embodiment 1.0 or 2.0, or a pharmaceutically acceptable salt thereof, wherein
$R^1$ is —$OCF_3$ or $CF_3$;
$R^2$ is $C_1$-$C_4$alkyl;
$R^3$ is H;
$R^4$ is —$CH_2$—OH;
$R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo, and —$CO_2$H; or
$R^5$ is an aryl or heteroaryl, which is unsubstituted or substituted with 1 to 2 substituents independently selected from halo, halo$C_1$-$C_4$alkyl, $C_1$-$C_4$alkyl, and —$SO_2NH_2$; or
$R^5$ is $C_3$-$C_6$cycloalkyl which is unsubstituted or substituted with 1 to 3 substituents independently selected from $C_1$-$C_4$alkyl, halo, halo$C_1$-$C_4$alkyl, and —OH; or
$R^5$ is $C_2$-$C_6$alkyl substituted with 1 or more substituents independently selected from —OH, $C_1$-$C_4$alkoxy, halo, —$NH_2$, —$NH(C_1$-$C_4$alkyl), and —$N(C_1$-$C_4$alkyl)$_2$.

As an embodiment 4.0, there is provided a compound according to any one of embodiments 1.0-3.0, or a pharmaceutically acceptable salt thereof, wherein $R^5$ is a mono or bicyclic heterocyclyl, which is unsubstituted or substituted with 1 to 2 substituents independently selected from $C_1$-$C_4$alkyl, halo$C_1$-$C_4$alkyl, hydroxy$C_1$-$C_4$alkyl, —OH, halo, oxo and —$CO_2$H.

As an embodiment 4.1, there is provided a compound according to any one of embodiments 1.0-3.0, or a pharmaceutically acceptable salt thereof, wherein $R^5$ is selected from the following:

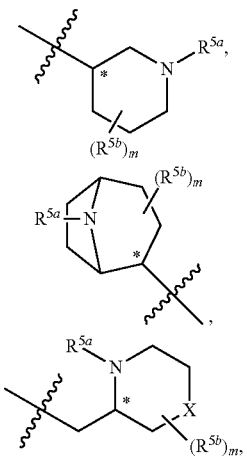

-continued

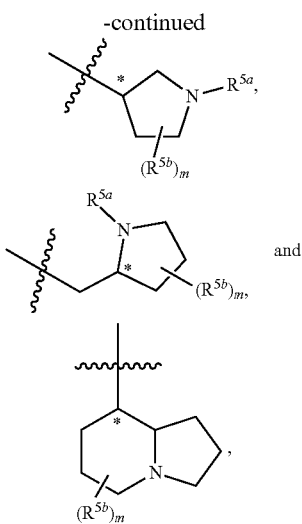

wherein $R^{5a}$ is independently selected from $C_1$-$C_4$alkyl, hydroxy$C_1$-$C_4$alkyl, and H; and $R^{5b}$ is independently selected from —OH, hydroxy$C_1$-$C_4$alkyl, H, halo, oxo, halo$C_1$-$C_4$alkyl, and —$CO_2$H; X is O or $CH_2$; and m is 0 or 1, and wherein "*" indicates the carbon attached to the pyridazine-amine.

As an embodiment 4.2, there is provided a compound according to any one of embodiments 1.0-3.0, or a pharmaceutically acceptable salt thereof, wherein $R^5$ is selected from the following:

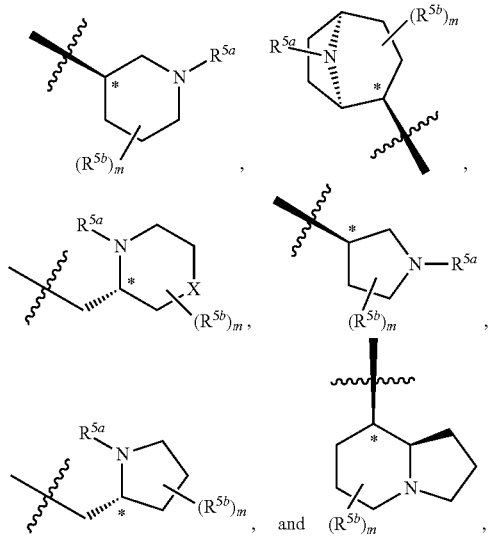

wherein $R^{5a}$ is independently selected from $C_1$-$C_4$alkyl, hydroxy$C_1$-$C_4$alkyl, and H; and $R^{5b}$ is independently selected from —OH, $C_1$-$C_4$alkyl, hydroxy$C_1$-$C_4$alkyl, H, halo, oxo, halo$C_1$-$C_4$alkyl, and —$CO_2$H; X is O or $CH_2$; and m is 0 or 1, and wherein "*" indicates the carbon atom attached to the pyridazine-amine.

As an embodiment 4.3, there is provided a compound according to any one of embodiments 1.0-3.0, or a pharmaceutically acceptable salt thereof, wherein $R^5$ is selected from the following:

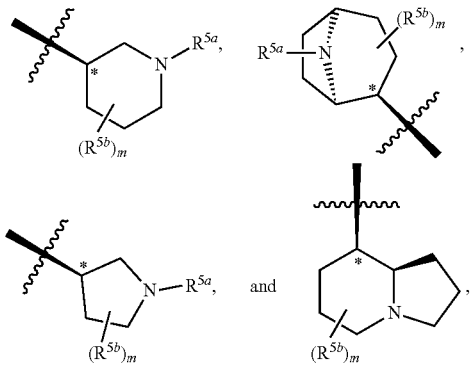

wherein $R^{5a}$ is independently selected from $C_1$-$C_4$alkyl, hydroxy$C_1$-$C_4$alkyl, and H; and $R^{5b}$ is independently selected from —OH, $C_1$-$C_4$alkyl, hydroxy$C_1$-$C_4$alkyl, H, halo, oxo, halo$C_1$-$C_4$alkyl, and —$CO_2$H; and m is 0 or 1, and wherein "*" indicates the carbon atom attached to the pyridazine-amine.

As an embodiment 4.4, there is provided a compound according to any one of embodiments 1.0-3.0, or a pharmaceutically acceptable salt thereof, wherein $R^5$ is

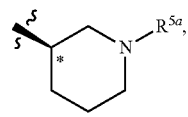

wherein $R^{5a}$ is independently selected from $C_1$-$C_4$alkyl, hydroxy$C_1$-$C_4$alkyl and H, and wherein "*" indicates the carbon atom attached to the pyridazine-amine.

As an embodiment 4.5, there is provided a compound according to embodiment 4.4, or a pharmaceutically acceptable salt thereof, wherein $R^{5a}$ is methyl or H, in particular $R^{5a}$ is methyl.

As an embodiment 5.0, there is provided a compound according to any one of embodiments 1.0-3.0, or a pharmaceutically acceptable salt thereof, wherein $R^5$ is an aryl or heteroaryl, which is unsubstituted or substituted with 1 to 2 substituents independently selected from halo, halo$C_1$-$C_4$alkyl, $C_1$-$C_4$alkyl and —$SO_2NH_2$.

As an embodiment 5.1, there is provided a compound according to any one of embodiments 1.0-3.0, or a pharmaceutically acceptable salt thereof, wherein $R^5$ is preferably selected from the following structure:

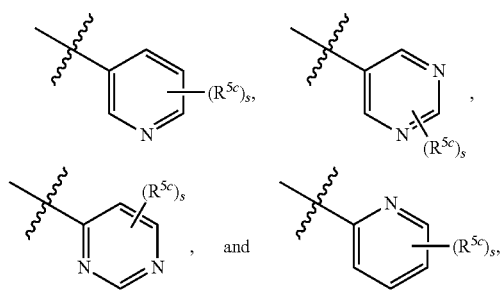

wherein $R^{5c}$ is independently selected from H, $C_1$-$C_4$alkyl, and —$SO_2NH_2$; and s is 0, 1 or 2.

As an embodiment 5.2, there is provided a compound according to any one of embodiments 1.0-3.0, or a pharmaceutically acceptable salt thereof, wherein $R^5$ is preferably selected from the following structure:

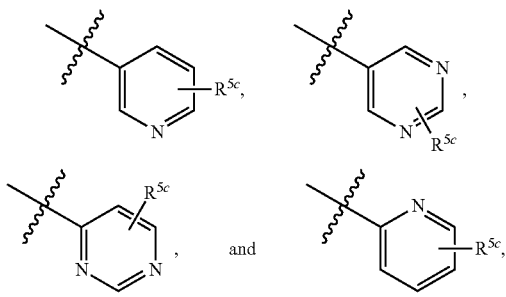

wherein $R^{5c}$ is independently selected from H, $C_1$-$C_4$alkyl and —$SO_2NH_2$.

As an embodiment 5.3, there is provided a compound according to any one of embodiments 1.0-3.0, or a pharmaceutically acceptable salt thereof, wherein $R^5$ is preferably selected from the following structure:

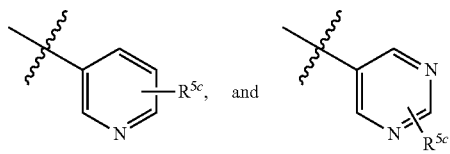

wherein $R^{5c}$ is independently selected from H and $C_1$-$C_4$alkyl.

As an embodiment 6.0, the invention provides a compound according to any one of embodiments 1.0-3.0, or a pharmaceutically acceptable salt thereof, wherein $R^5$ is $C_3$-$C_6$cycloalkyl which is unsubstituted or substituted with 1 to 3 substituents independently selected from $C_1$-$C_4$alkyl, halo, halo$C_1$-$C_4$alkyl and —OH.

As an embodiment 6.1, there is provided a compound according to any one of embodiments 1.0-3.0, or a pharmaceutically acceptable salt thereof, wherein $R^5$ is selected from the following structure:

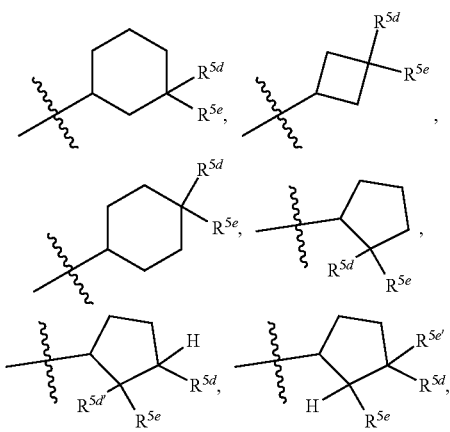

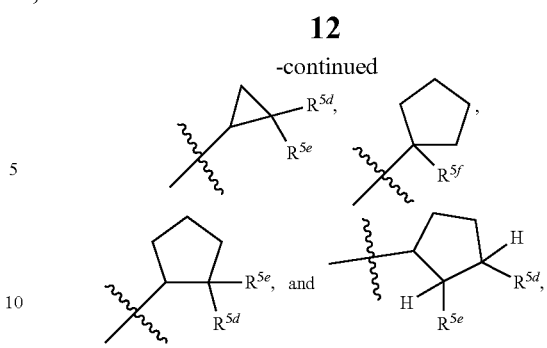

wherein $R^{5e}$, $R^{5e'}$, $R^{5d}$, $R^{5d'}$ and $R^{5f}$ are independently selected from H, $C_1$-$C_4$alkyl, halo, halo$C_1$-$C_4$alkyl and —OH.

As an embodiment 6.2, there is provided a compound according to any one of embodiments 1.0-3.0, or a pharmaceutically acceptable salt thereof, wherein $R^5$ is selected from the following structure:

wherein $R^{5d}$ and $R^{5d'}$ are independently selected from H, halo, halo$C_1$-$C_4$alkyl, and $C_1$-$C_4$alkyl.

As an embodiment 6.3, there is provided a compound according to any one of embodiments 1.0-3.0, or a pharmaceutically acceptable salt thereof, wherein $R^5$ is selected from the following structure:

wherein $R^{5d}$ are independently selected from H, halo, halo$C_1$-$C_4$alkyl, and $C_1$-$C_4$alkyl.

As an embodiment 7.0, there is provided a compound according to any one of embodiments 1.0-3.0, or a pharmaceutically acceptable salt thereof, wherein $R^5$ is $C_2$-$C_6$alkyl substituted with 1 or more substituents independently selected from —OH, $C_1$-$C_4$alkoxy, halo, —$NH_2$, —$NH(C_1$-$C_4$alkyl) and —$N(C_1$-$C_4$alkyl)_2$.

As an embodiment 7.1, there is provided a compound according to any one of embodiments 1.0-3.0, or a pharmaceutically acceptable salt thereof, wherein $R^5$ is selected from the following structure:

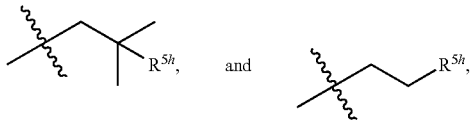

wherein $R^{5h}$ is selected from —$NH_2$, —OH, —$NH(C_1$-$C_4$alkyl) and —$N(C_1$-$C_4$alkyl)_2$.

As an embodiment 8.0, there is provided a compound, or a pharmaceutically acceptable salt thereof, according to any one of embodiments 1.0-7.1, wherein $R^3$ is H.

As an embodiment 9.0, there is provided a compound according to embodiment 1.0, wherein the compound is (R)-2-(5-(hydroxymethyl)-6-((1-methylpiperidin-3-yl)amino)pyridazin-3-yl)-3-methyl-5-(trifluoromethyl)phenol (example 1),
or a pharmaceutically acceptable salt thereof.

As an embodiment 9.1, there is provided a compound according to embodiment 9.0, wherein the compound is a hippurate salt.

As an embodiment 9.2, there is provided a compound according to embodiment 9.0, wherein the compound is a hydrochloride salt.

As an embodiment 9.3, there is provided a compound according to embodiment 9.0, wherein the compound is a hydrate, in particular a hydrate crystalline form, more particularly where the ratio of compound to water molecule is 1:1.

As an embodiment 10.0, there is provided a pharmaceutical composition comprising a therapeutically effective amount of a compound according to any one of embodiments 1.0 to 9.0, or a pharmaceutically acceptable salt thereof, and one or more pharmaceutically acceptable carriers.

As an embodiment 11.0, there is provided a combination comprising a therapeutically effective amount of a compound according to any one of embodiments 1.0 to 9.0, or a pharmaceutically acceptable salt thereof, and one or more therapeutic agents.

As an embodiment 12.0, there is provided the combination according to embodiment 11.0, wherein one or more therapeutic agents are independently selected from farnesoid X receptor (FXR) agonists; anti-steatotics; anti-fibrotics; JAK inhibitors; checkpoint inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase (LTAH4) inhibitors; SGLT2 inhibitors; β2-agonists; anti-inflammatory agents; nonsteroidal anti-inflammatory drugs ("NSAIDs"); acetylsalicylic acid drugs (ASA); regenerative therapy treatments; cystic fibrosis treatments; and atherosclerotic treatment.

As an embodiment 13.0, there is provided a compound according to any one of embodiments 1.0 to 9.0, or a pharmaceutically acceptable salt thereof, or the pharmaceutical composition of embodiment 10.0, or the combination according to embodiment 11.0 or 12.0, for use as a medicament.

As an embodiment 14.0, there is provided a compound according to any one of embodiments 1.0 to 9.0, or a pharmaceutically acceptable salt thereof, for use in the treatment of a disease or disorder in which NLRP3 signaling contributes to the pathology, and/or symptoms, and/or progression, of said disease or disorder.

As an embodiment 15.0, there is provided a compound according to any one of embodiments 1.0 to 9.0, or a pharmaceutically acceptable salt thereof, for use in the manufacture of a medicament for the treatment of a disease or disorder in which NLRP3 signaling contributes to the pathology, and/or symptoms, and/or progression, of said disease or disorder.

As an embodiment 16.0, there is provided a method of treating a disease or disorder in which the NLRP3 signaling contributes to the pathology, and/or symptoms, and/or progression, of said disease or disorder, comprising administering a therapeutically effective amount of a compound according to any one of embodiments 1.0 to 9.0, or a pharmaceutically acceptable salt thereof.

As an embodiment 17.0, there is provided a compound for use according to embodiment 14.0 or 15.0, or the method of treating according to embodiment 16.0, wherein the disease or disorder is selected from inflammasome-related diseases/disorders, immune diseases, inflammatory diseases, autoimmune diseases, or auto-inflammatory diseases, for example, autoinflammatory fever syndromes (e.g. cryopyrin-associated periodic syndrome), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g. acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis).

As an embodiment 18.0, there is provided a method of inhibiting the NLRP3 inflammasome activity in a subject in need thereof, the method comprising administering to a subject in need thereof a therapeutically effective amount of a compound according to any one of embodiments 1.0 to 9.0, or a pharmaceutically acceptable salt thereof.

It was surprisingly found that for compounds of formula (I) where $R^4$ is —$(CH_2)_n$—OH, wherein n is 1, 2, 3 or 4; an increase in hERG $IC_{50}$ was observed compared to the analogues of compound of formula (I) where $R^4$ is $C_1$-$C_4$ alkyl or $C_1$-$C_4$ haloalkyl. This technical effect is demonstrated by the difference in hERG values of example 1 which contains R⁴ is —CH₂—OH and the reference examples 1 and 2. A higher hERG $IC_{50}$ is favorable for the cardiac safety evaluation of compounds.

It was also surprisingly found in *in vivo* experiments that compounds of formula (I) exhibit lower toxicity compared with analogues of compounds of formula (I).

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diastereoisomeric mixtures, and optically pure forms. Optically active (R)- and (S)-stereoisomers may be prepared using chiral synthons or chiral reagents, or resolved using conventional techniques. If the compound contains a disubstituted cycloalkyl, the cycloalkyl substituent may have a cis- or trans-configuration. All tautomeric forms are also intended to be included. The invention is also meant to include any pseudo-asymmetric carbon atom, represented herein as (R)- and (S)-, and which are invariant on reflection in a mirror but are reversed by exchange of any two entities, (PAC 1996, 68, 2193, *Basic terminology of stereochemistry IUPAC recommandations* 1996).

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups, or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, hippuric acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of any general formula (e.g. formula (I) etc.) or example defined herein in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate, or xinafoate salt form. In a particular aspect, the present invention provides compounds of any general formula (e.g. formula (I) etc.) in hippurate or hydrochloride salt form.

In another aspect, the present invention provides compounds of any general formula (e.g. formula (I) etc.) or example defined herein in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

The compounds of the present invention, including salts, hydrates and solvates thereof, may under the appropriate conditions, be isolated in one or more crystalline forms.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Further, incorporation of certain isotopes, particularly deuterium (i.e., ²H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of formula (I). The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Further examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or $^{125}$I labeled compound may be particularly desirable for PET or SPECT studies. Isotopically labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by NLRP3, or (ii) associated with NLRP3 activity, or (iii) characterized by activity (normal or abnormal) of NLRP3; or (2) reduce or inhibit the activity of NLRP3; or (3) reduce or inhibit the expression of NLRP3. In another non-limiting embodiment, the term "a therapeutically effective amount" of a compound of the present invention refers to the amount that when administered to a cell, or a tissue, or a non-cellular biological material, or a medium, is effective to at least partially reduce or inhibit the activity of NLRP3; or at least partially reduce or inhibit the expression of NLRP3.

As used herein, the term "subject" refers to primates (e.g., humans, male or female), dogs, rabbits, guinea pigs, pigs, rats and mice. In certain embodiments, the subject is a primate. In yet another embodiment, the subject is a human.

As used herein, the term "inhibit", "inhibition" or "inhibiting" refers to the reduction or suppression of a given condition, symptom, or disorder, or disease, or a significant decrease in the baseline activity of a biological activity or process. Specifically, inhibiting NLRP3 or inhibiting NLRP3 inflammasome pathway comprises reducing the ability of NLRP3 or NLRP3 inflammasome pathway to induce the production of IL-1 beta and/or IL-18. This can be achieved by mechanisms, including, but not limited to, inactivating, destabilizing, and/or altering distribution of NLRP3.

As used herein, the term "NLRP3" is meant to include, without limitation, nucleic acids, polynucleotides, oligonucleotides, sense and anti-sense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, a subject is "in need of" or "in need thereof" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates, or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) using a chiral adsorbent.

Method of Synthesizing the Compounds of the Invention

The compounds of the present invention may be prepared in accordance with the routes described in the following Scheme and/or the Examples. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. In the following general methods, $R^1$, $R^2$, $R^3$, $R^4$, $R^5$ and halo are as previously defined in the above embodiments, or limited to designations in the Scheme. Unless otherwise stated, starting materials are either commercially available or are prepared by known methods.

Reaction Scheme 1

Compounds of formula (I), as described herein, may be prepared by a reaction sequence shown in Scheme 1 (below), whereby an appropriately substituted 3,6-dihalopyridazine (M1), wherein $R^3$ is as defined herein and $R^6$ may be methyl, is reacted with an appropriate amine (M2), wherein $R^5$ is as defined herein, in the presence of a base, e.g. DIPEA, at low temperature, typically between 0° C. and room temperature, to give 6-halopyridazine-3 amine (M3) which is then reduced, e.g. with LiAlH4 to the 6-halopyridazin-4-alkyl-hydroxy-3 amine (M4). This intermediate is then subjected to a Suzuki-type cross coupling reaction with the appropriate boronate (M5) in the form of a boronic acid or boronic ester (may be prepared as described in WO2020/234715), e.g. 4,4,5,5-tetramethyl-1,3,2-dioxaborolan, using a suitable palladium catalyst, e.g. Pd(PPh3)4, and an aqueous base, typically $Na_2CO_3$ or $NaHCO_3$, in a miscible 20 solvent such as DME or dioxane to provide a compound of formula (I), or a pharmaceutically acceptable salt thereof.

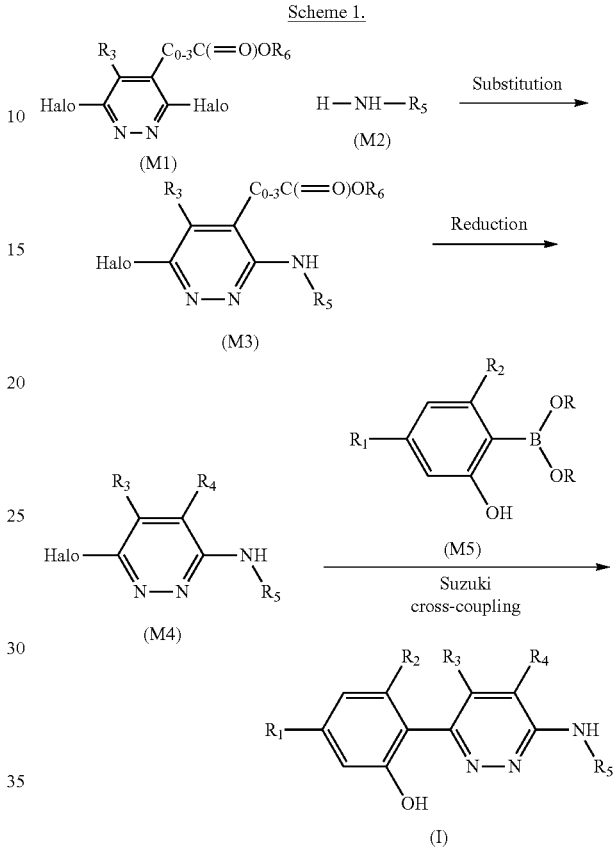

Scheme 1.

The above processes can be extended to prepare a compound of general formula (I) or a pharmaceutically acceptable salt thereof, as described herein. Depending on the starting materials and the selected route, as mentioned in Scheme 1, a skilled person in the art would know how to prepare compound of formula (I), or a pharmaceutically acceptable salt thereof. Certain variants or alternative processes are described herein below in the experimental section.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration) and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) Diluents, e.g., lactose, dextrose, sucrose, mannitol, sorbitol, cellulose and/or glycine;

b) Lubricants, e.g., silica, talcum, stearic acid, its magnesium or calcium salt and/or polyethyleneglycol; for tablets also c) Binders, e.g., magnesium aluminum silicate, starch paste, gelatin, tragacanth, methylcellulose, sodium carboxymethylcellulose and/or polyvinylpyrrolidone; if desired d) Disintegrants, e.g., starches, agar, alginic acid or its sodium salt, or effervescent mixtures; and e) Absorbents, colorants, flavours and sweeteners.

Method of Use of the Invention

There is evidence for a role of NLRP3-induced IL-1 and IL-18 in the inflammatory responses occurring in connection with, or as a result of, a multitude of different disorders (Menu et al, *Clinical and Experimental Immunology,* 2011, 166, 1-15; Strowig et al, *Nature,* 2012, 481, 278-286). NLRP3 mutations have been found to be responsible for a set of rare autoinflammatory diseases known as CAPS (Ozaki et al, *J. Inflammation Research,* 2015, 8, 15-27; Schroder et al, *Cell,* 2010, 140: 821-832; Menu et al, *Clinical and Experimental Immunology,* 2011, 166, 1-15). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β. NLRP3 has also been implicated in a number of autoinflammatory diseases, including pyogenic arthritis, pyoderma gangrenosum and acne (PAPA), Sweet's syndrome, chronic nonbacterial osteomyelitis (CNO), and acne vulgaris (Cook et al, *Eur. J. Immunol.,* 2010, 40, 595-653).

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Braddock et al. *Nat. Rev. Drug Disc.* 2004, 3, 1-10; Inoue et al., Immunology, 2013, 139, 11-18, Coll et al, *Nat. Med.* 2015, 21(3), 248-55; Scott et al, *Clin. Exp. Rheumatol.* 2016, 34(1), 88-93), systemic lupus erythematosus and its complications such as lupus nephritis (Lu et al, *J. Immunol.,* 2017, 198(3), 1119-29), and systemic sclerosis (Artlett et al, *Arthritis Rheum.* 2011, 63(11), 3563-74). NLRP3 has also been shown to play a role in a number of lung diseases including chronic obstructive pulmonary disorder (COPD), asthma (including steroid-resistant asthma), asbestosis, and silicosis (De Nardo et al, *Am. J. Pathol.,* 2014, 184: 42-54; Kim et al. *Am. J. Respir. Crit. Care Med,* 2017, 196(3), 283-97). NLRP3 has also been suggested to have a role in a number of central nervous system conditions, including Multiple Sclerosis (MS), Parkinson's disease (PD), Alzheimer's disease (AD), dementia, Huntington's disease, cerebral malaria, brain injury from pneumococcal meningitis (Walsh et al, *Nature Reviews,* 2014, 15, 84-97; and Dempsey et al. *Brain. Behav. Immun.* 2017, 61, 306-16), intracranial aneurysms (Zhang et al. *J. Stroke and Cerebrovascular Dis.,* 2015, 24, 5, 972-9), and traumatic brain injury (Ismael et al. *J. Neurotrauma.,* 2018, 35(11), 1294-1303). NRLP3 activity has also been shown to be involved in various metabolic diseases including type 2 diabetes (T2D) and its organ-specific complications, atherosclerosis, obesity, gout, pseudo-gout, metabolic syndrome (Wen et al, *Nature Immunology,* 2012, 13, 352-357; Duewell et al, *Nature,* 2010, 464, 1357-1361; Strowig et al, *Nature,* 2014, 481, 278-286), and non-alcoholic steatohepatitis (Mridha et al. *J. Hepatol.* 2017, 66(5), 1037-46). A role for NLRP3 via IL-1 beta has also been suggested in atherosclerosis, myocardial infarction (van Hout et al. *Eur. Heart J.* 2017, 38(11), 828-36), heart failure (Sano et al. *J. Am. Coll. Cardiol.* 2018, 71(8), 875-66), aortic aneurysm and dissection (Wu et al. *Arterioscler. Thromb. Vasc. Biol.,* 2017,37(4), 694-706), and other cardiovascular events (Ridker et al., *N. Engl. J. Med.,* 2017, 377(12), 1119-31).

Other diseases in which NLRP3 has been shown to be involved include: ocular diseases such as both wet and dry age-related macular degeneration (Doyle et al. *Nature Medicine,* 2012, 18, 791-798; Tarallo et al. *Cell* 2012, 149(4), 847-59), diabetic retinopathy (Loukovaara et al. *Acta Ophthalmol.,* 2017, 95(8), 803-8), non-infectious uveitis and optic nerve damage (Puyang et al. *Sci. Rep.* 2016, 6, 20998); liver diseases including non-alcoholic steatohepatitis (NASH) and acute alcoholic hepatitis (Henao-Meija et al, *Nature,* 2012, 482, 179-185); inflammatory reactions in the lung and skin (Primiano et al. *J. Immunol.* 2016, 197(6), 2421-33) including contact hypersensitivity (such as bullous pemphigoid (Fang et al. *J Dermatol Sci.* 2016, 83(2), 116-23)), atopic dermatitis (Niebuhr et al. *Allergy,* 2014, 69(8), 1058-67), Hidradenitis suppurativa (Alikhan et al. *J. Am. Acad. Dermatol.,* 2009,60(4), 539-61), and sarcoidosis (Jager et al. *Am. J. Respir. Crit. Care Med.,* 2015, 191, A5816); inflammatory reactions in the joints (Braddock et al, *Nat. Rev. Drug Disc,* 2004, 3, 1-10); amyotrophic lateral sclerosis (Gugliandolo et al. *Int. J. Mol. Sci.,* 2018, 19(7), E1992); cystic fibrosis (Iannitti et al. *Nat. Commun.,* 2016, 7, 10791); stroke (Walsh et al, *Nature Reviews,* 2014, 15, 84-97); chronic kidney disease (Granata et al. *PLoS One* 2015, 10(3), eoi22272); and inflammatory bowel diseases including ulcerative colitis and Crohn's disease (Braddock et al., *Nat. Rev. Drug Disc,* 2004, 3, 1-10; Neudecker et al. *J. Exp. Med.* 2017, 214(6), 1737-52; Lazaridis et al. *Dig. Dis. Sci.* 2017, 62(9), 2348-56). The NLRP3 inflammasome has been found to be activated in response to oxidative stress. NLRP3 has also been shown to be involved in inflammatory hyperalgesia (Dolunay et al, *Inflammation,* 2017, 40, 366-86).

Activation of the NLRP3 inflammasome has been shown to potentiate some pathogenic infections such as influenza and Leishmaniasis (Tate et al., *Sci Rep.,* 2016, 10(6), 27912-20; Novias et al., *PLOS Pathogens* 2017, 13(2), e1006196).

NLRP3 has also been implicated in the pathogenesis of many cancers (Menu et al, *Clinical and Experimental Immunology,* 2011, 166, 1-15). For example, several previous studies have suggested a role for IL-1 beta in cancer invasiveness, growth and metastasis, and inhibition of IL-1 beta with canakinumab has been shown to reduce the incidence of lung cancer and total cancer mortality in a randomised, double-blind, placebo-controlled trial (Ridker et al. *Lancet.*, 2017, 390(10105), 1833-42). Inhibition of the NLRP3 inflammasome or IL-1 beta has also been shown to inhibit the proliferation and migration of lung cancer cells in vitro (Wang et al. *Oncol Rep.*, 2016, 35(4), 2053-64). A role for the NLRP3 inflammasome has been suggested in myelodysplastic syndromes, myelofibrosis and other myeloproliferative neoplasms, and acute myeloid leukemia (AML) (Basiorka et al. *Blood*, 2016, 128(25), 2960-75. ) and also in the carcinogenesis of various other cancers including glioma (Li et al. *Am. J. Cancer Res.* 2015, 5(1), 442-9), inflammation-induced tumors (Allen et al. *J. Exp. Med.* 2010, 207(5), 1045-56; Hu et al. *PNAS.*, 2010, 107(50), 21635-40), multiple myeloma (Li et al. *Hematology*, 2016 21(3), 144-51), and squamous cell carcinoma of the head and neck (Huang et al. *J. Exp. Clin. Cancer Res.*, 2017, 36(1), 116). Activation of the NLRP3 inflammasome has also been shown to mediate chemoresistance of tumor cells to 5-Fluorouracil (Feng et al. *J. Exp. Clin. Cancer Res.*, 2017, 36(1), 81), and activation of NLRP3 inflammasome in peripheral nerve contributes to chemotherapy-induced neuropathic pain (Jia et al. *Mol. Pain.*, 2017, 13, 1-11). NLRP3 has also been shown to be required for the efficient control of viruses, bacteria, and fungi.

The activation of NLRP3 leads to cell pyroptosis and this feature plays an important part in the manifestation of clinical disease (Yan-gang et al., *Cell Death and Disease*, 2017, 8(2), 2579; Alexander et al., *Hepatology*, 2014, 59(3), 898-910; Baldwin et al., *J. Med. Chem.*, 2016, 59(5), 1691-1710; Ozaki et al., *J. Inflammation Research*, 2015, 8, 15-27; Zhen et al., *Neuroimmunology Neuroinflammation*, 2014, 1(2), 60-65; Mattia et al., *J. Med. Chem.*, 2014, 57(24), 10366-82; Satoh et al., *Cell Death and Disease*, 2013, 4, 644). Therefore, it is anticipated that inhibitors of NLRP3 will block pyroptosis, as well as the release of pro-inflammatory cytokines (e.g. IL-1 beta) from the cell.

The compounds of any general formula (e.g. formula (I), etc.), or a compound according to any one of the preceding embodiments, or a compound according to any one of the exemplified examples (e.g. Example 1 as disclosed herein), in free form or in pharmaceutically acceptable salt form, exhibit valuable pharmacological properties, e.g. NRLP3 inhibiting properties on the NLRP3 pathway, e.g. as indicated by in vitro tests as provided in the next section, and are therefore indicated for therapy or for use as research chemicals, e.g. as tool compounds.

Compounds of the invention may be useful in the treatment of an indication selected from: inflammasome-related disase/disorders, immune diseases, inflammatory diseases, auto-immune diseases, or auto-inflammatory diseases, for example, of diseases, disorders or conditions in which NLRP3 signaling contributes to the pathology, and/or symptoms, and/or progression, and which may be responsive to NLRP3 inhibition and which may be treated or prevented, according to any one of embodiments 1.0 to 18.0, or a compound according to any one of the exemplified examples (e.g. Example 1 as disclosed herein), of the present invention include:

I. Inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity. Examples of inflammation that may be treated or prevented include inflammatory responses occurring in connection with, or as a result of:

(a) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(b) a joint condition such as osteoarthritis, systemic juvenile idiopathic arthritis, adult-onset Still's disease, relapsing polychondritis, rheumatoid arthritis, juvenile chronic arthritis, crystal induced arthropathy (e.g. pseudo-gout, gout), or a seronegative spondyloarthropathy (e.g. ankylosing spondylitis, psoriatic arthritis or Reiter's disease);

(c) a muscular condition such as polymyositis or myasthenia gravis;

(d) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(e) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(f) a vascular condition such as atherosclerosis, Behcet's disease, vasculitides, or Wegener's granulomatosis;

(g) an immune condition, e.g. autoimmune condition, such as systemic lupus erythematosus (SLE), Sjogren's syndrome, systemic sclerosis, Hashimoto's thyroiditis, type I diabetes, idiopathic thrombocytopenia purpura, or Graves disease;

(h) an ocular condition such as uveitis, allergic conjunctivitis, or vernal conjunctivitis;

(i) a nervous condition such as multiple sclerosis or encephalomyelitis;

(j) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium* intracellulare, Pneumocystis carinii pneumonia, orchitis/epidydimitis, legionella, Lyme disease, influenza A, epstein-barr virus, viral encephalitis/aseptic meningitis, or pelvic inflammatory disease;

(k) a renal condition such as mesangial proliferative glomerulonephritis, nephrotic syndrome, nephritis, glomerular nephritis, acute renal failure, uremia, or nephritic syndrome;

(l) a lymphatic condition such as Castleman's disease;
(m) a condition of, or involving, the immune system, such as hyper IgE syndrome, lepromatous leprosy, hemophagocytic histocytosis, familial hemophagocytic lymphohistiocytosis, or graft versus host disease;
(n) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;
(o) a cancer, including those cancers listed herein below;
(p) a burn, wound, trauma, haemorrhage or stroke;
(q) radiation exposure; and/or
(r) obesity; and/or
(s) pain such as inflammatory hyperalgesia.

II. Inflammatory disease, including inflammation occurring as a result of an inflammatory disorder, e.g. an autoinflammatory disease, such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Majeed syndrome, pyogenic arthritis, pyoderma gangrenosum and acne syndrome (PAPA), adult-onset Still's disease (AOSD), haploinsufficiency of A20 (HA2O), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

III. Immune diseases, e.g. auto-immune diseases, such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopeni purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjogren's syndrome, systemic sclerosis a systemic connective tissue disorder, Takayasu's arteritis, temporal arteritis, warm autoimmune hemolytic anemia, Wegener's granulomatosis, alopecia universalis, Beliefs disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, giant cell arteritis, vitiligo or vulvodynia, Hemophagocytic lymphohistiocytosis (HLH), cytokine release syndrome such as T-cell engager therapy (CAR-T or bi/trispecific antibody);

IV. Cancer including lung cancer, renal cell carcinoma, non-small cell lung carcinoma (NSCLC), Langerhans cell histiocytosis (LCH), myeloproliferative neoplasms (MPN), pancreatic cancer, gastric cancer, myelodysplastic syndrome (MDS), leukaemia including acute lymphocytic leukaemia (ALL) and acute myeloid leukaemia (AML), promyelocytic leukemia (APML, or APL), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), Juvenile myelomonocytic leukemia (JMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, plasma cell disorders including Monoclonal gammopathy of undetermined significance (MGUS), smoldering multiple myeloma and active multiple myeloma, multiple myeloma, nasal cavity and paranasal sinuses cancer, nasopharyngeal cancer, neuroblastoma, Mature T and NK neoplasms, non-Hodgkin lymphoma, mature B-cell neoplasms such as non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour, Myeloproliferative neoplasms (MPN) including myelofibrosis, brain tumor including primary brain cancer and brain metastasis, Myelodysplastic/myeloproliferative neoplasms (MDS/MPN), Myeloid/lymphoid neoplasms with eosinophilia and rearrangement of PDGFRA, PDGFRB, or FGFR1, or with PCM1-JAK2, B-lymphoblastic leukemia/lymphoma, T-lymphoblastic leukemia/lymphoma, Histiocytic and dendritic cell neoplasms, Posttransplant lymphoproliferative disorders (PTLD);

V. Infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi or Yersinia pestis), fungal infections (e.g. from Candida or Aspergillus species), protozoan infections (e.g. from Plasmodium, Babesia, Giardia, Entamoeba, Leishmania or Trypanosomes), helminth infections (e.g. from schistosoma, roundworms, tapeworms or flukes), and prion infections;

VI. Central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, multiple sclerosis, and amyotrophic lateral sclerosis;

VII. Metabolic diseases such as type 2 diabetes (T2D), atherosclerosis, obesity, gout, and pseudo-gout;

VIII. Cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, cardiovascular risk reduction (CvRR), and pericarditis including Dressler's syndrome, post-Myocardial Infarction Heart Failure; Atrial fibrillation IX. Respiratory diseases including chronic obstructive pulmonary disorder (COPD), asthma such as allergic asthma and steroid-resistant asthma, asbestosis, silicosis, nanoparticle induced inflammation, cystic fibrosis, and idiopathic pulmonary fibrosis;

X. Liver diseases including non-alcoholic fatty liver disease (NAFLD) and nonalcoholic steatohepatitis (NASH) including advanced fibrosis stages F3 and F4, alcoholic fatty liver disease (AFLD), and alcoholic steatohepatitis (ASH);

XI. Renal diseases including acute kidney disease, hyperoxaluria, chronic kidney disease, oxalate nephropathy, nephrocalcinosis, glomerulonephritis, and diabetic nephropathy;

XII. Ocular diseases including those of the ocular epithelium, age-related macular degeneration (AMD) (dry and wet), uveitis, corneal infection, diabetic retinopathy, optic nerve damage, dry eye, and glaucoma;

XIII. Skin diseases including dermatitis such as contact dermatitis and atopic dermatitis, contact hypersensitivity, sunburn, skin lesions, hidradenitis suppurativa (HS), other cyst-causing skin diseases, and acne conglobata;

XIV. Lymphatic conditions such as lymphangitis, and Castleman's disease;

XV. Psychological disorders such as depression, and psychological stress; schizophrenia, bi-polar disease;

XVI. Graft versus host disease;

XVII. Bone diseases including osteoporosis, osteopetrosis;

XVIII. Blood disease including sickle cell disease;

XVIX. Allodynia including mechanical allodynia; and

XVX. Any disease where an individual has been determined to carry a germline or somatic non-silent mutation in NLRP3.

More specifically the compounds of the invention may be useful in the treatment of an indication selected from: inflammasome-related disase/disorders, immune diseases, inflammatory diseases, auto-immune diseases, or auto-inflammatory diseases, for example, autoinflammatory fever syndromes (e.g., cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g. acute, chronic, Calcium pyrophosphate dihydrate crystal deposition disease (CPPD)), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In particular, compounds of the invention, or a pharmaceutically acceptable salt thereof, may be useful in the treatment of a disease or disorder preferably selected from autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides the use of a compound of any general formula (e.g. formula (I) etc.), or a compound according to any one of the preceding embodiments (e.g. according to any one of embodiments 1.0 to 18.0), or a compound according to any one of the exemplified examples (e.g. Example 1 as disclosed herein), or a pharmaceutically acceptable salt thereof, in therapy. In a further embodiment, the therapy is selected from a disease, which may be treated by inhibition of NLRP3 inflammasome pathway. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g. cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g. acute, chronic), kidney related diseases (e.g. hyperoxaluria, lupus nephritis, Type I/Type II diabetes and related complications (e.g. nephropathy, retinopathy) hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

Thus, as a further aspect, the present invention provides a compound of any general formula (e.g. formula (I) etc.), or a compound according to any one of the preceding embodiments (e.g. according to any one of embodiments 1.0 to 18.0), or a compound according to any one of the exemplified examples (e.g. Example 1 as disclosed herein), or a pharmaceutically acceptable salt thereof, for use in therapy. In a further embodiment, the therapy is selected from a disease, which may be treated by inhibition of NLRP3 inflammasome pathway. In another embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g. cryopyrin-associated periodic syndrome), sickle cell disease, systemic lupus erythematosus (SLE), liver related disease/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g. acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In another aspect, the invention provides a method of treating a disease which is treated by inhibiting NLRP3 comprising administration of a therapeutically effective amount of a compound of any general formula (e.g. formula (I) etc.), or a compound according to any one of the preceding embodiments (e.g. according to any one of embodiments 1.0 to 18.0), or a compound according to any one of the exemplified examples (e.g. Example 1 as disclosed herein), or a pharmaceutically acceptable salt thereof. In a further embodiment, the disease is selected from the afore-mentioned list, suitably inflammasome-related diseases/disorders, immune diseases, inflammatory diseases, auto-immune diseases, or auto-inflammatory diseases, for example, autoinflammatory fever syndromes (e.g. cryopyrin-associated periodic syndrome), sickle cell disease, systemic lupus erythematosus (SLE), liver related diseases/disorders (e.g. chronic liver disease, viral hepatitis, non-alcoholic steatohepatitis (NASH), alcoholic steatohepatitis, and alcoholic liver disease), inflammatory arthritis related disorders (e.g. gout, pseudogout (chondrocalcinosis), osteoarthritis, rheumatoid arthritis, arthropathy e.g. acute, chronic), kidney related diseases (e.g. hyperoxaluria, lupus nephritis, Type I/Type II diabetes and related complications (e.g. nephropathy, retinopathy), hypertensive nephropathy, hemodialysis related inflammation), neuroinflammation-related diseases (e.g. multiple sclerosis, brain infection, acute injury, neurodegenerative diseases, Alzheimer's disease), cardiovascular/metabolic diseases/disorders (e.g. cardiovascular risk reduction (CvRR), hypertension, atherosclerosis, type I and type II diabetes and related complications, peripheral artery disease (PAD), acute heart failure), inflammatory skin diseases (e.g. hidradenitis suppurativa, acne), wound healing and scar formation, asthma, sarcoidosis, age-related macular degeneration, and cancer related diseases/disorders (e.g. colon cancer, lung cancer, myeloproliferative neoplasms, leukemias, myelodysplastic syndromes (MDS), myelofibrosis). In particular, autoinflammatory fever syndromes (e.g. CAPS), sickle cell disease, Type I/Type II diabetes and related complications (e.g. nephropathy, retinopathy), hyperoxaluria, gout, pseudogout (chondrocalcinosis), chronic liver disease, NASH, neuroinflammation-related disorders (e.g. multiple sclerosis, brain infection, acute injury, neurodegenerative diseases, Alzheimer's disease), atherosclerosis and cardiovascular risk (e.g. cardiovascular risk reduction (CvRR), hypertension), hidradenitis suppurativa, wound healing and scar formation, and cancer (e.g. colon cancer, lung cancer, myeloproliferative neoplasms, leukemias, myelodysplastic syndromes (MDS), myelofibrosis).

In a further aspect, the present invention provides a compound of any general formula (e.g. formula (I) etc.), or a compound according to any one of the preceding embodiments (e.g. according to any one of embodiments 1.0 to 18.0), or a compound according to any one of the exemplified examples (e.g. Example 1 as disclosed herein), or a pharmaceutically acceptable salt thereof, useful in the treatment of a disease, disorder or condition substantially or entirely mediated by NLRP3 inflammasome activity, as disclosed herein, and/or NLRP3-induced IL-1 beta, and/or NLRP3-induced IL-18. Some of the diseases, disorders or conditions mentioned herein arise due to mutations in NLRP3, in particular, result in an increased NLRP3 activity.

Combination Product and Combination Therapy of the Invention

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g. powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of any general formula (e.g. formula (I) etc.), or a pharmaceutical acceptable salt thereof, and at least one other therapeutic agent as a combined preparation for simultaneous, separate or sequential use in therapy. In one embodiment, the therapy is the treatment of a disease or condition mediated by NLRP3. Products provided as a combined preparation include a composition comprising the compound of any general formula (e.g. formula (I) etc.), or a pharmaceutically acceptable salt thereof, and the other therapeutic agent(s) together in the same pharmaceutical composition, or the compound of any general formula (e.g. formula (I) etc.), or a pharmaceutically acceptable salt thereof, and the other therapeutic agent(s) in separate form, e.g. in the form of a kit.

In one embodiment, the invention provides a pharmaceutical combination comprising a compound of any general formula (e.g. formula (I) etc.), or a pharmaceutically acceptable salt thereof, or a compound according to any one of the preceding embodiments, or a pharmaceutical acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any general formula (e.g. formula (I) etc.), or a pharmaceutically acceptable salt thereof, or a compound according to any one of the preceding embodiments, or a pharmaceutical acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any general formula (e.g. formula (I) etc.), or a pharmaceutically acceptable salt thereof, for treating a disease or condition mediated by NLRP3, wherein the medicament is prepared for administration with another therapeutic agent. The invention also provides the use of another therapeutic agent for treating a disease or condition mediated by NLRP3 wherein the medicament is administered with a compound of any general formula (e.g. formula (I) etc.), or a pharmaceutically acceptable salt thereof, or a compound according to any one of the preceding embodiments, or a pharmaceutical acceptable salt thereof.

The invention also provides a compound of any general formula (e.g. formula (I) etc.), or a pharmaceutically acceptable salt thereof, or a compound according to any one of the preceding embodiments, or a pharmaceutical acceptable salt thereof, for use in a method of treating a disease or condition mediated by NLRP3, wherein the compound of any general formula (e.g. formula (I) etc.), or a pharmaceutically acceptable salt thereof, or a compound according to any one of the preceding embodiments, or pharmaceutical acceptable salt thereof, is prepared for administration with another therapeutic agent. The invention also provides another therapeutic agent for use in a method of treating a disease or condition mediated by NLRP3, wherein the other therapeutic agent is prepared for administration with a compound of any general formula (e.g. formula (I) etc.), or a pharmaceutically acceptable salt thereof, or a compound according to any one of the preceding embodiments, or pharmaceutical acceptable salt thereof. The invention also provides a compound of any general formula (e.g. formula (I) etc.), or a pharmaceutically acceptable salt thereof, or a compound according to any one of the preceding embodiments, or pharmaceutical acceptable salt thereof, for use in a method of treating a disease or condition mediated by NLRP3, wherein the compound of any general formula (e.g. formula (I) etc.), or a pharmaceutically acceptable salt thereof, or a compound according to any one of the preceding embodiments, or pharmaceutical acceptable salt thereof, is administered with another therapeutic agent. The invention also provides another therapeutic agent for use in a method of treating a disease or condition mediated by NLRP3, wherein the other therapeutic agent is administered with a compound of any general formula (e.g. formula (I) etc.), or a pharmaceutically acceptable salt thereof, or a compound according to any one of the preceding embodiments, or a pharmaceutical acceptable salt thereof.

The invention also provides the use of a compound of any general formula (e.g. formula (I) etc.), or a pharmaceutically acceptable salt thereof, or a compound according to any one of the preceding embodiments (e.g. according to any one of embodiments 1.0 to 18.7), or pharmaceutical acceptable salt thereof, for treating a disease or condition mediated by NLRP3, wherein the patient has previously (e.g. within 24 hours) been treated with another therapeutic agent. The invention also provides the use of another therapeutic agent for treating a disease or condition mediated by NLRP3 inflammasome pathway, wherein the patient has previously (e.g. within 24 hours) been treated with a compound of any general formula (e.g. formula (I) etc.), or a pharmaceutically acceptable salt thereof, or a compound according to any one of the preceding embodiments, or a pharmaceutical acceptable salt thereof.

In one embodiment, the other therapeutic agent is a therapeutic agent useful in the treatment of inflammasome-related diseases/disorders, immune diseases, inflammatory diseases, auto-immune diseases, or auto-inflammatory diseases, as disclosed herein.

In one embodiment, the other therapeutic agent useful in the combination therapy is selected from farnesoid X receptor (FXR) agonists; anti-steatotics; anti-fibrotics; JAK inhibitors; checkpoint inhibitors; chemotherapy, radiation therapy and surgical procedures; urate-lowering therapies; anabolics and cartilage regenerative therapy; blockade of IL-17; complement inhibitors; Bruton's tyrosine Kinase inhibitors (BTK inhibitors); Toll Like receptor inhibitors (TLR7/8 inhibitors); CAR-T therapy; anti-hypertensive agents; cholesterol lowering agents; leukotriene A4 hydrolase LTA4H) inhibitors; SGLT2 inhibitors; β2-agonists; anti-inflammatory agents; nonsteroidal anti-inflammatory drugs ("NSAIDs"); acetylsalicylic acid drugs (ASA) including aspirin; paracetamol; regenerative therapy treatments; cystic fibrosis treatments; and atherosclerotic treatment.

Suitable leukotriene A4 hydrolase (LTA4H) inhibitors for use in the combination include, but are not limited to, compounds disclosed in WO2015/092740, in particular (S)-3-amino-4-(5-(4-((5-chloro-3-fluoropyridin-2-yl)oxy)phenyl)-2H-tetrazol-2-yl)butanoic acid (LYS006), and compounds disclosed in WO2022/219546.

Suitable sodium-dependent glucose transporter 2 (SGLT2) inhibitors for use in the combination include, but are not limited to, compounds disclosed in U.S. Pat. No. 8,163,704, WO2011/048112, WO2011/048148, or in WO2010/128152.

Suitable β2-agonists for use in the combination include, but are not limited to, arformoterol, bambuterol, bitolterol, broxaterol, carbuterol, clenbuterol, dopexamine, fenoterol, formoterol, hexoprenaline, ibuterol, Isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, GSK-159797, GSK-678007, GSK-642444, GSK-159802, HOKU-81, (−)-2-[7 (S)-[2(R)-Hydroxy-2-(4-hydroxyphenyl)ethylamino]-5, 6,7, 8-tetrahydro-2-naphthyloxy]-N,N-di methylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(1-fluoro-4-hydroxyphenyl)-2-[4-(1-benzimidazolyl)-2-methyl-2-butylamino]ethanol, 1-[3-(4-methoxybenzyl amino)-4-hydroxyphenyl]-2-[4(1-benzimidazolyl)-2-methyl-2-butylamino]ethanol, 1-[2H-5-hydroxy-3-oxo-4H-1,4-benzoxazin-8-yl]-2-[3-(4-N,N-dimethyl aminophenyl)-2-methyl-2-propyl amino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4benzoxazin-3-(4H)-one, 1-(4-amino-3-chloro-5trifluoromethylphenyl)-2-tert-butylamino) ethanol, 1-(4-ethoxy carbonylamino-3-cyano-5-fluoro phenyl)-2-(tert-butylamino)ethanol, and combinations thereof, each of which is optionally in the form of a racemate, enantiomer, diastereomer, or mixtures thereof, and also optionally in the form of a pharmacologically-compatible acid addition salt.

Suitable cartilage regenerative therapy for use in the combination includes, but are not limited to, ANGPTL3 peptidomimetics disclosed in WO2014/138687, or a chondrogenesis activator disclosed in WO2015/175487.

Suitable checkpoint inhibitors for use in the combination include, but are not limited to, anti-PD1 inhibitors, anti-LAG-3 inhibitors, anti-TIM-3 inhibitors, anti-PDL1 inhibitors. Suitable anti-PD1 inhibitors, include, but are not limited to, an antibody molecule disclosed in WO2015/112900. Suitable anti-LAG-3 inhibitors, include, but are not limited to, an antibody molecule disclosed in WO2015/138920. Suitable anti-TIM-3 inhibitors include, but are not limited to, an antibody molecule disclosed in WO2015/117002. Suitable anti-TIM-3 inhibitors include, but are not limited to, an antibody molecule disclosed in WO2015/117002. Suitable anti PDL1 inhibitors include, but are not limited to, an antibody molecule disclosed in WO2016/061142.

Suitable Toll Like receptor inhibitors (TLR7/8 inhibitors) for use in the combination include, but are not limited to, a compound disclosed in WO2018/04081.

Suitable FXR agonists for use in the combination include, but are not limited to, obeticholic acid (so called OCA, Intercept), GS9674, elafibranor (GFT505), GW4064, UPF987, FXR-450, fexaramine, methylcolate, methyl deoxycholate, 5β-cholanic acid, 5β-chloanic acid 7α, 12α diol, NIHS700, marchantin A, marchantin E, MFA-1 INT767 (also called 6α-ethyl-CDCA disclosed in WO2014/085474), MET409 (Metacrine), EDP-305 (Enanta), 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid (also known under the name Tropifexor), or a pharmaceutically acceptable salt thereof, or a compound disclosed in WO2012/087519, or a compound disclosed in WO2015/069666.

Suitable JAK inhibitors for use in the combination include, but are not limited to Ruxolitinib.

Suitable NSAIDs for use in the combination include, but are not limited to, Aceclofenac, acemetacin, acetylsalicylic acid, alclofenac, alminoprofen, amfenac, Ampiroxicam, Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac, Enfenaminsaure, Etersalat, etodolac, etofenamate, etoricoxib, Feclobuzon, felbinac, fenbufen, fenclofenac, fenoprofen, fentiazac, Fepradinol, Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

Suitable BTK inhibitors include for example Ibrutinib, Acalabrutinib (ACP-196), Evobrutinib; Fenebrutinib; Tirabrutinib (ONO-4059, GS-4059); Zanubrutinib (BGB-3111), Spebrutinib (CC-292, AVL-292), Poseltinib (HM-71224, LY3337641), Vecabrutinib (SNS-062), BMS-986142; BMS986195; PRN2246; PRN1008, M7583, CT1530, BIIBO68, AC-0058TA, ARQ-531, TAK-020, TG1701 or a compound described in WO2015/079417, WO2015/083008, WO2015/110923, WO2014/173289, WO2012/021444, WO2013/081016, WO2013/067274, WO2012/170976, WO2011/162515, US2017/119766, WO2016/065226, U.S. Pat. No. 9,688,676, WO2016/201280, WO2017/059702, U.S. Pat. No. 9,630,968, US2014/0256734, WO2017118277, WO2014/039899, WO/16/105531, WO2018/005849, WO2013/185082 or in J. Med. Chem., 2016, 59(19), 9173-9200. Of particular interest, BTK inhibitors include compound of example 31 described in WO2014/039899, compound of the following structure:

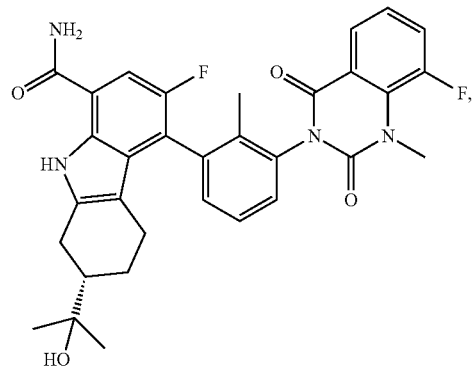 [SMILES: Cc1c(-c2c(F)cc(C(N)=O)c3[nH]c4c(c23)CC[C@H](C(C)(C)O)C4)cccc1-n1c(=O)c2cccc(F)c2n(C)c1=O]

described as compound 14f in Journal of Medicinal Chemistry, 2016, 59(19), 9173-9200; compound of example 2 described in US2017/119766, compound of example 223 described in WO2016/065226 which is:

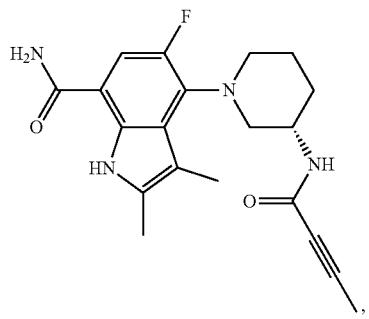 [SMILES: CC#CC(=O)N[C@H]1CCCN(c2c(F)cc(C(N)=O)c3[nH]c(C)c(C)c23)C1]

or compound 1 described in WO2016/201280, compound 1 described in WO2017/059702, or compound 1 described in WO2017/118277; or a pharmaceutically acceptable salt thereof. Of other particular interest, BTK inhibitors include a compound described in WO2015/079417, for example a compound selected from N-(3-(5-((1-Acryloylazetidin-3-yl)oxy)-6-aminopyrimidin-4-yl)-5-fluoro-2-methylphenyl)-4- cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide (Remibrutinib); N-(3-(6-Amino-5-(2-(N-methylpropiol amido)ethoxy)pyrimidin-4-yl)-5-fluoro-2-methylphenyl)-4-cyclopropyl-2-fluoro benzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoro ethyl)acrylamido)ethoxy)pyrimidin-4-yl)-5-fluoro-2-methylphenyl)-4-cyclopropyl-2-fluoro benzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclo propyl-2-fluorobenzamide and N-(3-(6-Amino-5-(3-(N-methylacrylamido)propoxy)pyrimidin-4-yl)-5-fluoro-2-methylphenyl)-4-cyclo propyl-2-fluorobenzamide; or a pharmaceutically acceptable salt thereof.

EXAMPLES

Exemplification of the Invention

Figure 1:
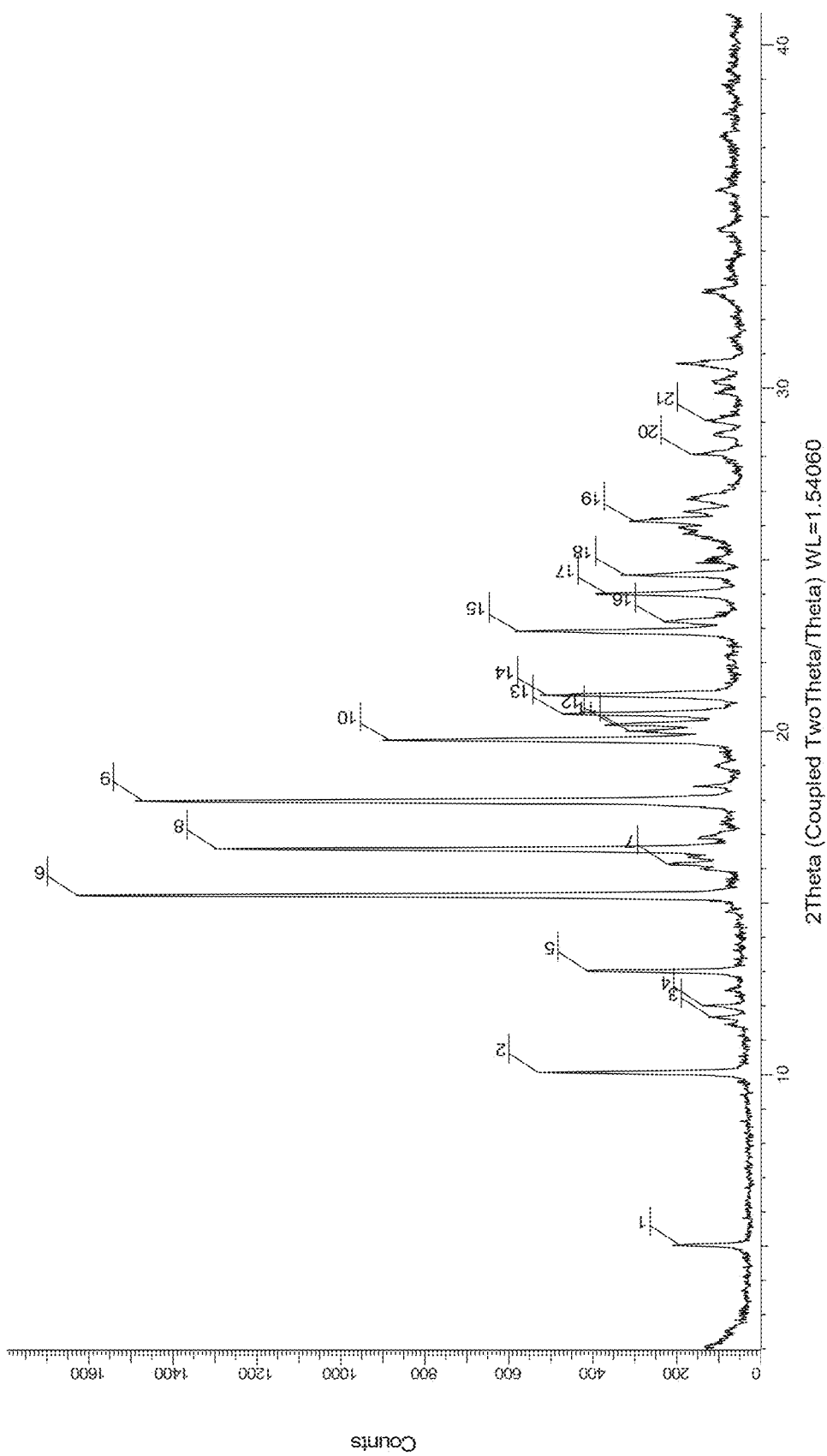
FIG. 1 shows the X-ray powder diffraction pattern of form $H_A$.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof, which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (2014) Protective Groups in Organic Synthesis, 5th edition, John Wiley & Sons). These groups are removed at a convenient stage of the compound synthesis using methods that are readily apparent to those skilled in the art.

Unless otherwise noted, reagents and solvents were used as received from commercial suppliers.

The chemical names were generated using ChemBioDraw Ultra v14 from CambridgeSoft.

Temperatures are given in degrees Celsius. If not mentioned otherwise, all evaporations are performed under reduced pressure, typically between about 15 mm Hg and 100 mm Hg (=20–133 mbar). The structure of final products, intermediates and starting materials is confirmed by standard analytical methods, e.g., microanalysis and spectroscopic characteristics, e.g., MS, IR, NMR. Abbreviations used are those conventional in the art.

Abbreviations

AA Acetic acid
ACN Acetonitrile
CPME Cyclopentyl methyl ether
DCM Dichloromethane
DMSO Dimethylsulfoxide
EtOAc Ethyl acetate
EtOH Ethanol
FA Formic acid
G Gram(s)
H Hour(s)
Hz/MHz Hertz/Mega Hertz
IC50 Half maximal inhibitory concentration
IL-1β Interleukin 1 beta
IPA Isopropyl alcohol
LC-MS Liquid chromatography—mass spectrometry
LlAlH4 Lithium aluminum (IV) hydride
M Molar
MCC Microcrystalline cellulose
MEK Methyl ethyl ketone
MeOH Methanol
min Minute
mL/L Millilitre/Litre
Mmol Millimol
MTBE Methyl tert-butyl ether
NMR Nuclear magnetic resonance
Ppm Parts per million
Pd(PPh3)4 Tetrakis(triphenylphosphine)palladium(0)
RP Reverse phase
Rpm Revolutions per minute
RPMI Roswell Park Memorial Institute
RT Room temperature—in Celsius
Rt Retention time Rochelle's salt Sodium potassium tartrate tetrahydrate
TEA Triethylamine
TEAC Tetraethylammonium chloride
TFA Trifluoroacetic acid
THF Tetrahydrofuran
TNF-α Tumor necrosis factor-α
UPLC Ultra performance liquid chromatography Analytical Details NMR: Measurements were performed on a Bruker Ascend™ (400 MHZ) spectrometer or Bruker Ultrashield™ 400 (400 MHZ) or Bruker Ascend™ (400 MHZ) or Bruker cryo system (600 MHZ) spectrometer using or not using tetramethylsilane (TMS) as an internal standard. Chemical shifts (δ) are reported in ppm downfield from TMS, spectra splitting pattern are designated as singlet (s), doublet (d), triplet (f), quartet (q), quintet (quint), septet (sept), multiplet, unresolved or overlapping signals (m), broad signal (br). Deuterated solvents are given in parentheses and have a chemical shifts of dimethyl sulfoxide (0 2.50 ppm), methanol (0 3.31 ppm), chloroform (0 7.26 ppm), or other solvent as indicated in NMR spectral data.

UPLC-MS (method 1): System: Waters Acquity UPLC with Waters SQ detector.

Column: CORTECS C18 2.7 μm, 2.1×50 mm column temperature: 80° C.

Gradient: from 1 to 50% B in 1.4 min; 50 to 98% B in 0.3 min, A=water+4.76% isopropanol+0.05% FA+3.75 mM AA, B=isopropanol+0.05% FA, flow: 1.0 mL/min.

UPLC-MS basic: System: Waters Acquity UPLC with Waters SQ detector.

Column: Type: XBridge® BEH™ C18 2.5 μm, 2.1×50 mm column temperature: 80° C.

Gradient: from 2 to 98% B in 1.4 min, A=water+5 mM NH$_4$OH, B=acetonitrile+5 mM NH$_4$OH, flow: 1.0 mL/min.

UPLC-MS (method 2): System: Waters Acquity UPLC with Waters SQ detector.

Column: Waters Acquity UPLC BEH C18, column temperature: 40° C.

Gradient: from 5% to 95% B in 8 min; 95% B kept for 2 min, A=95% water+5% acetonitrile+0.05% TFA, B=5% water+95% acetonitrile+0.05% TFA, flow: 0.5 mL/min.

Mass spectrometry results are reported as the ratio of mass over charge.

Preparative Methods

Flash Column Chromatography Systems:
System 1: Teledyne ISCO, CombiFlash Rf.
Columns: pre-packed RediSep Rf cartridges.
Samples were typically adsorbed on Isolute.
System 2: Isolera One Biotage Chromatography System
Columns: pre-packed Biotage SNAP Cartridge All starting materials, building blocks, reagents, acids, bases, dehydrating agents, solvents, and catalysts utilized to synthesize the compounds of the present invention are either commercially available or can be produced by organic synthesis methods known to one of ordinary skill in the art.

Synthesis of Intermediates

Intermediate 1: Methyl (R)-6-chloro-3-((1-methylpiperidin-3-yl)amino)pyridazine-4-carboxylate

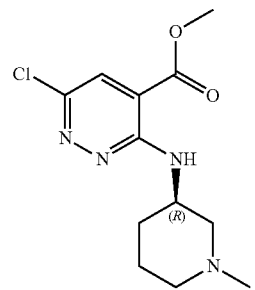

To a solution of methyl 3,6-dichloropyridazine-4-carboxylate (3.0 g, 14.49 mmol) in dry THF (20 mL), were added triethylamine (3.03 mL, 21.74 mmol) and (R)-1-methylpiperidin-3-amine (1.99 g, 17.39 mmol) at RT. The mixture was warmed to 60° C. and stirred for 6 days. The reaction mixture was diluted with EtOAc and brine was added. The phases were separated, the aqueous layer was extracted with EtOAc, the combined organic layers were dried over Na$_2$SO$_4$, filtered and evaporated to dryness. The crude product was purified by column chromatography on silica gel using DCM and MeOH (0 to 10%) to afford the title compound as an orange solid.

UPLC/MS (method 1): Rt=0.28 min; MS m/z 285.2 [M+H]$^+$. $^1$H NMR (400 MHZ, DMSO-d$_6$): δ (ppm) 7.85 (s, 1H), 4.43-4.26 (m, 1H), 3.88 (s, 3H), 3.18-2.99 (m, 2H), 2.41-2.29 (m, 2H), 2.21 (s, 3H), 1.72-1.56 (m, 3H), 1.57-1.46 (m, 1H).

Intermediate 2: (R)-(6-chloro-3-((1-methylpiperidin-3-yl) amino)pyridazin-4-yl)methanol

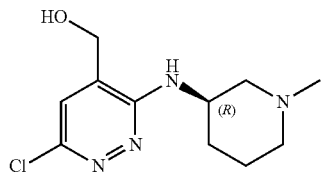

LiAlH$_4$ (1M in THF, 1.84 mL, 1.84 mmol) was added to a solution of Intermediate 1 (0.5 g, 1.76 mmol) in dry THF (10 mL) at −10° C. under a nitrogen atmosphere. The mixture was stirred for 40 min at −10° C. before being quenched by dropwise addition of a saturated solution of Rochelle's salt and stirred for 15 min at RT before EtOAc was added. The phases were separated, the aqueous layer was extracted with EtOAc (twice). The combined organic layers were dried over Na$_2$SO$_4$, filtered and evaporated to provide an oil. The crude product was purified by column chromatography on silica gel using DCM and MeOH (5% aq. NH$_4$OH) from 0 to 20% to afford the title compound.

UPLC/MS basic method: Rt=0.58 min; MS m/z 257.3 [M+H]$^+$. $^1$H NMR (400 MHZ, DMSO-d$_6$) δ (ppm) 7.30 (s, 1H), 6.03 (d, 1H), 5.68-5.59 (m, 1H), 4.41-4.32 (m, 2H), 4.22-4.09 (m, 1H), 2.85-2.75 (m, 1H), 2.56-2.50 (m, 1H), 2.16 (s, 3H), 2.06-1.88 (m, 2H), 1.83-1.74 (m, 1H), 1.71-1.62 (m, 1H), 1.57-1.46 (m, 1H), 1.45-1.32 (m, 1H).

Intermediate 3:
2-Iodo-3-methyl-5-(trifluoromethyl)phenol (may be Prepared as Described in WO2020/234715, Int B007)

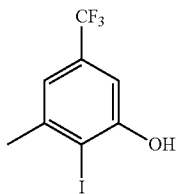

To an ice-cold solution of 3-methyl-5-(trifluoromethyl)phenol (13.03 g, 74 mmol) in 370 mL of toluene was added NaH (60% dispersion in mineral oil, 5.92 g, 148 mmol). The suspension was stirred at 0° C. for 30 minutes, then iodine (18.77 g, 74 mmol) was slowly added in portions and stirring was continued for 3 h. The mixture was diluted with water, acidified with 2 M HCl to pH=5 and extracted with EtOAc. The organic layer was washed with brine, dried over Na$_2$SO$_4$, filtered and evaporated. The crude was purified by column chromatography on silica gel (220 g) using cyclohexane and EtOAc (from 5% to 100%) to afford the title compound as a yellow oil. $^1$H NMR (400 MHZ, CDCl$_3$) δ (ppm) 7.08-7.04 (m, 2H), 5.74 (s, 1H), 2.50 (s, 3H).

Intermediate 4: 3-methyl-2-(4,4,5,5-tetramethyl-1,3,2-dioxaborolan-2-yl)-5-(trifluoromethyl)phenol (may be Prepared as Described in WO2020/234715, Int B010)

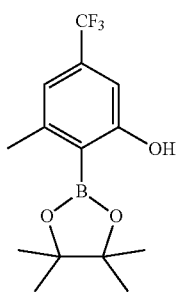 [SMILES: Cc1cc(C(F)(F)F)cc(O)c1B1OC(C)(C)C(C)(C)O1]

(1) 1-(ethoxymethoxy)-2-iodo-3-methyl-5-(trifluoromethyl)benzene

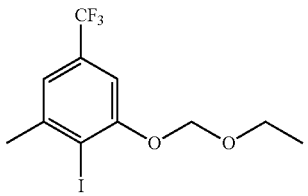 [SMILES: CCOCOc1cc(C(F)(F)F)cc(C)c1I]

(Chloromethoxy)ethane (3.35 g, 35.50 mmol) was added dropwise to a white suspension of 2-iodo-3-methyl-5-(trifluoromethyl)phenol (Intermediate 3, 8.50 g, 28.10 mmol) and Cs$_2$CO$_3$ (9.17 g, 28.10 mmol) in 30 mL of dry DMF. The reaction mixture was stirred at RT for 2 h before it was evaporated to dryness. The crude was purified by column chromatography on silica gel using cyclohexane and EtOAc (from 0% to 5%) to afford the title compound.

(2) 2-(2-(Ethoxymethoxy)-6-methyl-4-(trifluoromethyl) phenyl)-4,4,5,5-tetramethyl-1,3,2-dioxaborolane

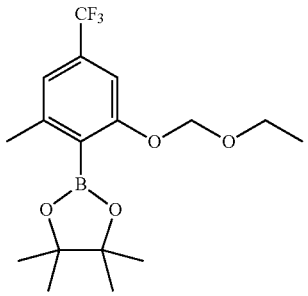 [SMILES: CCOCOc1cc(C(F)(F)F)cc(C)c1B1OC(C)(C)C(C)(C)O1]

A solution of 1-(ethoxymethoxy)-2-iodo-3-methyl-5-(trifluoromethyl)benzene (10 g, 27.80 mmol), 4,4,5,5-tetramethyl-[1,3,2]dioxaborolane (20.15 mL, 139 mmol) and NEt$_3$ (28.6 mL, 205 mmol) in 60 mL of 1,4-dioxane was purged with nitrogen. Pd(OAc)$_2$ (0.81 g, 3.61 mmol) and biphenyl-2-yl-dicyclohexylphosphane (2.33 g, 6.66 mmol) were added and the mixture was stirred at 80° C. for 18 h. It was then cooled to RT, diluted with EtOAc and washed with saturated NH$_4$Cl, water and brine. The organic layer was dried over Na$_2$SO$_4$, filtered and evaporated. The crude product was purified by column chromatography on silica gel using cyclohexane and CH$_2$Cl$_2$ (from 0% to 20%) to afford the title compound.

(3) 3-Methyl-2-(4,4,5,5-tetramethyl-1,3,2-dioxaborolan-2-yl)-5-(trifluoromethyl)phenol TFA (44.9 mL, 583 mmol) was slowly added to a solution of 2-(2-(Ethoxymethoxy)-6-methyl-4-(trifluoromethyl)phenyl)-4,4,5,5-tetramethyl-1,3,2-dioxaborolane. (7.00 g, 19.43 mmol) in 250 mL of CH$_2$Cl$_2$ at 0° C. The reaction mixture was stirred at 0° C. for 20 min and then evaporated. The resulting oil was purified by column chromatography on silica gel using cyclohexane and CH$_2$Cl$_2$ (from 0% to 100%) to afford the title compound. $^1$H NMR (400 MHZ, DMSO-d$_6$) δ (ppm) 9.80 (s, 1H), 6.92 (s, 1H), 6.82 (s, 1H), 2.30 (s, 3H), 1.30 (s, 12H).

Synthesis of Examples

Example 1: (R)-2-(5-(hydroxymethyl)-6-((1-methylpiperidin-3-yl)amino)pyridazin-3-yl)-3-methyl-5-(trifluoromethyl)phenol

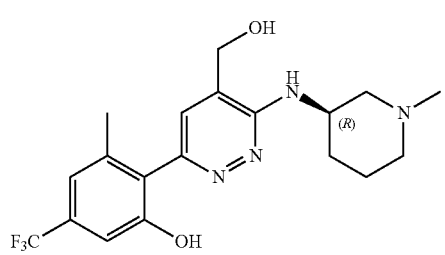

(R)-(6-chloro-3-((1-methylpiperidin-3-yl)amino)pyridazin-4-yl)methanol (Intermediate 2, 0.25 g, 0.83 mmol), 3-methyl-2-(4,4,5,5-tetramethyl-1,3,2-dioxaborolan-2-yl)-5-(trifluoromethyl)phenol (Intermediate 4, 0.3 g, 0.99 mmol) and a 2M aqueous solution of $Na_2CO_3$ (1.2 mL) were suspended in dioxane (7 mL) and the mixture purged with nitrogen for 5 min. $Pd(PPh_3)_4$ (47.8 mg, 0.041 mmol) was added and the mixture stirred at 120° C. for 1 h under microwave irradiation. The reaction mixture was diluted with DCM and brine and the phases were separated. The aqueous layer was extracted with DCM, the combined organic layers were dried/filtered over an Isolute phase separator, evaporated to dryness. The residue was purified by column chromatography on silica gel using DCM and MeOH (5% aq. $NH_4OH$) from 0% to 20% to afford a pale yellow solid. The solid was dissolved in MeOH at 60° C., the volume was reduced and the solution allowed to cool to RT overnight. The MeOH supernatant was removed and the resulting crystals were dried under high vacuum to afford the title compound.

UPLC/MS (method 1): Rt=0.61 min; MS m/z 397.4 M+H]$^+$. $^1$H NMR (400 MHZ, DMSO-$d_6$) δ (ppm) 10.18 (br s, 1H), 7.22 (s, 1H), 7.13-7.02 (m, 2H), 5.98-5.87 (m, 1H), 5.61-5.49 (m, 1H), 4.47-4.37 (m, 2H), 4.34-4.23 (m, 1H), 2.89-2.79 (m, 1H), 2.57-2.43 (m obscured by DMSO, 1H), 2.19 (s, 3H), 2.12 (s, 3H), 2.09-1.94 (m, 2H), 1.86-1.77 (m, 1H), 1.75-1.65 (m, 1H), 1.62-1.39 (m, 2H).

Alternative Synthesis of Example 1

Example 1 may be prepared according to the following scheme.

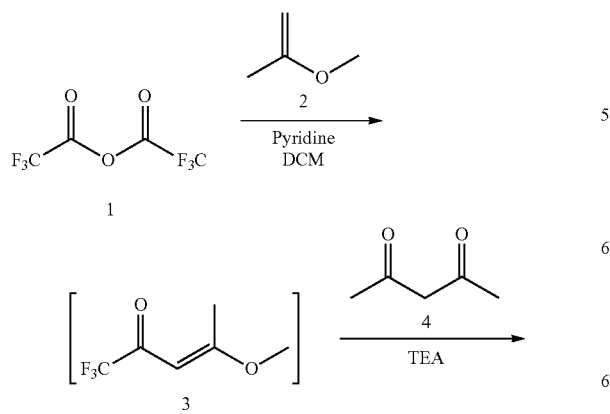

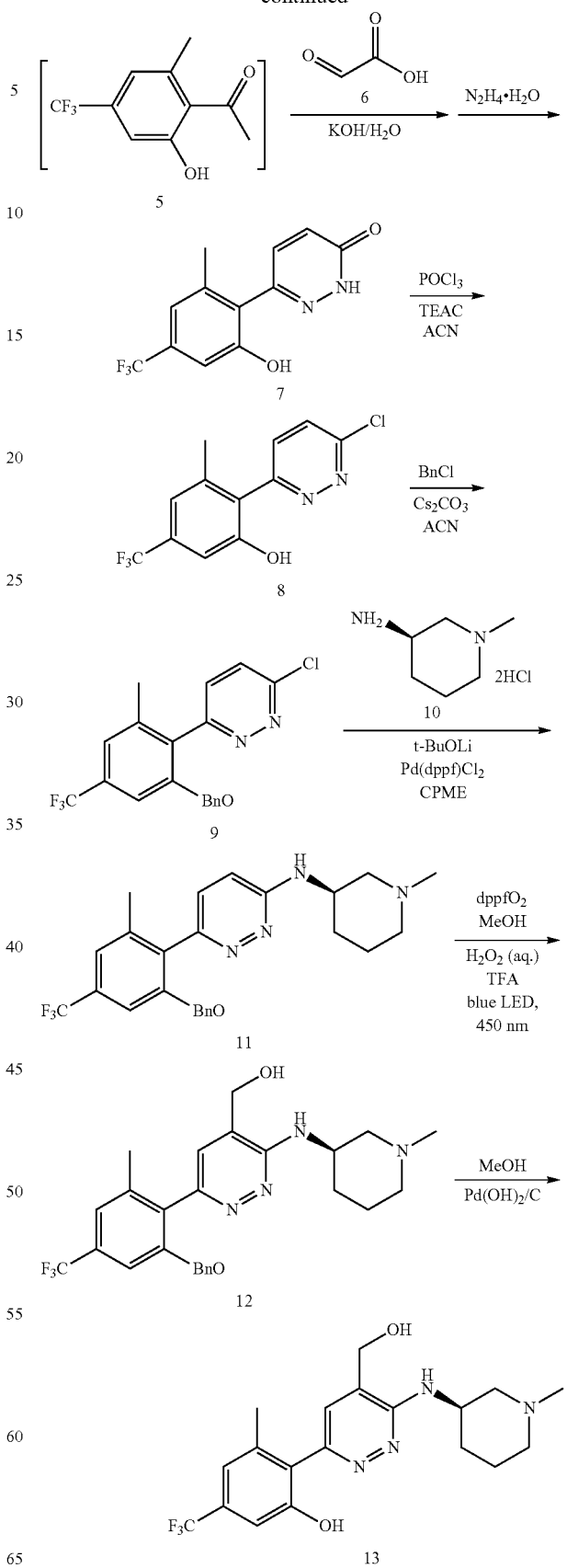

Step 1

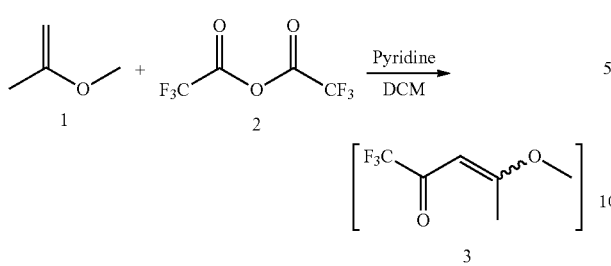

Compound 1 (41.2 g, 571.3 mmol, 1.2 eq.), pyridine (37.7 g, 476.6 mmol, 1 eq.) and DCM (60 g) were charged to a reactor 1. Reactor 1 was stirred for 1 h at a temperature range of 20-30° C. Compound 2 (100 g, 476.1 mmol 1 eq.) and DCM (600 g) was charged to a reactor 2. Cool reactor 2 to a temperature range of −10~0° C. The mixture of reactor 1 was added dropwise into reactor 2 and reactor 1 was rinsed with MTBE (150 g) and the whole stirred for 1-3 h at a temperature in the range −10~0° C. Then reactor 2 was adjusted to 20-30° C. and the whole stirred for 17-20 h. 200 g 0.1 N HCl (aqueous) was added into reactor 2 dropwise at a temperature range of 20~30° C. The aqueous and organic layers were separated and the organic layer collected into reactor 2. 200 g 7% NaHCO₃ (aqueous) was added into reactor 2 to adjust the pH to 6-7 at a temperature 20~30° C. The organic layer was collected and washed with water (200 g) and then concentrated under vacuum below 40° C. to obtain the crude compound 3 as an oil.

$^1$H NMR (300 MHZ, CDCl₃) δ 5.67 (s, 1H), 3.78 (s, 3H), 2.40 (s, 3H).

Step 2

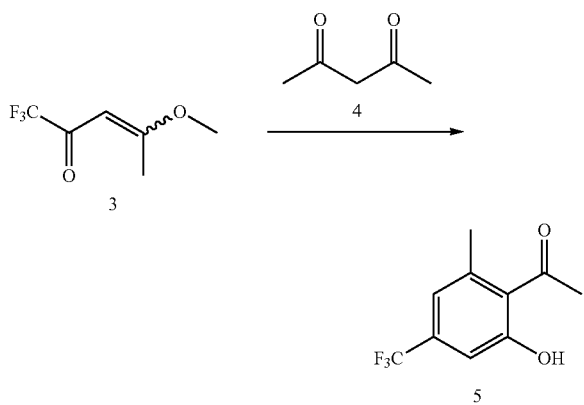

Compound 3 (100 g, 594.8 mmol, 1.0 eq.), TEA (60.2 g, 594.9 mmol, 1 eq.) and 4 (297.8 g, 2.974 mol, 5 eq.) were charged to reactor 1. Reactor 1 was stirred for 20 h at a temperature range of 90-100° C. The mixture was cooled to a temperature range of 15-25° C. after the reaction completed. Water (200 g) and toluene (450 g) was added to the reaction mixture. 10% citric acid (aq.) was charged dropwise into reactor 1 to adjust the pH to between 6-7 at a temperature range of 20-30° C. The aqueous and organic layers were separated and the organic layer was washed with 10% NaCl (aq.) (200 g) twice. The organic layer was collected and concentrated under vacuum below 70° C. to obtain the crude product as oil.

$^1$H NMR (300 MHZ, CDCl₃) δ 11.91 (s, 1H), 7.11 (s, 1H), 6.98 (s, 1H), 2.71 (s, 3H), 2.66 (s, 3H).

LCMS (m/z, ESI) calc $C_{10}H_{10}F_3O_2^+$ [M+H]⁺: 219.0

Step 3

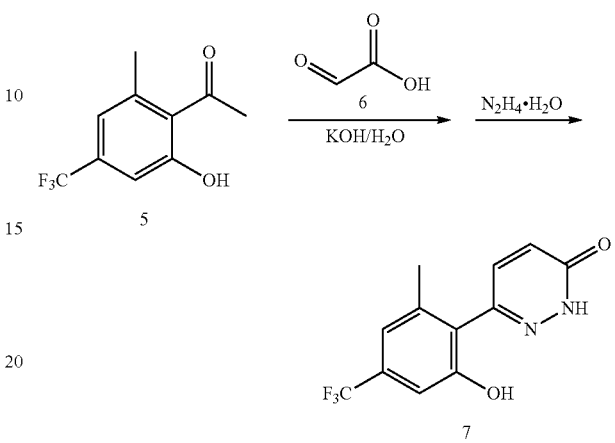

Compound 5 (100 g, 458.3 mmol, 1.0 eq.) and 2M KOH (aq.) (800 g) were charged to a reactor 1 and the reaction mixture stirred for 1 h at a temperature range of 20-30° C.

Compound 6 (212.1 g, 2.86 mol, 6.2 eq.) and water (410 g) were charged to a reactor 2. 733 g 2M KOH (aq.) was added into reactor 1 at a temperature range of −5-0° C. and stirred for 1 h. The aqueous layer of reactor 1 was added slowly into reactor 2 at a temperature range of −5-0° C. The reaction mixture was stirred for another 20 h at a temperature range of −5-0° C. The pH was adjusted with acetic acid to 9-10 at a temperature range of −5-5° C. DCM (768 g) was charged into reactor 2 and the organic layer separated and collected. The pH was further adjusted to between 4 and 5 with acetic acid. The pH was then adjusted to between 8 and 9 with NH₃·H₂O at a temperature range of 10-20° C. N₂H₄·H₂O (80% w/w, 71.7 g) was charged into the mixture at a temperature range of 10-20° C. The temperature of the mixture was then adjusted to a temperature between 90 and 100° C. and the whole stirred for 20 h. The mixture was cooled to a temperature range of 30-40° C. and the pH adjusted to between 6 and 7 with acetic acid. 2-MeTHF (800 g) was added into the mixture and the organic layer collected and filtered through silica gel pad. The solution was concentrated to 600-700 g and then heptane (680 g) was added dropwise at a temperature of 40-50° C. The mixture was cooled to 15-25° C. over 5 h and filtered after stirring for another 3 h at a temperature of 15-25° C. The wet cake was slurried with MeOH (600 g) and water (800 g) at a temperature of 40-50° C. and the mixture was then cooled to a temperature of 15-25° C. over 5 h and then stirred for another 3 h. The wet cake was dried at a temperature of 40-50° C. for 20 h to obtain product 7 42.1 g as white solid.

$^1$H NMR (300 MHZ, DMSO-d₆) δ 13.21 (br s, 1H), 10.38 (br s, 1H), 7.41 (d, J=9.7 Hz, 1H), 7.10 (d, J=13.1 Hz, 2H), 6.94 (d, J=9.7 Hz, 1H), 2.19 (s, 1H).

LCMS (m/z, ESI) UPLC-MS (method 2) calc $C_{12}H_{10}F_3N_2O_2^+$ [M+H]⁺ 271.1

Step 4

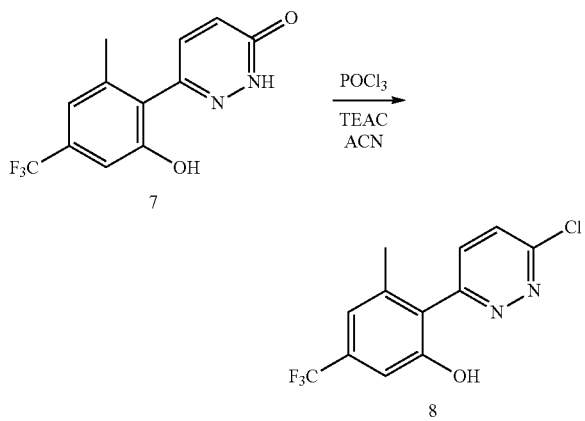

Compound 7 (17.4 g, 64.5 mmol, 1.0 eq.), TEAC (21.4 g, 129.1 mmol 2 eq.), POCl$_3$ (14.8 g, 96.8 mmol, 1.5 eq.) and ACN (70 g) was charged to a reactor 1. The mixture was stirred for 17 h at a temperature of 15-25° C. After the reaction had completed, water (280 g) was charged into reactor 2 and the whole heated to 50° C. The mixture was slowly transferred from reactor 1 into reactor 2 at a temperature of 45-55° C. After stirring the reaction mixture for 16 h at a temperature of 45-55° C., the mixture was filtered and the wet cake washed with water (40 mL). The wet cake was charged into reactor 2, water was added (140 g) and the pH adjusted to between 7 and 8 with 2% ammonia solution (14 g). The reaction mixture was filtered and the obtained wet cake washed with water twice (25 g*2). The wet cake was dried at 60° C. to obtain 14.6 g product as white solid.

$^1$H NMR (400 MHZ, DMSO-d$_6$): δ 10.23 (s, 1H), 7.78 (d, J=8.8 Hz, 1H), 7.61 (d, J=9.0 Hz, 1H), 6.95 (s, 1H), 6.89 (s, 1H), 1.89 (s, 3H).

HRMS (High Resolution Mass Spectrometry) m/z, ESI) calc C$_{12}$H$_9$ClF$_3$N$_2$O$^+$ [M+H]$^+$: 289.0284

Step 5

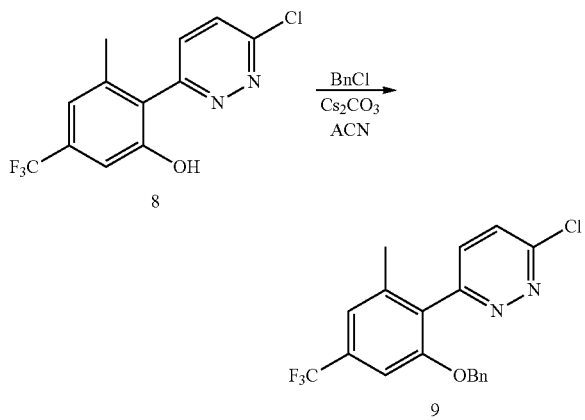

Compound 8 (17.2 g, 1.0 eq.), ACN (172 mL) and CS$_2$CO$_3$ (23.3 g, 1.2 eq.; 200 mesh) was charged to a reactor at a temperature range of 20-30° C. The mixture was stirred for 2 h at 50° C. BnCl (8.3 g, 1.1 eq.) was then added dropwise into the reactor. The mixture was stirred over 10 h at 50° C. The mixture was cooled to room temperature and water (51 g) was added into the mixture. After stirring for 30 min, the organic layer was collected and then H$_2$O (330 g) was added dropwise into the organic layer at a temperature of 20-30° C. and then stirred for 3 h. The reaction mixture was filtered and the cake washed with water (51 g). The wet cake was then dried under vacuum at 55° C. and 21.1 g product was obtained as light brown solid.

$^1$H NMR (400 MHZ, DMSO-d$_6$) δ 7.80 (d, J=8.8 Hz, 1H), 7.69 (d, J=9.0 Hz, 1H), 7.17 (d, J=12.1 Hz, 2H), 7.12-6.97 (m, 5H), 4.96 (s, 2H), 1.90 (s, 3H).

HRMS (High Resolution Mass Spectrometry) (m/z, ESI) calc C$_{19}$H$_{15}$ClF$_3$N$_2$O$^+$ [M+H]$^+$: 379.1378.

Step 6

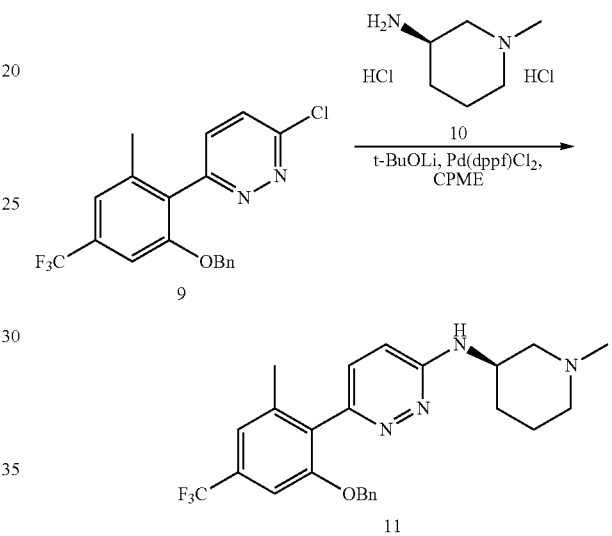

Compound 9 (20 g, 52.8 mmol, 1 eq.), 10 (13.8 g, 73.9 mmol, 1.4 eq.), t-BuOLi (25.4 g, 316.8 mmol, 6 eq.) and CPME (260 mL) were charged to a reactor. The reactor was then put under a N$_2$ atmosphere. Pd(dppf)Cl$_2$ (3.1 g, 4.22 mmol, 0.08 eq.) was then added into the reactor under N$_2$ atmosphere and the mixture stirred for 16 h at a temperature of 60-70° C. The mixture was cooled to a temperature of 20-30° C. after the reaction completed. 4% HCl (aq.) (310 g) was added into the mixture to adjust the pH to 1-2. The aqueous layer was collected and further extracted with isopropyl acetate (150 mL*2) twice. The pH of the aqueous layer was adjusted to between 8 and 9 with 20% NaOH (aq.) and extracted with isopropyl acetate twice (200 mL*2). The combined organic layer was concentrated to ~260 g and then n-heptane (320 g) added dropwise into the mixture by dropwise at 50° C. The mixture was filtered after cooling to 0° C. and a wet cake was obtained. 16.9 g of dry product was obtained as off-white solid after drying for 16 h at 50° C.

$^1$H NMR (400 MHZ, DMSO-d$_6$) δ 7.11-6.99 (m, 7H), 6.66 (d, J=9.3 Hz, 1H), 6.56 (d, J=7.8 Hz, 1H), 4.93 (s, 2H), 3.92-3.80 (m, 1H), 2.64 (d, J=9.0 Hz, 1H), 2.34-2.28 (m, 1H), 1.96 (s, 3H), 1.92 (s, 3H), 1.86-1.76 (m, 1H), 1.77-1.66 (m, 1H), 1.66-1.55 (m, 1H), 1.54-1.43 (m, 1H), 1.40-1.25 (m, 1H), 1.16-1.02 (m, 1H).

HRMS (High Resolution Mass Spectrometry) (m/z, ESI) calc C$_{25}$H$_{28}$F$_3$N$_4$O$^+$ [M+H]$^+$: 457.2232.

Step 7

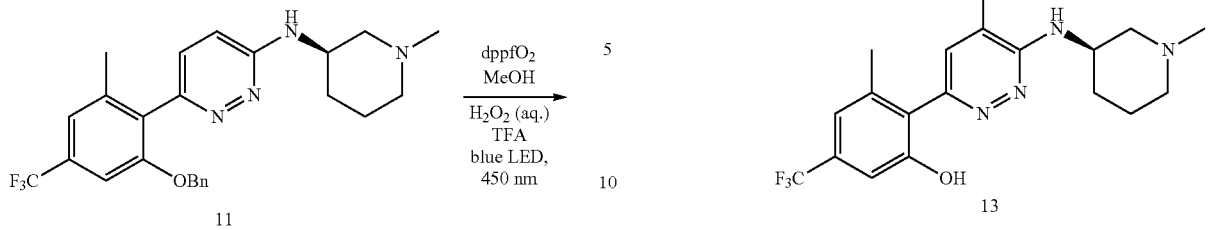

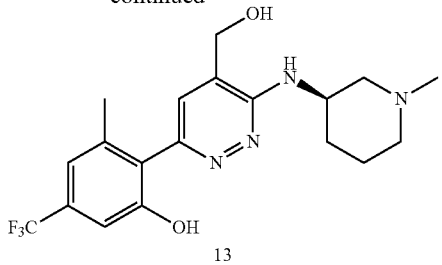

Compound 11 (54 g, 118.3 mmol, 1 eq.), 8% H₂O₂ (aq.) (7.23 g, 212.9 mmol, 1.8 eq.), TFA (26.97 g, 236.6 mmol, 2 eq.), 1,1'-bis (diphenylphosphino) ferrocene dioxide (dppfO2) (0.69 g, 1.18 mmol, 0.01 eq.) and MeOH (504 mL) was charged into a reactor. The reaction mixture was pumped through a blue light reactor (450 nm) by flow at 30° C. The mixture was quenched after completion with 10% Na₂SO₃ (aq.). The pH of the mixture was adjusted to between 8 and 9 with 10% Na₂CO₃ (aq.). The mixture was extracted with isopropyl acetate (600 mL*2) twice. The combined organic layer were then concentrated under vacuum at 40-50° C. and the crude product purified by column. 46 g product was obtained as a off-white solid.

¹H NMR (400 MHZ, DMSO-d₆) δ 7.37-7.23 (m, 8H), 5.98 (d, J=7.8 Hz, 1H), 5.61 (t, J=5.2 Hz, 1H), 5.18 (s, 2H), 4.48-4.38 (m, 2H), 4.35-4.25 (m, 1H), 2.91-2.80 (m, 1H), 2.19 (s, 3H), 2.16 (s, 3H), 2.10-1.98 (m, 2H), 1.87-1.79 (m, 1H), 1.76-1.66 (m, 1H), 1.61-1.51 (m, 1H), 1.49-1.40 (m, 1H).

HRMS (High Resolution Mass Spectrometry) (m/z, ESI) calc $C_{26}H_{30}F_3N_4O_2^+$ [M+H]⁺: 487.2321.

Step 8

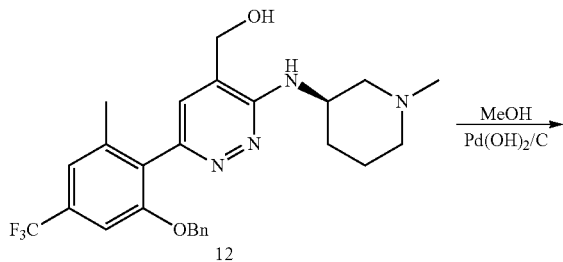

Compound 12 (25.3 g, 52.08 mmol, 1 eq.), 20% Pd(OH)₂/C (50% wet, 7.3 g) and MeOH (860 mL) was charged to a reactor. The mixture was stirred for 17 h at 25° C. with 1 bar H₂ pressure. The mixture was filtered through a MCC pad after the reaction completed. The filtrate was concentrated and then acetonitrile (~150 g) was added at a temperature range of 40-50° C. The mixture was cooled to a temperature of 10-20° C. and then filtered. The wet cake was then washed with acetonitrile (100 mL) and MeOH (10 mL) at 50° C. for 2 h and the mixture cooled to a temperature range of 20-30° C. The wet cake was dried at 50° C. to obtain 14.4 g product.

¹H NMR (400 MHZ, DMSO-d₆) δ 10.12 (br s, 1H), 7.22 (s, 1H), 7.11 (s, 1H), 7.06 (s, 1H), 5.95 (d, J=7.9 Hz, 1H), 5.58 (br s, 1H), 4.42 (s, 2H), 4.35-4.18 (m, 1H), 2.84 (d, J=10.4 Hz, 1H), 2.19 (s, 3H), 2.12 (s, 3H), 2.09-1.96 (m, 2H), 1.88-1.76 (m, 1H), 1.75-1.64 (m, 1H), 1.61-1.50 (m, 1H), 1.50-1.37 (m, 1H).

HRMS (High Resolution Mass Spectrometry) (m/z, ESI) calc $C_{19}H_{24}F_3N_4O_2^+$ [M+H]⁺: 397.1160.

Crystalline Forms of Example 1

1. Preparation of Crystalline Forms 1.1: Preparation of Form $H_A$:

Example (A): (R)-2-(5-(hydroxymethyl)-6-((1-methylpiperidin-3-yl)amino)pyridazin-3-yl)-3-methyl-5-(trifluoromethyl)phenol Form A (example 1, 30 mg, preparation see below) was added into 1 mL acetonitrile/water (94.35/4.11, v/v, $a_w$=0.6) and then the suspension was stirred at RT. After 3 days, the suspension was filtered and the wet cake was air dried for 4 h to provide (R)-2-(5-(hydroxymethyl)-6-((1-methylpiperidin-3-yl)amino)pyridazin-3-yl)-3-methyl-5-(trifluoromethyl)phenol hydrate $H_A$.

Example (B): (R)-2-(5-(hydroxymethyl)-6-((1-methylpiperidin-3-yl)amino)pyridazin-3-yl)-3-methyl-5-(trifluoromethyl)phenol (example 1, 2.0 g) was dissolved in 34 g IPA/water (80/20, w/w) at 70° C. with a stirring rate of 250 rpm. The temperature was cooled to 45° C. in 30 min and then a small amount of $H_A$ prepared in example (A) (10 mg) was added. After holding for 3 h, 5 g water was dropped in 20 min and then hold for 4 h. The temperature was cooled to 0° C. in 7 h, and then the suspension was filtered followed by washing the wet cake with IPA/water (70/30, w/w). The wet cake was dried at 45° C. with vacuum for 4 h and 50° C. with vacuum for 3 hours.

1.2: Preparation of Form A:

Example (A): Water (19.7 kg), Intermediate 2 (1.25 kg, 4.87 mol, 1.0 equivalent), 2-methyltetrahydrofuran (21.4 kg), Intermediate 4 (1.76 kg, 5.83 mol, 1.2 equivalent), NaOtBu (1.40 kg, 14.57 mol, 3 equivalent) and 1,1'-bis(diisopropylphosphino)ferrocene palladium dichloride (0.175 kg, 0.29 mol, 0.06 equivalent) was charged to a reactor under nitrogen. The resulting solution was stirred at 70° C. for 16 h before being the reaction mixture was extracted with aqueous HCl solution twice. The resulting aqueous phases were combined and extracted with 2-methyltetrahydrofuran. The organic phase was collected and N-acetyl-cysteine and SiliaMetS® Thiol (Si-THU) were applied, respectively, to remove Pd residue. Afterwards, the organic phase was concentrated until dry (removal of solvent) and crystallization was conducted with MeOH and water. The resulting wet product was recrystallized in EtOH and n-heptane. Compound 7a was finally obtained as off-white solid with a yield of 23% (402 g, 1.01 mol) after drying.

(400 MHZ, DMSO-$d_6$): δ: 10.12 (s, 1H, ArOH), 7.23 (s, 1H, ArH), 7.08 (dd, 2H, ArH), 5.95 (d, 1H, NH), 5.59 (s, 1H, CH2OH), 4.43 (s, 2H, CH2OH), 4.30 (tp, 1H, CH), 3.40 (s, 1H, CHCH2N), 2.85 (m, 1H, CHCH2N), 2.19 (s, 3H, Me), 2.12 (s, 3H, Me), 2.08 (s, 2H, CH2CH2N), 1.81 (m, 1H, CHCH2CH2), 1.70 (qd, 1H, CHCH2CH2), 1.55 (qd, 1H, CH2CH2N), 1.46 (t, 1H, CH2CH2N).

$^{13}$C NMR (100 MHZ, DMSO-$d_6$): δ: 155.8, 155.1, 149.1, 139.4, 129.6, 128.8, 126.6, 125.6, 125.5, 122.8 (CF3), 117.1, 109.4, 109.4, 60.5, 58.9 (CH2OH), 55.4, 46.7, 46.2, 23.3, 20.0 (2C).

$^{19}$F NMR (376 MHZ, DMSO-$d_6$): δ: −61.4.

LCMS (m/z, ESI+) UPLC-MS (method 2): calculated for $C_{19}H_{23}F_3N_4O_2$: 396.18. Detected $[M+H]^+$: 397.1818.

Example (B): (R)-2-(5-(hydroxymethyl)-6-((1-methylpiperidin-3-yl)amino)pyridazin-3-yl)-3-methyl-5-(trifluoromethyl)phenol (example 1, 2.0 g) was dissolved in 32 g ethanol and 0.8 g water at 70° C. with a stirring rate of 250 rpm. The temperature was cooled to 40° C. in 30 min and then 80 mg Mod A seed was added. After holding for 3 hours, 20 mL n-heptane was dropped over 1 hour, and then kept stirring at 40° C. for 12 hours. The temperature was cooled to 30° C. over 2 h followed by holding for 4 h. After that, the temperature was cooled to 20° C. over 2 hours followed by holding for 4 h. At last, the temperature was cooled to 0° C. in 7 h, and then the residual wet cake was washed by with n-heptane. After filtration and wash, the obtained wet cake was vacuum dried at 40° C.

1.3: Preparation of Form B:

(R)-2-(5-(hydroxymethyl)-6-((1-methylpiperidin-3-yl)amino)pyridazin-3-yl)-3-methyl-5-(trifluoromethyl)phenol (400 mg) was dissolved into 6 mL MeOH at 70° C., and then the solution was filtered via a 22 μm membrane. The solution/suspension was reheated to 70° C. to get a clear solution, and then the temperature was cooled to 55° C. in 2 h. After leaving the solution for 2 h, the temperature was cooled to 5° C. over 10 h and held overnight. The suspension was filtered and the wet cake was vacuum dried at 50° C. for 2 h to provide (R)-2-(5-(hydroxymethyl)-6-((1-methylpiperidin-3-yl)amino)pyridazin-3-yl)-3-methyl-5-(trifluoromethyl)phenol Form B.

1.4: Preparation of Example 1 Hippurate (1:1):

(R)-2-(5-(hydroxymethyl)-6-((1-methylpiperidin-3-yl)amino)pyridazin-3-yl)-3-methyl-5-(trifluoromethyl)phenol (1.5 g) and 711.9 mg hippuric acid were added into 30 mL MEK and kept stirring at 50° C. with a stirring speed about 250 rpm. After 4 hours, the temperature was cooled to 25° C. in 2 hours and held for overnight. The suspension was filtered and the wet cake was washed with MEK followed by vacuum dry at 50° C. for 4 hours to provide (R)-2-(5-(hydroxymethyl)-6-((1-methylpiperidin-3-yl)amino)pyridazin-3-yl)-3-methyl-5-(trifluoromethyl)phenol hippurate (1:1) salt.

1.5: Preparation of Example 1 Hydrochloride (1:1):

Example (A): (R)-2-(5-(hydroxymethyl)-6-((1-methylpiperidin-3-yl)amino)pyridazin-3-yl)-3-methyl-5-(trifluoromethyl)phenol (60 mg) and 11.6 μL aqueous HCl acid (12 mol/L) were added into 1 mL methyl ethyl ketone at RT and suspension was obtained. The temperature was raised to 50° C. and held or 4 h. After 4 h, the temperature was cooled to 25° C. and held for over weekend. The suspension was filtered and the wet cake was washed with MEK followed by vacuum dry at 50° C. for 4 h to provide (R)-2-(5-(hydroxymethyl)-6-((1-methylpiperidin-3-yl)amino)pyridazin-3-yl)-3-methyl-5-(trifluoromethyl)phenol hydrochloride (1:1) salt.

Example (B): (R)-2-(5-(hydroxymethyl)-6-((1-methylpiperidin-3-yl)amino)pyridazin-3-yl)-3-methyl-5-(trifluoromethyl)phenol (100 mg) and 22.08 μL aqueous HCl acid (12 mol/L) were added into 0.7 mL MeOH at RT, and clear solution was obtained. A small amount of of HCl salt prepared in Example (A) was added after adding 1.4 mL MTBE. After aging for 2 h, 1.4 mL MTBE was added in 30 min, then held for 4 h. The temperature was cooled to 5° C. and held for overnight. The suspension was filtered and the wet cake was vacuum dried at 50° C. for 2 h.

2. Characterization of Crystalline Forms 2.1 Analytical Equipment 2.1.1 X-ray Powder Diffraction Method X-ray powder diffraction (XRPD) patterns were obtained using a Bruker Advance D8 in reflection geometry. Powders were analyzed using a zero background Si flat sample holder. The radiation was Cu Kα (λ=1.5418 Å). Patterns were measured between 2° and 40° 2-Theta range. The error limit for the 2-Theta angles is ±0.2°.

Sample amount: 5-10 mg

Sample holder: zero background Si flat sample holder

XRPD Parameter:

| | |
|---|---|
| Instrument | Bruker D8 Advance |
| Detector | LYNXEYE (1D mode), open angle: 2.948°, scan mode: continuous scan |
| Radiation | CuKα (0.15418 nm) |
| Monochromator | Nickel filter |
| X-ray generator power | 40 kV, 40 mA |
| Goniometer radius | 280 mm |
| Step size | 0.0164° (2-theta value) |
| Time per step | 0.3 second per step |
| Scan range | 2° to 40° (2-theta value) |
| Scan time | About 768 seconds |
| Slits | Primary: fixed illuminated sample size 10 mm; secondary: open angle 2.2°, axial soller: 2.5° |

The most characteristic peaks in XRPD pattern of each form are marked as A (strong), B (medium), C (medium), D (medium).

2.1.2 Differential Scanning Calorimetry (DSC) Method

DSC traces were recorded on a TA Discovery DSC with aluminium pan (TA, Tzero pan, 901683.901); heating rate 10 K/min, temperature range: 0 to 300° C.

2.1.3 Thermal Gravimetric Analysis (TGA) Method

TGA traces were recorded on a TA Discovery TGA with aluminium pan (TA); heating rate 10 K/min, temperature range: room temperature to 300° C.

2.2: Characterization of Crystalline Form H$_A$:
2.2.1 XRPD Data for Form H$_A$

XRPD data for form H$_A$ are given below in Table 1.

TABLE 1

| Index in FIG. 1 | Angle [2-Theta°] | d Value [Angstrom] | Relative intensity [%] |
| --- | --- | --- | --- |
| 1 | 5.04° | 3.07 Å | 4.6% |
| 2 | 10.08° | 3.17 Å | 7.1% |
| 3 | 11.68° | 3.41 Å | 15.1% |
| 4 | 12.01° | 3.62 Å | 16.3% |
| 5 | 13.03° | 3.70 Å | 18.9% |
| 6 | 15.23° | 3.83 Å | 10.5% |
| 7 | 16.15° | 3.88 Å | 32.8% |
| 8 | 16.58° | 4.21 Å | 28.3% |
| 9 | 17.98° | 4.33 Å | 25.8% |
| 10 | 19.76° | 4.39 Å | 18.1% |
| 11 | 20.02° | 4.43 Å | 15.7% |
| 12-D | 20.21° | 4.49 Å | 52.1% |
| 13-B | 20.52° | 4.93 Å | 89.6% |
| 14-C | 21.07° | 5.34 Å | 78.2% |
| 15 | 22.92° | 5.48 Å | 10.0% |
| 16-A | 23.21° | 5.81 Å | 100.0% |
| 17 | 24.01° | 6.79 Å | 23.3% |
| 18 | 24.57° | 7.36 Å | 5.9% |
| 19 | 26.14° | 7.57 Å | 4.9% |
| 20 | 28.09° | 8.77 Å | 31.7% |
| 21 | 29.06° | 17.51 Å | 10.7% |

2.2.2 Differential Scanning Calorimetry (DSC) Data for Form H$_A$

Figure 2:
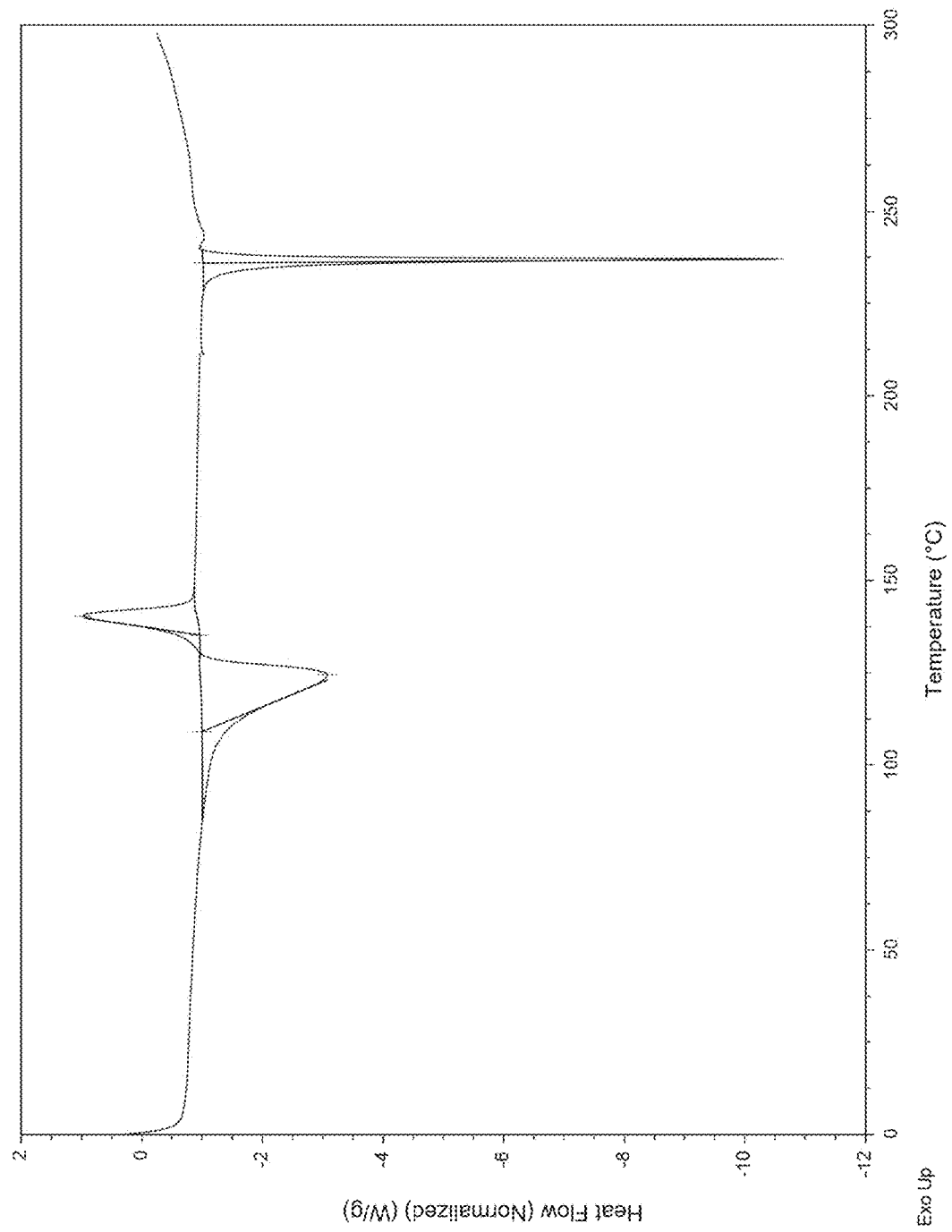
FIG. 2 shows the differential scanning calorimetry (DSC) trace of form $H_A$.

FIG. 2 shows the DSC trace of form H$_A$. The onset melting temperature of the first endothermic peak is 109.1° C. (the first endothermic peak: 124.5° C.), the onset melting temperature of the second endothermic peak is 235.8° C. (the second endothermic peak: 236.9° C.).

2.2.3 Thermal Gravimetric Analysis (TGA)

Figure 3:
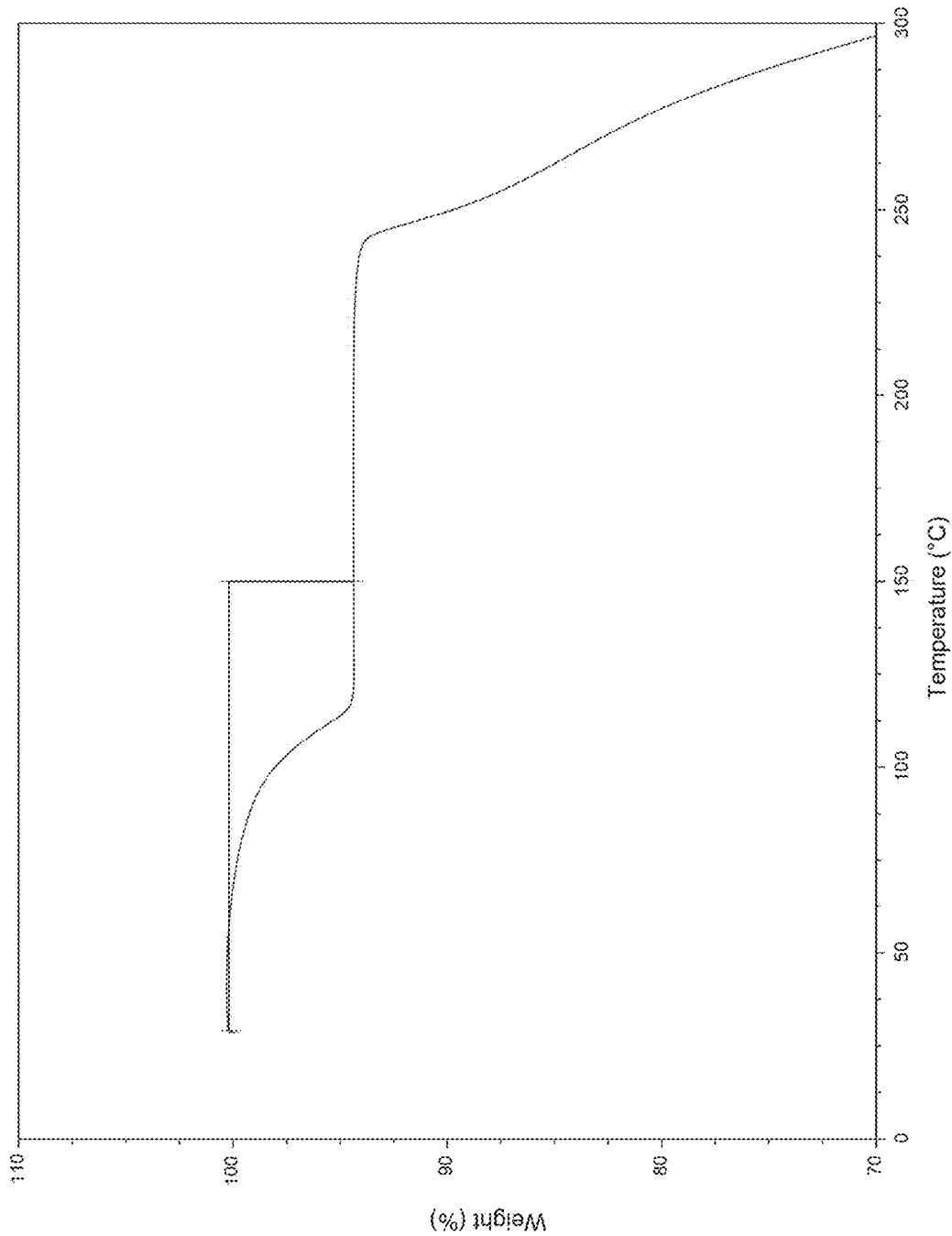
FIG. 3 shows the shows the thermal gravimetric analysis (TGA) trace of form $H_A$.

FIG. 3 shows the TGA trace of form H$_A$.

2.3: Characterization of Crystalline Form A:
2.3.1 XRPD Data for Form A:

XRPD data for form A are given below in Table 2.

TABLE 2

Figure 4:
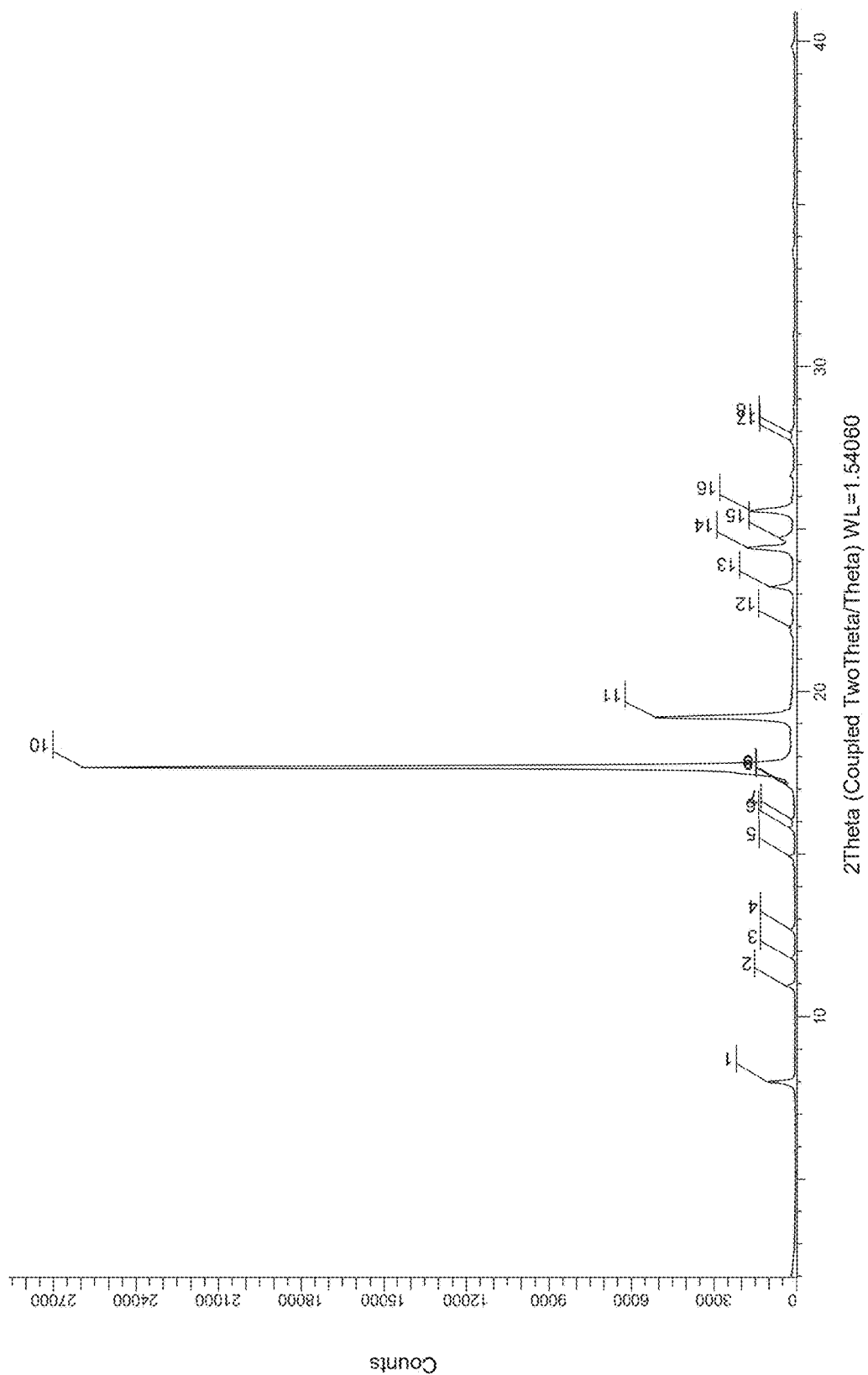
FIG. 4 shows the X-ray powder diffraction pattern of form A.

| Index in FIG. 4 | Angle [2-Theta°] | d Value [Angstrom] | Relative intensity [%] |
| --- | --- | --- | --- |
| 1 | 8.00° | 11.04 Å | 3.9% |
| 2 | 10.94° | 8.08 Å | 1.3% |
| 3 | 11.79° | 7.50 Å | 0.5% |
| 4 | 12.69° | 6.97 Å | 0.5% |
| 5 | 14.93° | 5.93 Å | 0.6% |
| 6 | 15.81° | 5.60 Å | 0.7% |
| 7 | 16.07° | 5.51 Å | 0.4% |
| 8 | 17.12° | 5.18 Å | 0.8% |
| 9 | 17.15° | 5.17 Å | 0.9% |
| 10 | 17.68° | 5.01 Å | 100.0% |
| 11 | 19.21° | 4.62 Å | 19.2% |
| 12 | 22.01° | 4.04 Å | 0.5% |
| 13 | 23.23° | 3.83 Å | 3.1% |
| 14 | 24.42° | 3.64 Å | 6.3% |
| 15 | 24.72° | 3.60 Å | 1.8% |
| 16 | 25.56° | 3.48 Å | 5.9% |
| 17 | 27.73° | 3.21 Å | 0.5% |
| 18 | 27.97° | 3.19 Å | 0.5% |

2.3.2. Differential Scanning Calorimetry (DSC) Data for Form A

Figure 5:
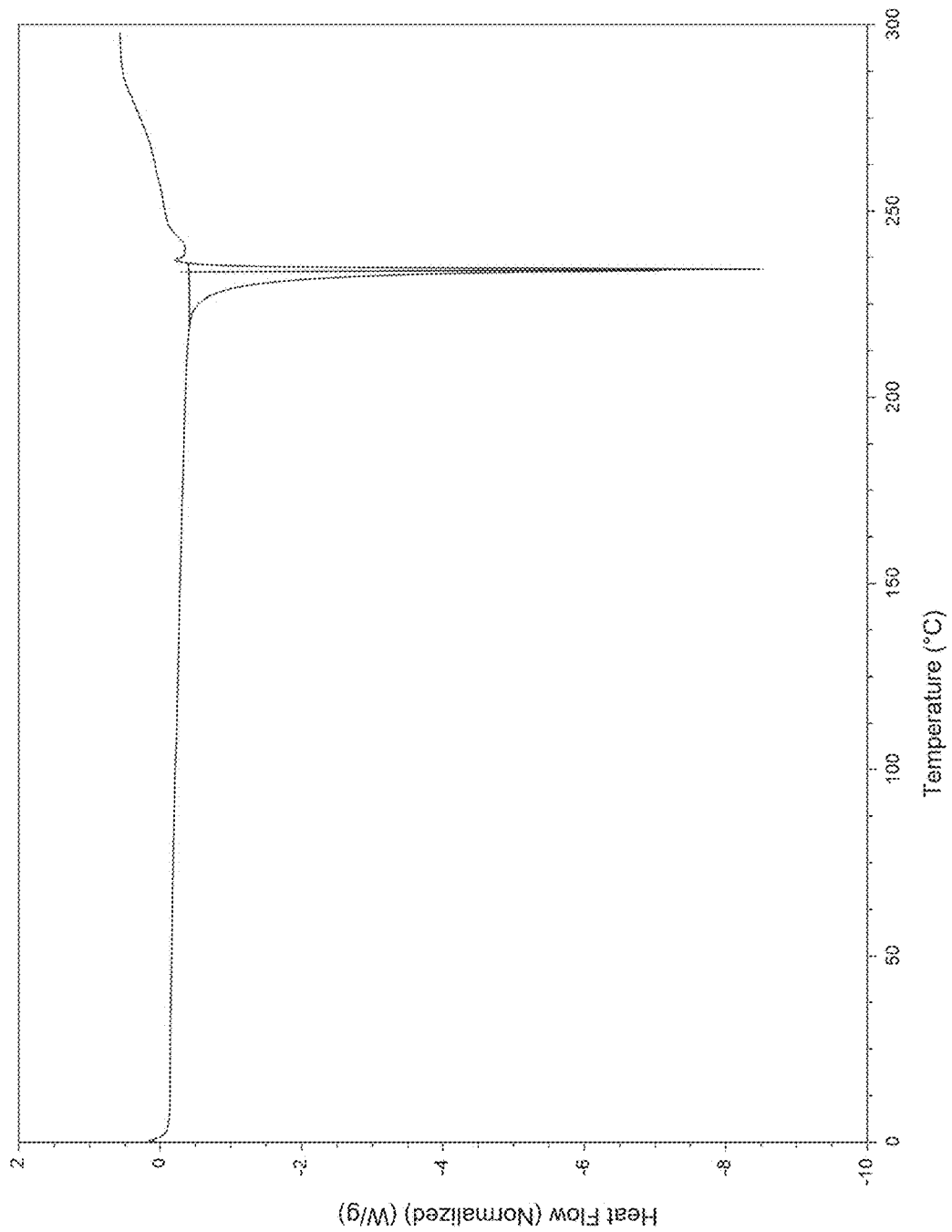
FIG. 5 shows the differential scanning calorimetry (DSC) trace of form A.

FIG. 5 shows the DSC trace of form A. The onset melting temperature of the endothermic peak is 233.6° C. (the endothermic peak: 234.4° C.).

2.3.3 Thermal Gravimetric Analysis (TGA)

Figure 6:
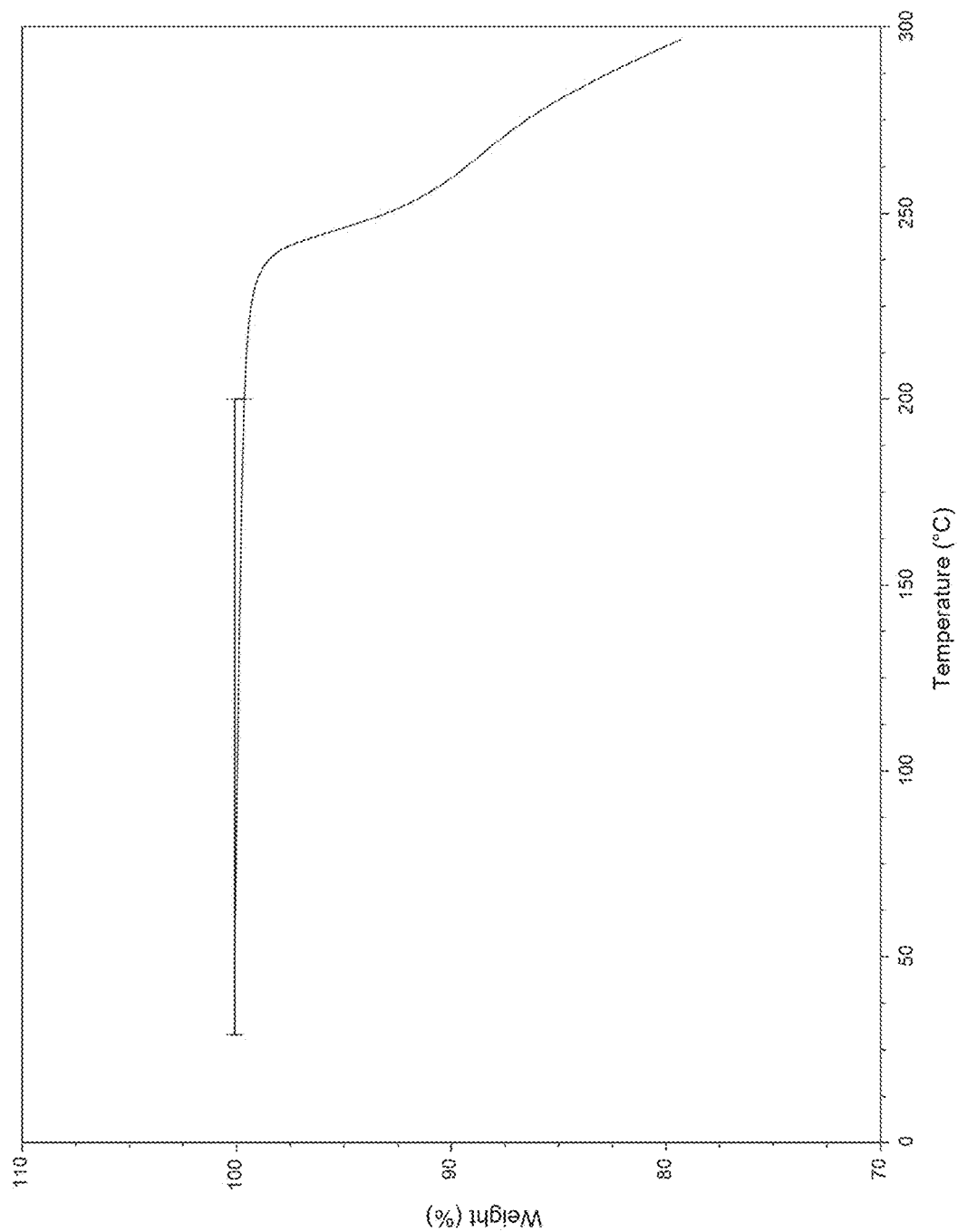
FIG. 6 shows the TGA trace of form A.

FIG. 6 shows the TGA trace of form A.

2.4: Characterization of Crystalline Form B:
2.4.1 XRPD Data for Form B:

XRPD data for form B are given below in Table 3.

TABLE 3

Figure 7:
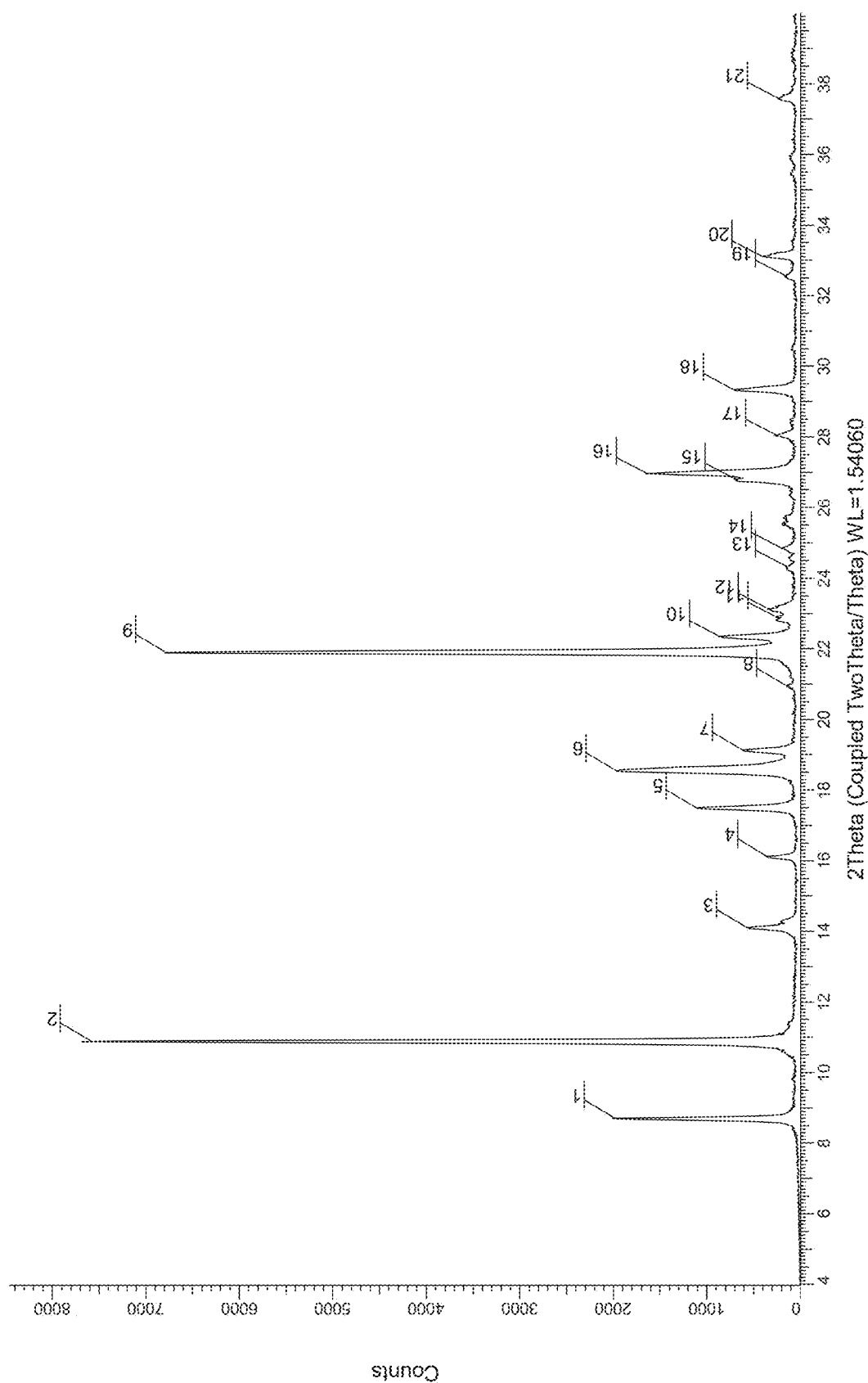
FIG. 7 shows the X-ray powder diffraction pattern of form B.

| Index in FIG. 7 | Angle [2-Theta°] | d Value [Angstrom] | Relative intensity [%] |
| --- | --- | --- | --- |
| 1 | 8.71° | 10.15 Å | 25.6% |
| 2 | 10.89° | 8.12 Å | 100.0% |
| 3 | 14.10° | 6.28 Å | 6.9% |
| 4 | 16.11° | 5.50 Å | 3.9% |
| 5 | 17.49° | 5.07 Å | 13.8% |
| 6 | 18.55° | 4.78 Å | 25.1% |
| 7 | 19.13° | 4.64 Å | 7.1% |
| 8 | 20.94° | 4.24 Å | 0.9% |
| 9 | 21.90° | 4.06 Å | 88.9% |
| 10 | 22.34° | 3.98 Å | 10.1% |
| 11 | 22.87° | 3.89 Å | 1.9% |
| 12 | 23.12° | 3.84 Å | 3.4% |
| 13 | 24.34° | 3.65 Å | 1.1% |
| 14 | 24.85° | 3.58 Å | 1.7% |
| 15 | 26.80° | 3.32 Å | 8.2% |
| 16 | 26.98° | 3.30 Å | 20.8% |
| 17 | 28.05° | 3.18 Å | 2.5% |
| 18 | 29.34° | 3.04 Å | 8.6% |
| 19 | 32.56° | 2.75 Å | 1.2% |
| 20 | 33.12° | 2.70 Å | 4.5% |
| 21 | 37.59° | 2.39 Å | 2.4% |

2.4.2. Differential Scanning Calorimetry (DSC) Data for Form B

Figure 8:
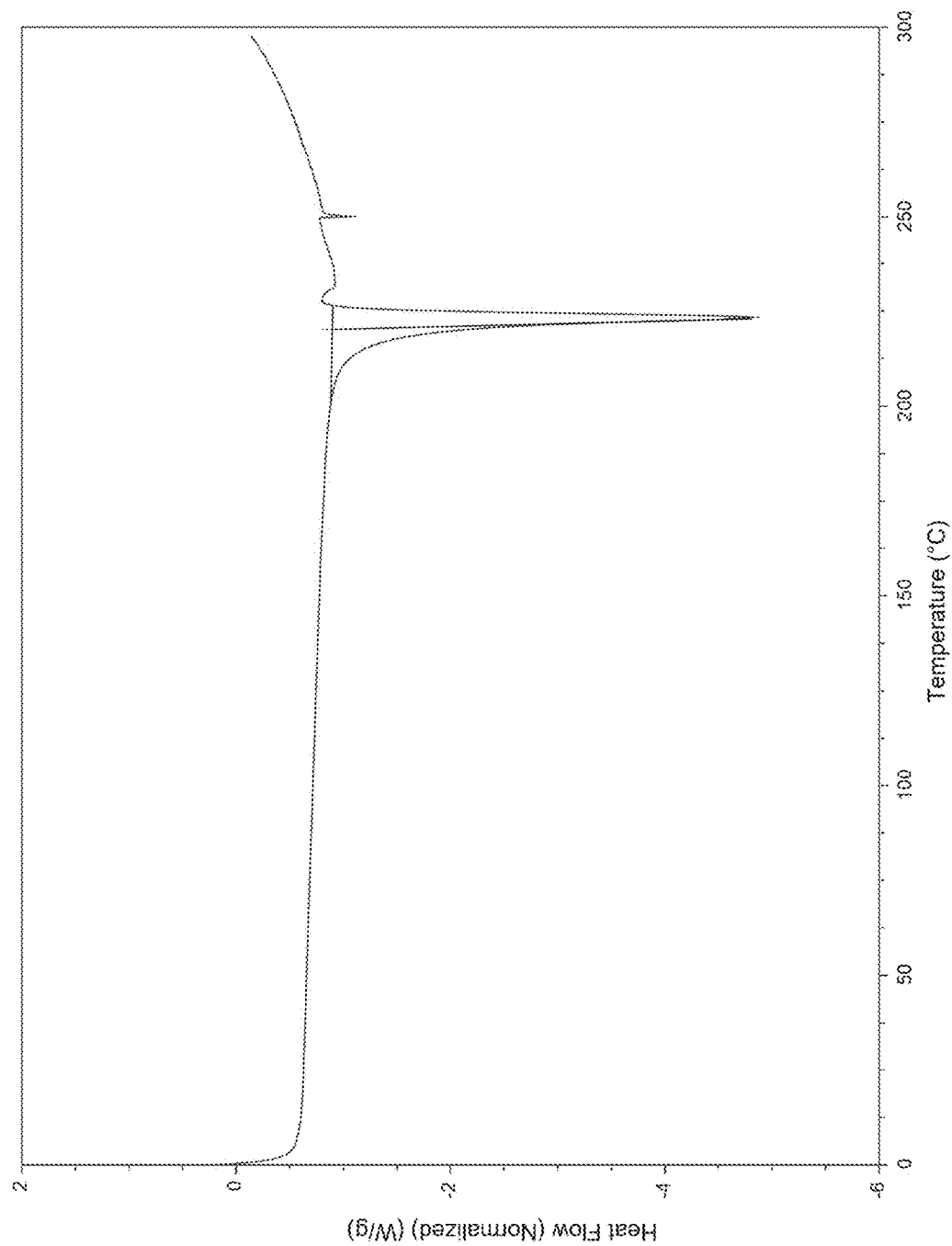
FIG. 8 shows the differential scanning calorimetry (DSC) trace of form B.

FIG. 8 shows the DSC trace of form B. The onset melting temperature of the endothermic peak is 220.1° C. (the endothermic peak: 223.4° C.).

2.4.3 Thermal Gravimetric Analysis (TGA) for Form B

Figure 9:
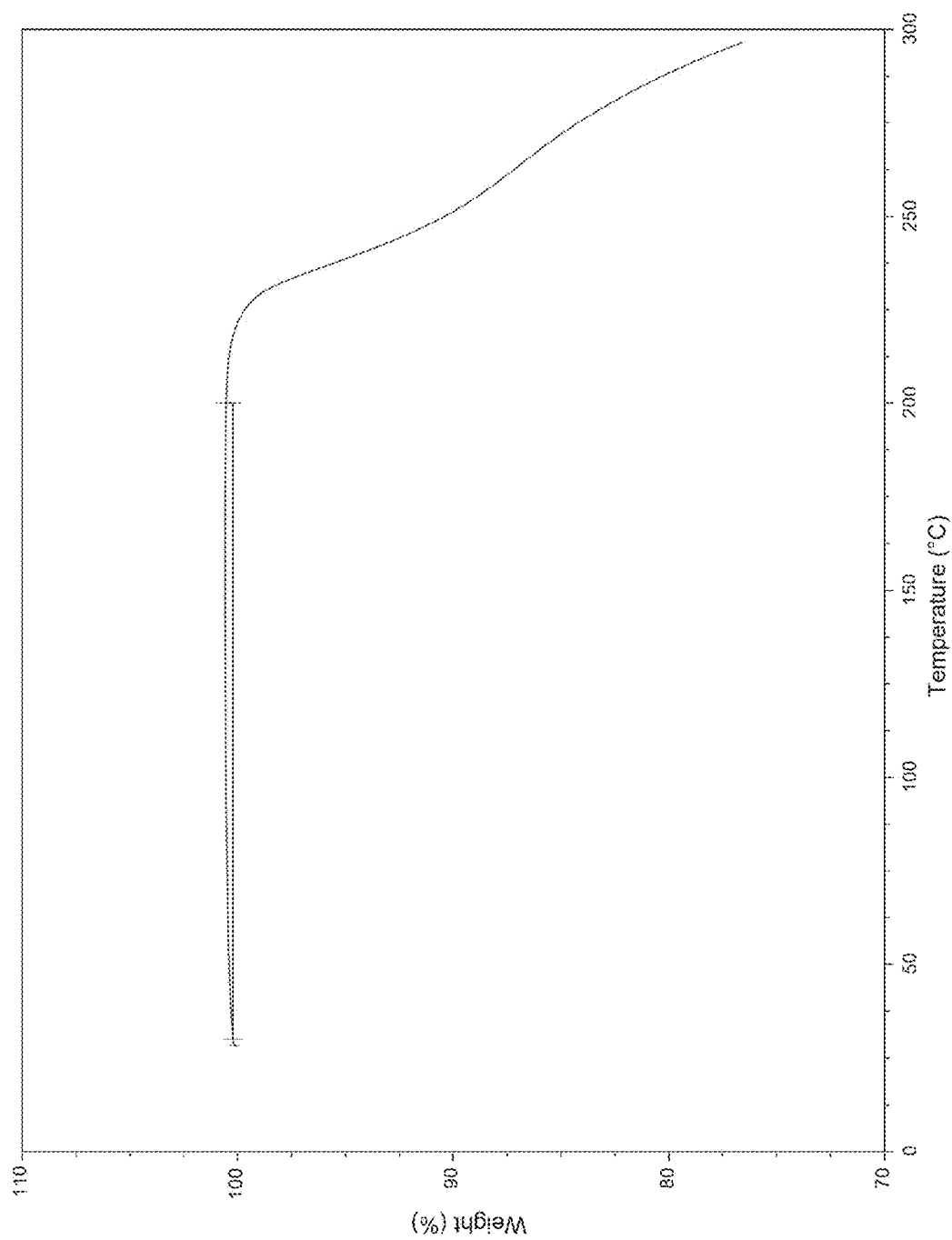
FIG. 9 shows the TGA trace of form B.

FIG. 9 shows the TGA trace of form B.

2.5: Characterization of Crystalline Form Example 1 Hippurate (1:1):
2.5.1 XRPD Data for Form Example 1 Hippurate (1:1):

XRPD data for form example 1 hippurate (1:1) are given below in Table 4.

TABLE 4

Figure 10:
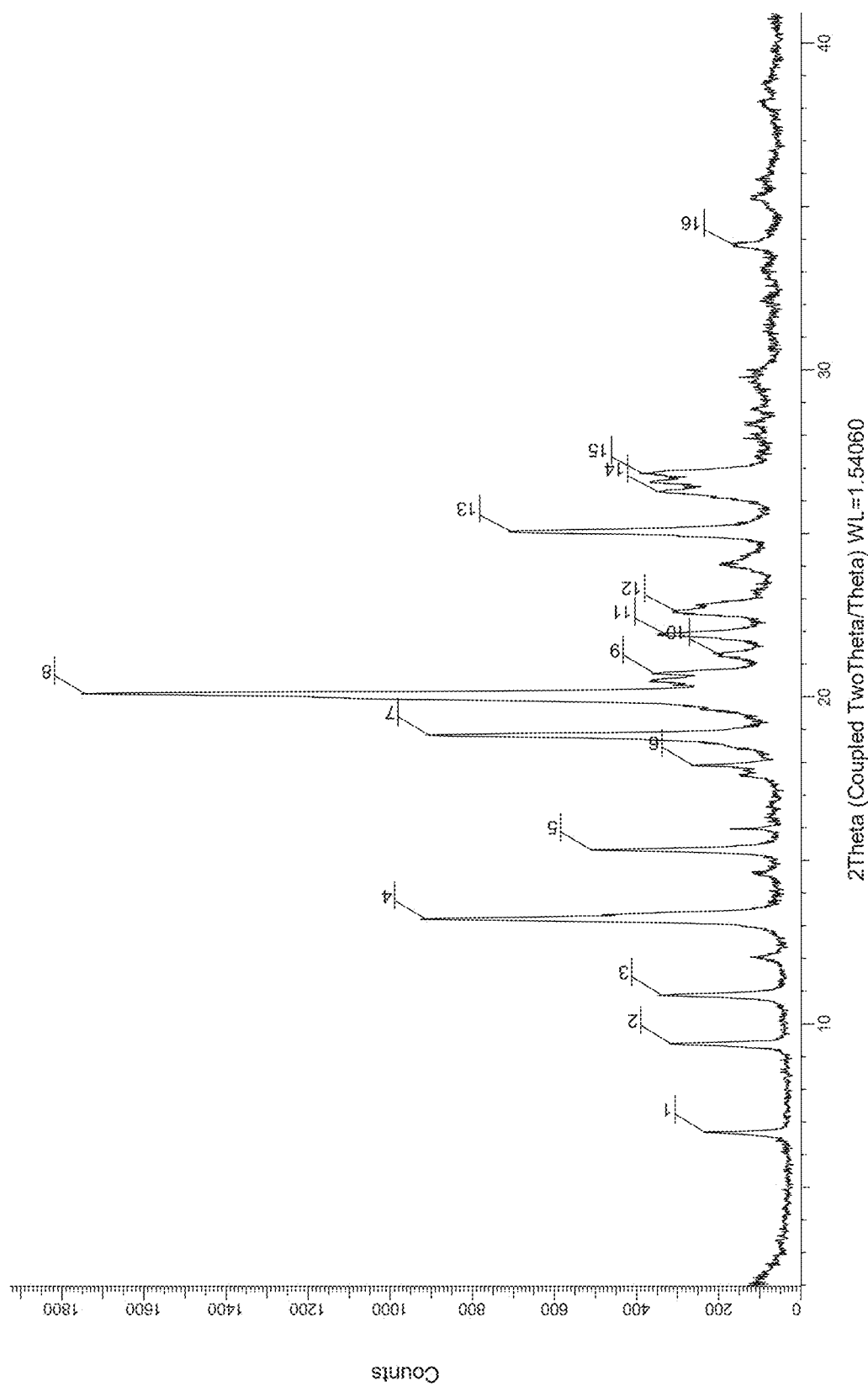
FIG. 10 shows the X-ray powder diffraction pattern of form example 1 hippurate (1:1).

| Index in FIG. 10 | Angle [2-Theta°] | d Value [Angstrom] | Relative intensity [%] |
| --- | --- | --- | --- |
| 1 | 6.68° | 13.22 Å | 12.3% |
| 2 | 9.40° | 9.40 Å | 17.0% |
| 3 | 10.88° | 8.12 Å | 18.1% |
| 4 | 13.22° | 6.69 Å | 52.8% |
| 5 | 15.33° | 5.78 Å | 27.5% |
| 6 | 17.92° | 4.95 Å | 11.3% |
| 7 | 18.83° | 4.71 Å | 49.7% |
| 8 | 20.10° | 4.41 Å | 100.0% |
| 9 | 20.73° | 4.28 Å | 15.2% |
| 10 | 21.29° | 4.17 Å | 5.4% |
| 11 | 21.92° | 4.05 Å | 13.7% |
| 12 | 22.64° | 3.92 Å | 12.7% |
| 13 | 25.07° | 3.55 Å | 37.8% |
| 14 | 26.29° | 3.39 Å | 15.6% |
| 15 | 26.85° | 3.32 Å | 18.1% |
| 16 | 33.82° | 2.65 Å | 5.9% |

2.5.2. Differential Scanning Calorimetry (DSC) Data for form example 1 Hippurate (1:1)

Figure 11:
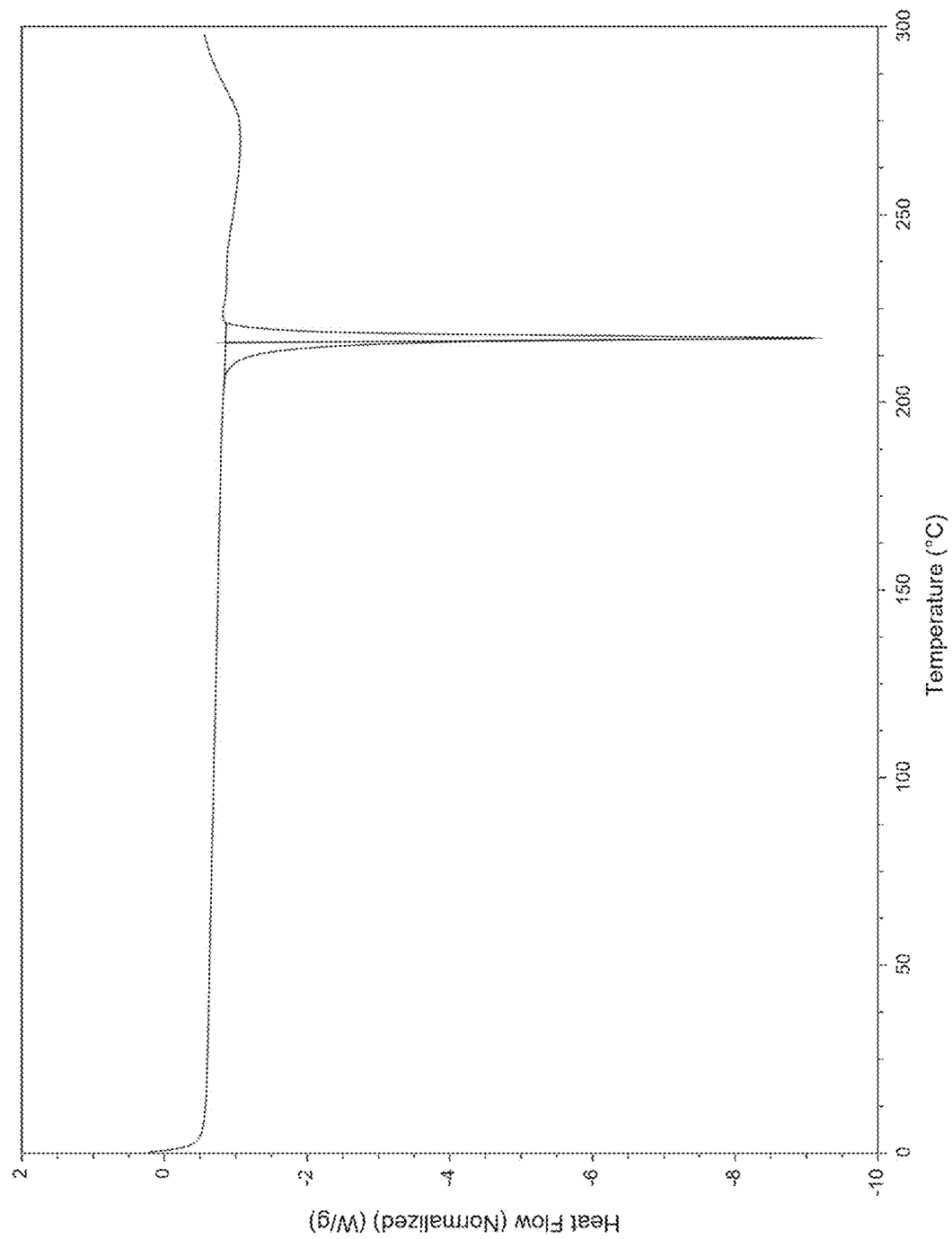
FIG. 11 shows the differential scanning calorimetry (DSC) trace of form example 1 hippurate (1:1).

FIG. 11 shows the DSC trace of example 1 hippurate (1:1). The onset melting temperature of the endothermic peak is 215.9° C. (the endothermic peak: 217.1° C.).

2.5.3 Thermal Gravimetric Analysis (TGA) for Example 1 Hippurate (1:1)

Figure 12:
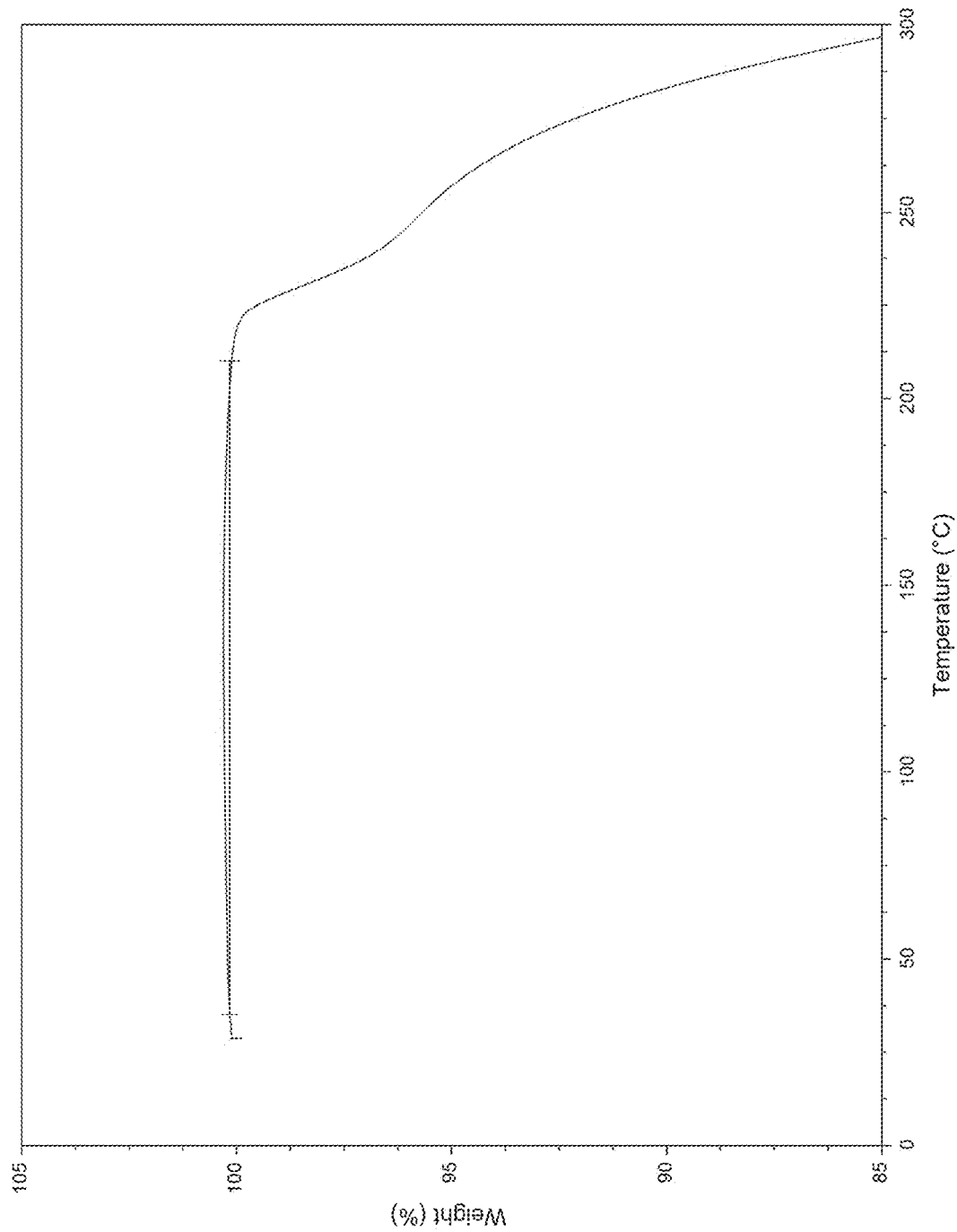
FIG. 12 shows the TGA trace of form example 1 hippurate (1:1).

FIG. 12 shows the TGA trace of form example 1 hippurate (1:1).

2.6: Characterization of Crystalline Form Example 1 Hydrochloride (1:1):

2.6.1 XRPD Data for Form Example 1 Hydrochloride (1:1):

XRPD data for form example 1 hydrochloride (1:1) are given below in Table 5.

TABLE 5

Figure 13:
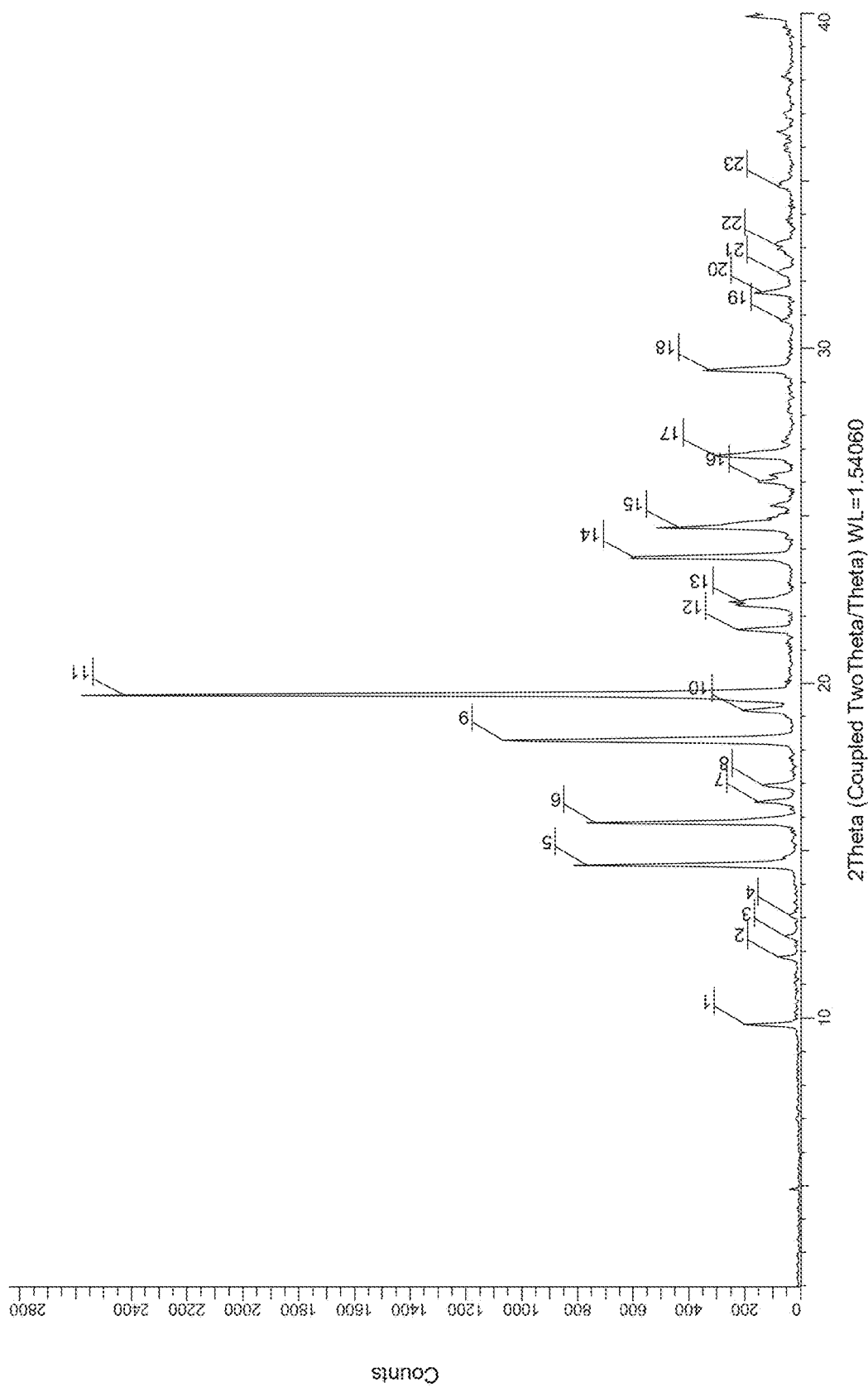
FIG. 13 shows the X-ray powder diffraction pattern of example 1 hydrochloride (1:1).

| Index in FIG. 13 | Angle [2-Theta°] | d Value [Angstrom] | Relative intensity [%] |
|---|---|---|---|
| 1 | 9.82° | 9.00 Å | 7.8% |
| 2 | 11.82° | 7.48 Å | 2.7% |
| 3 | 12.45° | 7.10 Å | 1.6% |
| 4 | 13.09° | 6.76 Å | 1.1% |
| 5 | 14.58° | 6.07 Å | 31.3% |
| 6 | 15.84° | 5.59 Å | 29.9% |
| 7 | 16.47° | 5.38 Å | 5.3% |
| 8 | 16.95° | 5.23 Å | 4.5% |
| 9 | 18.30° | 4.84 Å | 43.4% |
| 10 | 19.20° | 4.62 Å | 7.1% |
| 11 | 19.67° | 4.51 Å | 100.0% |
| 12 | 21.61° | 4.11 Å | 8.0% |
| 13 | 22.39° | 3.97 Å | 6.9% |
| 14 | 23.77° | 3.74 Å | 23.4% |
| 15 | 24.67° | 3.61 Å | 16.8% |
| 16 | 26.04° | 3.42 Å | 4.5% |
| 17 | 26.82° | 3.32 Å | 11.3% |
| 18 | 29.37° | 3.04 Å | 12.0% |
| 19 | 30.86° | 2.90 Å | 1.3% |
| 20 | 31.69° | 2.82 Å | 4.2% |
| 21 | 32.27° | 2.77 Å | 1.9% |
| 22 | 33.09° | 2.70 Å | 2.4% |
| 23 | 34.84° | 2.57 Å | 1.9% |

2.6.2. Differential Scanning Calorimetry (DSC) Data for Form Example 1 Hydrochloride (1:1)

Figure 14:
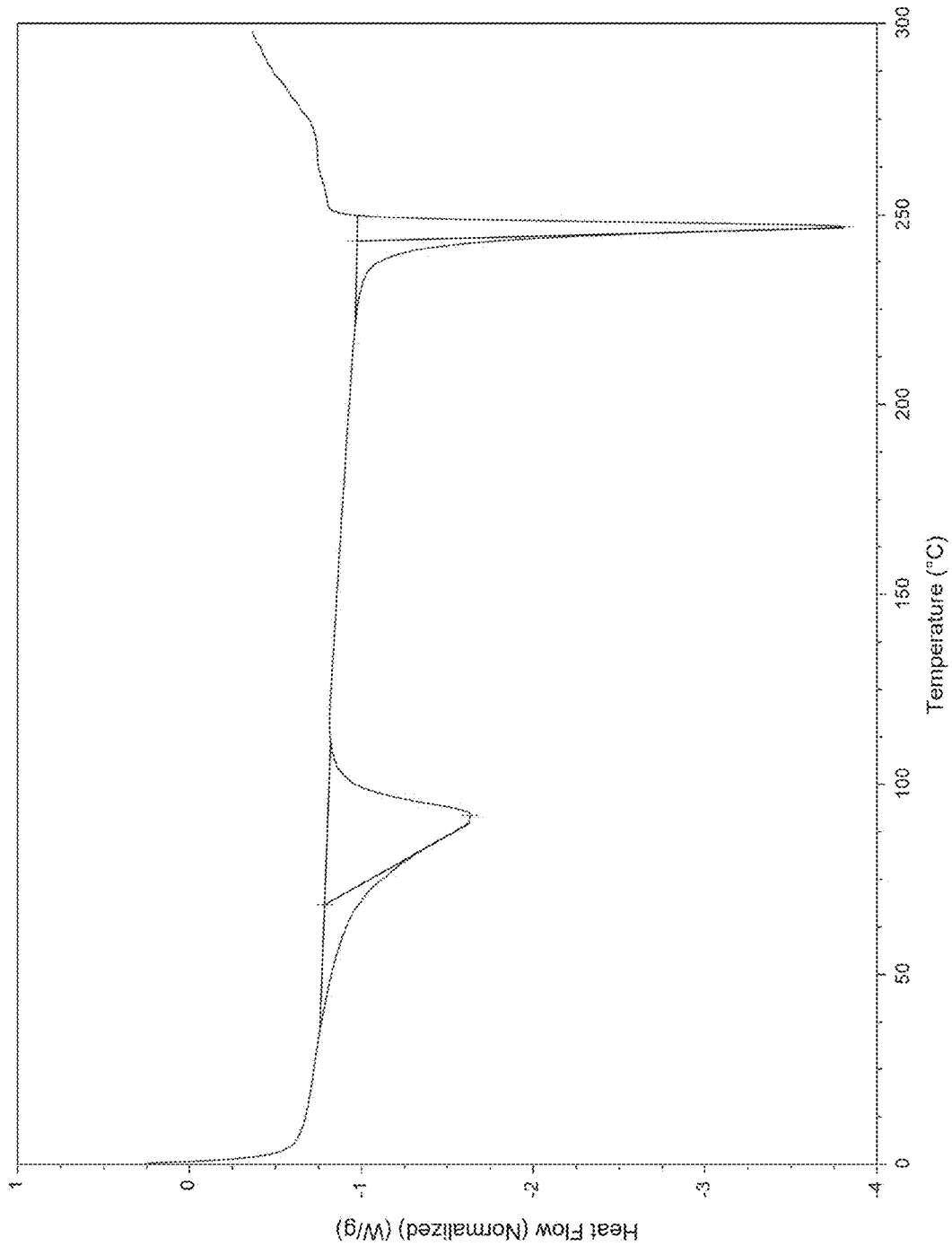
FIG. 14 shows the differential scanning calorimetry (DSC) trace of form hydrochloride (1:1).

FIG. 14 shows the DSC trace of example 1 hydrochloride (1:1). The onset melting temperature of the first endothermic peak is 68.3° C. (the endothermic peak: 91.7° C.), the onselt melting temperature of the second endothermic peak 243.0° C. (the endothermic peak: 246.8° C.).

2.6.3 Thermal Gravimetric Analysis (TGA) for Example 1 Hydrochloride (1:1)

Figure 15:
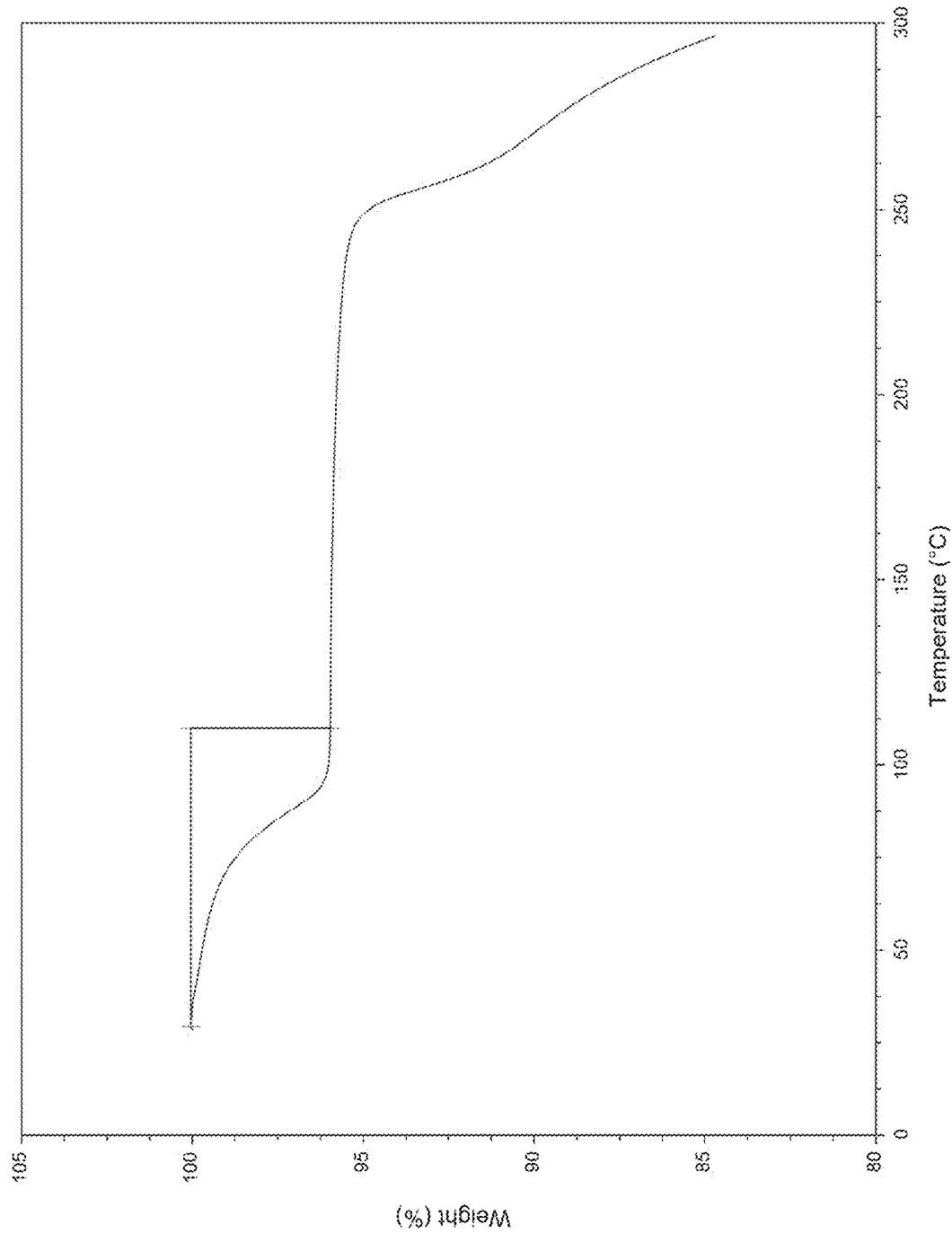
FIG. 15 shows the TGA trace of form example 1 hydrochloride (1:1).

FIG. 15 shows the TGA trace of form example 1 hydrochloride (1:1).

Reference Example 1: (R)-3-Methyl-2-(5-methyl-6-((1-methylpiperidin-3-yl)amino)pyridazin-3-yl)-5-(trifluoromethyl)phenol

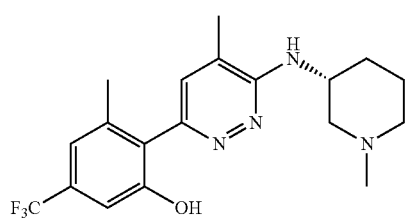 [SMILES: Cc1cc(-c2c(C)cc(C(F)(F)F)cc2O)nnc1N[C@@H]1CCCN(C)C1]

This compound may be prepared as described in WO2020/234715, example Ex 005.

Reference Example 2: (R)-3-methyl-2-(6-((1-methylpiperidin-3-yl)amino)-5-(trifluoromethyl)pyridazin-3-yl)-5-(trifluoromethyl)phenol

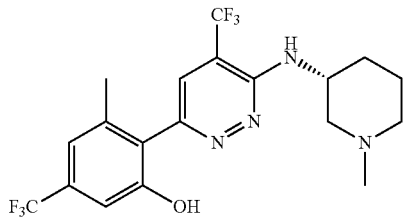 [SMILES: Cc1cc(C(F)(F)F)cc(O)c1-c1cc(C(F)(F)F)c(N[C@@H]2CCCN(C)C2)nn1]

This compound may be prepared as described in WO2020/234715, example Ex 064.

Reference Example 3: 3-methyl-2-(4-(((R)-1-methylpiperidin-3-yl)amino)-5,7-dihydrofuro[3,4-d]pyridazin-1-yl)-5-(trifluoromethyl)phenol

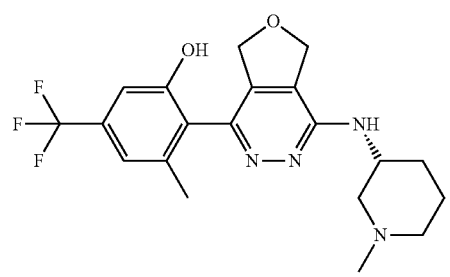

This compound may be prepared as described in WO2022/135567, example Ex 42.

Biological Assays and Data

The activity of a compound according to the present invention can be assessed by the following in vitro methods. A compound of formula (I), or a pharmaceutically acceptable salt thereof, exhibits valuable pharmacological properties, e.g. properties susceptible to inhibit NLRP3 activity, e.g. as indicated in tests as provided in the next sections, and are therefore indicated for therapy related to NLRP3 inflammasome activity.

IL-1β Secretion Assay:

Monocytic THP-1 cells (ATCC: TIB-202) were maintained according to providers' instructions in RPMI media (RPMI/Hepes+10% fetal bovine serum+Sodium Pyruvate+0.05 mM Beta-mercaptoethanol (1000× stock)+Pen-Strep). Cells were differentiated in bulk with 0.5 μM phorbol 12-myristate 13-acetate (PMA; Sigma #P8139) for 3 h, media was exchanged, and cells were plated at 50,000 cells per well in a 384-well flat-bottom cell culture plates (Greiner, #781986), and allowed to differentiate overnight. Compound in a 1:3.16 serial dilution series in DMSO was added 1:100 to the cells and incubated for 1 h. The NLRP3 inflammasome was activated with the addition of 15 μM (final concentration) Nigericin (Enzo Life Sciences, #BML-CA421-0005), and cells were incubated for 3 h. 10 μL supernatant was removed, and IL-1β levels were monitored using an HTRF (Homogeneous Time Resolved Fluorescence) assay (CisBio, #62IL1PEC) according to manufacturers' instructions. Viability and pyroptosis was monitored with the addition of PrestoBlue cell viability reagent (Life Technologies, #A13261) directly to the cell culture plate.

TNF-α Secretion Assay:

Monocytic THP-1 cells were maintained according to providers' instructions in RPMI media as described above. Undifferentiated cells were plated at 50,000 cells per well in a 384-well flat-bottom cell culture plates (Greiner, #781986), and allowed to rest overnight. Experimental compounds were prepared and added as described above. TNF-α secretion was triggered by the addition of either 1 μg/mL LPS (Sigma, #L4391) or 100 ng/ml Pam3CSK4 (Invivogen, #tlrl-pms) depending on the experiment, and cells were incubated for 3 h. 10 μL supernatant was removed, and TNF-α levels were monitored using an HTRF assay (Cis-Bio, #62TNFPEC) according to manufacturers' instructions. Viability was monitored as Data Interpretation:

$IC_{50}$ values were calculated from the plot of percentage of inhibition versus the inhibitor concentration by a logistics fit according to:

$$y = A2 + (A1 - A2)/(1 + (x/IC_{50})^p)$$

where y is the %-inhibition at the inhibitor concentration, x. A1 is the lowest inhibition value, i.e. 0%, and A2 the maximum inhibition value, i.e. 100%. The exponent, p, is the Hill coefficient. The curve fitting was conducted with an internally developed software suite. NLRP3-dependent IL-1β secretion was stimulated in PMA-differentiated THP-1 cells by the addition of nigericin, and cytokines were measured in the serum after 3 h. As discussed above, activation of the NLRP3 inflammasome requires both an NF-κB-dependent priming step and the addition of a NLRP3 activator. To ensure that the inhibitors did not interfere with the priming step, Pam3CSK4-stimulated, NF-κB-dependent TNF-α secretion was monitored as a counter screen. Data for the inhibitory effect ($IC_{50}$) of the compounds of the invention for both assays are given in the table below. Data for IL-1β secretion was calculated as the arithmetic mean of at least 3 individual experiments, and TNF-α secretion data was consistent across at least 2 individual replicates.

| Example No. | IL-1β $IC_{50}$ [μM] | TNF-α $IC_{50}$ [μM] |
|---|---|---|
| 1 | 0.00072 | >100 |
| Reference ex. 1 | 0.0030 | >33 |
| Reference ex. 2 | 0.0059 | >100 |
| Reference ex. 3 | 0.0037 | >100 | hERG Channel Test Using the QPatch Technology[4]

CHO cells (AVIVA Biosciences Corp, San Diego, CA) stably expressing hERG channels were patched using a QPatch-HT automated patch clamp instrument (Sophion Bioscience A/S, Ballerup, Denmark) in single hole mode. The intracellular solution consisted of 120 mM KCl, 5 mM $CaCl_2$, 2 mM $MgCl_2$, 10 mM ethylene glycolbis (2-aminoethylether)-N,N,N',N'-tetraacetic acid (EGTA), 10 mM (4-(2-hydroxyethyl)-1-piperazineethanesulfonic acid (HEPES), and 4 mM dipotassium adenosine-5'-triphosphate (ATP-K2), pH adjusted to 7.2 using KOH. The extracellular solution consisted of 145 mM NaCl, 4 mM KCl, 2 $CaCl_2$, 1 mM $MgCl_2$, 10 mM HEPES, and 0.3% dimethyl sulfoxide (DMSO), adjusted to pH 7.4 using NaOH. All measurements were performed at room temperature, and the blockers were pre-incubated for 4 min. The cells were voltage clamped at −90 mV and the hERG current was activated using a voltage step to +20 mV for 4 s. The hERG tail currents were measured by stepping down to −50 mV for 4 s before returning to −90 mV. This protocol was repeated every 20 s. The peak hERG current was automatically corrected by subtracting the leak current, which was estimated by measuring the mean current during a short depolarizing step to −50 mV from the resting membrane potential just prior to the long depolarizing step to +20 mV at the beginning of the voltage protocol. Test articles were diluted using DMSO stock solutions and the extracellular solution. The final concentration of the vehicle DMSO did not exceed 0.3%. The effect of the test article on the hERG tail current was assessed and 1, 10 and 30 μM and a positive control (amitriptiline, 1, 3 and μM) was included on each plate. If the inhibitory activity was >50% at the highest test concentration data points were fitted to a standard Hill equation and a IC50-value was determined, using a fixed minimum current at 0% and maximum current at 100% (Remaining current (%)=MaxI+((MinI−MaxI)/(1+((Conc./$IC_{50}$)^Hill))) where MaxI=100 MinI=0. If the hERG activity was less than 50% at the highest test concentration that the hERG $IC_{50}$-value was estimated to be greater than this (e.g. >30 μM).

4) Robert A Pearlstein, K Andrew MacCannell, Gül Erdemli, Sarita Yeola, Gabriel Helmlinger, Qi-Ying Hu, Ramy Farid, William Egan, Steven Whitebread, Clayton Springer, Jeremy Beck, Hao-Ran Wang, Mateusz Maciejewski, Laszlo Urban, José S Duca *Current Topics in Medicinal Chemistry* (2016), 16:1792-1818.

| Example No. | hERG QPatch $IC_{50}$ [μM]/% inhibition |
|---|---|
| 1 | >30/24.3 |
| Reference ex. 1 | 13.1/64.7 |
| Reference ex. 2 | 3.9/93.6 | hERG Electrophysiological Inhibition Assay Using the Qube Technology

Chinese hamster ovary (CHO) cell line, overexpressing the alpha-subunit of the hERG channel under the control of tetracycline-regulated promoter, was created using commercially available T-REX™ system (Invitrogen). CHO (T-REX™) hERG cells were maintained in Ham's F-12 nutrient medium (Life Tech) supplemented with 10% fetal bovine serum (HyClone), 1% penicillin-streptomycin, 10 μg/mL Blasticidin and 50 μg/mL Zeocin (all from Life Technologies, Thermo Fisher Scientific). For hERG expression induction, 1 μg/ml tetracycline (Sigma-Aldrich) was added to the growth media 24 hours before the current recording. To prepare the cell suspension for Qube experiments, cells were dislodged from culture flask by incubation in Detachin (Genlantis) at 37° C. for approximately 5 min, and resuspended in CHO serum free media (CHO-SFM II, Life Technologies) at a density of 2-3 million cells per mL.

Patch clamp experiments were performed on the Qube APC (automated patch clamp) platform (Sophion Bioscience A/S, Ballerup, Denmark) using the 384X 10-hole chip at 35° C. Intracellular KF-Ringer's solution consisted of (in mM) 120 KF, 20 KCl, 2 10 ethylene glycol-bis(2-aminoethylether)-N,N,N',N'-tetraacetic acid (EGTA) and 10 (4-(2-hydroxyethyl)-1-piperazineethanesulfonic acid (HEPES), pH at 7.2 with KOH. Extracellular solution consisted of (in mM) 145 NaCl, 4 KCl, 2 CaCl2, 1 MgCl2, 10 HEPES, 10

Glucose and 0.3% dimethyl sulfoxide (DMSO), pH at 7.4 with NaOH. The hERG current was elicited by applying the following voltage protocol: cells are held at −90 mV resting membrane potential for 100 msec, then clamped at −50 mV for 100 msec for leak estimation, depolarized to +20 mV for 4 sec (peak current measurement) and finally repolarized to −50 mV for 4 sec (tail current recording) before returning to the holding potential of −90 mV. The data are sampled at 10 KHz, with cutoff at 2 kHz, and filtered using the Bessel filter. The protocol was repeated every 15 s, 30 times before and 30 times after a compound application.

All compounds were prepared as 10 mM stock in 100% DMSO, then serially dilutes 1:3 down in Labcyte 384-well Echo Qualified LDV (low diamond volume) microplate. The Qube assay plate was prepared by transferring 0.15-0.3 µL of a compound from the serial dilution plate to the 384-well Greiner plate using Labcyte Echo 650 liquid handler (Beckman). Right before the experiment, the compounds in each well were further diluted in extracellular solution using Biomek i7 liquid handler (Beckman) to create the final concentrations of 0.37, 1.1, 3.3, 10, 15 and 30 µM (1:333 dilution to keep the final DMSO concentration in all samples ≤0.3%). Amitriptyline hydrochloride (positive control) and DMSO (0.3%, vehicle control) were included in each plate.

The results were initially reviewed using the Qube specific Sophion Analyzer software (Sophion Bioscience), then analyzed using Data Analysis and Visualization in Discovery (DAVID) software package (Novartis AG). The compound effect on hERG current inhibition (normalized percentage of inhibition) was calculated as % Inh=($I_{compound}$−$I_{vehicle}$)/Ivehicle*−100, where $I_{compound}$ and $I_{vehicle}$ are the averages of the last three leak-corrected tail hERG currents before and after a compound application, respectively. For compound concentration responses, a custom four-parameter fit to Hill equation was used to derive IC50 values (with fixed minimum current at 0% and maximum current at 100%): $I(C)=I_b+((I_f-I_b)*C^n)/IC50+C^n$, where C is the input concentration, I(C) is the remaining current after the inhibition by a test compound, $I_b$ is the maximal current before the compound application and $I_f$ is a fixed minimum current. All the data and assay-specific information are stored in company internal database for biochemical assays (Pharon).

| Example No. | hERG Qube $IC_{50}$ [µM] | % inhibition at 30 µM |
|---|---|---|
| 1 | >30 | 40.9 |
| Reference ex. 1 | 4.71 | 77.9 |
| Reference ex. 2 | 5.62 | 74.9 |
| Reference ex. 3 | >30 | 49.8 |

Activity on the hERG channel is known to, undesirably, cause QTc prolongation in the clinic. Such QTc prolongation means the heart muscle takes longer than normal to recharge between beats, and which can cause adverse safety effects. Therefore, the *in vitro* hERG assay is used to assess the interaction of a drug molecule with the channel and aid the medicinal chemist in finding a drug candidate which will not have this serious toxicity in the clinic. A higher hERG $IC_{50}$ is favourable for the cardiac safety evaluation of compounds.

Reference example 1 and 2 were found to have a hERG QPatch $IC_{50}$ of 13.1 and 3.9, respectively, and a hERG Qube $IC_{50}$ of 4.71 and 5.62, respectively. Surprisingly, it was found that example 1 had a considerably increased hERG QPatch $IC_{50}$ and hERG Qube $IC_{50}$, thus providing a compound with an improved drug safety profile. Thus, the introduction of $R^4$ is —$(CH_2)_n$—OH, wherein n is 1, 2, 3 or 4, in compounds of formula (I) having the general structure

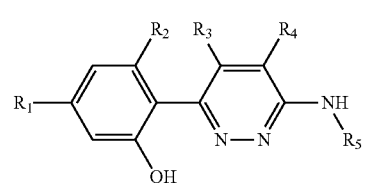

has led unexpectedly to compounds with an improved drug safety profile.

What is claimed is:

1. A compound, or a pharmaceutically acceptable salt thereof, having the following structure:

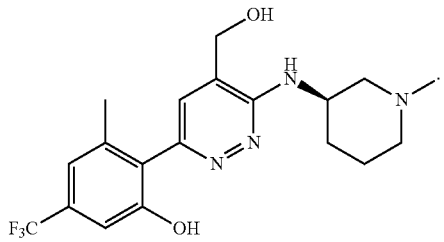

2. A pharmaceutical composition comprising a therapeutically effective amount of a compound according to claim 1, or a pharmaceutically acceptable salt thereof, and one or more pharmaceutically acceptable carriers.

3. The compound of claim 1, wherein the compound is in a crystalline form.

4. The compound according to claim 3, wherein the crystalline form is selected from a hydrate, form A, form B, a hippurate salt and a hydrochloride salt.

5. The compound according to claim 3, wherein the crystalline form has an X-ray powder diffraction pattern as shown in any one of FIG. 1, FIG. 4, FIG. 7, FIG. 10, or FIG. 13, or FIG. 13, when measured using CuKα radiation.

6. The compound according to claim 3, wherein the crystalline form is a hydrate.

7. The compound according to claim 6, wherein the ratio of compound to water molecule is 1:1.

8. The compound according to claim 3, wherein the compound is a hydrochloride salt.

9. The compound according to claim 3, wherein the crystalline form has an X-ray powder diffraction pattern comprising at least one peak having an angle of refraction 2θ values (CuKα λ=1.5418 Å) selected from 20.2°, 20.5°, 21.1° and 23.2°, measured at a temperature of about 25° C. and an x-ray wavelength, λ, of 1.5418 Å.

10. The compound according to claim 3, wherein the crystalline form has an X-ray powder diffraction pattern comprising at least two peaks having an angle of refraction 2θ values (CuKα λ=1.5418 Å) selected from 20.2°, 20.5°, 21.1° and 23.2°, measured at a temperature of about 25° C. and an x-ray wavelength, λ, of 1.5418 Å.

11. The compound according to claim 3, wherein the crystalline form has an X-ray powder diffraction pattern comprising at least three peaks having an angle of refraction 2θ values (CuKα λ=1.5418 Å) selected from 20.2°, 20.5°, 21.1° and 23.2°, measured at a temperature of about 25° C. and an x-ray wavelength, λ, of 1.5418 Å.

12. The compound according to claim 3, wherein the crystalline form has an X-ray powder diffraction pattern comprising at least four peaks having an angle of refraction 2θ values (CuKα 2=1.5418 Å) selected from 20.2°, 20.5°, 21.1° and 23.2°, measured at a temperature of about 25° C. and an x-ray wavelength, λ, of 1.5418 Å.

13. The compound according to claim 9, wherein the X-ray powder diffraction pattern further comprises at least one peak having an angle of refraction 2θ values (CuKα λ=1.5418 Å) selected from 16.2°, 16.6°, 18.0, 24.0° and 28.1°, measured at a temperature of about 25° C. and an x-ray wavelength, λ, of 1.5418 Å.

14. The compound according to claim 9, wherein the X-ray powder diffraction pattern further comprises at least two peaks having an angle of refraction 2θ values (CuKα λ=1.5418 Å) selected from 16.2°, 16.6°, 18.0, 24.0° and 28.1°, measured at a temperature of about 25° C. and an x-ray wavelength, λ, of 1.5418 Å.

15. The compound according to claim 9, wherein the X-ray powder diffraction pattern further comprises at least three peaks having an angle of refraction 2θ values (CuKα λ=1.5418 Å) selected from 16.2°, 16.6°, 18.0, 24.0° and 28.1°, measured at a temperature of about 25° C. and an x-ray wavelength, λ, of 1.5418 Å.

16. The compound according to claim 9, wherein the X-ray powder diffraction pattern further comprises at least four peaks having an angle of refraction 2θ values (CuKα λ=1.5418 Å) selected from 16.2°, 16.6°, 18.0, 24.0° and 28.1°, measured at a temperature of about 25° C. and an x-ray wavelength, λ, of 1.5418 Å.

17. The compound according to claim 9, wherein the X-ray powder diffraction pattern further comprises five peaks having an angle of refraction 2θ values (CuKα λ=1.5418 Å) selected from 16.2°, 16.6°, 18.0, 24.0° and 28.1°, measured at a temperature of about 25° C. and an x-ray wavelength, λ, of 1.5418 Å.

18. The compound according to claim 3, which has an X-ray powder diffraction pattern as shown in FIG. 1 when measured using CuKα radiation.

\* \* \* \* \*